US012559507B2

(12) United States Patent
Koradin et al.

(10) Patent No.: US 12,559,507 B2
(45) Date of Patent: Feb. 24, 2026

(54) METHOD FOR PREPARING AN ENANTIOMERICALLY ENRICHED FORM OF 3-(2-CHLOROTHIAZOL-5-YL)-8-METHYL-7-OXO-6-PHENYL-2,3-DIHYDROTHIAZOLO[3,2-AJPYRIMIDIN-4-IUM-5-OLATE

(71) Applicant: BASF SE, Ludwigshafen (DE)

(72) Inventors: Christopher Koradin, Ludwigshafen (DE); Martin John McLaughlin, Liestal (CH); Harish Shinde, Navi Mumbai (IN); Rahul Kaduskar, Navi Mumbai (IN); Roland Goetz, Ludwigshafen (DE); Guillaume Michel Jacques Garivet, Ludwigshafen (DE)

(73) Assignee: BASF SE, Ludwigshafen (DE)

( * ) Notice: Subject to any disclaimer, the term of this patent is extended or adjusted under 35 U.S.C. 154(b) by 398 days.

(21) Appl. No.: 18/272,884

(22) PCT Filed: Jan. 21, 2022

(86) PCT No.: PCT/EP2022/051362

§ 371 (c)(1),
(2) Date: Jul. 18, 2023

(87) PCT Pub. No.: WO2022/157321

PCT Pub. Date: Jul. 28, 2022

(65) Prior Publication Data

US 2023/0416273 A1 Dec. 28, 2023

(30) Foreign Application Priority Data

Jan. 22, 2021 (EP) .................................... 21153036

(51) Int. Cl.
*C07D 513/04* (2006.01)

(52) U.S. Cl.
CPC .................................. *C07D 513/04* (2013.01)

(58) Field of Classification Search
CPC .................................................... C07D 513/04
See application file for complete search history.

(56) References Cited

FOREIGN PATENT DOCUMENTS

| | | | |
|---|---|---|---|
| CN | 109970731 | B | 5/2020 |
| EP | 4032878 | A1 | 7/2022 |
| WO | WO-2014/167084 | A1 | 10/2014 |
| WO | WO-2018/177970 | A1 | 10/2018 |
| WO | WO-2018/197541 | A1 | 11/2018 |
| WO | WO-2018/202654 | A1 | 11/2018 |

OTHER PUBLICATIONS

International Application No. PCT/EP2022/051362, International Search Report and Written Opinion, mailed Apr. 4, 2022.
European Patent Application No. 21153036.5, Extended European Search Report, mailed May 7, 2021.
Chalopin, et al., "Second generation of thiazolylmannosides, FimH antagonists for *E. coli*-induced Crohn's disease", Organic & Biomolecular Chemistry, vol. 14, Issue 16, Mar. 22, 2016, pp. 3913-3925.

*Primary Examiner* — Alicia L Otton
(74) *Attorney, Agent, or Firm* — MARSHALL, GERSTEIN & BORUN LLP

(57) ABSTRACT

The present invention relates to a method for preparing an enantiomerically enriched form of 3-(2-chlorothiazol-5-yl)-8-methyl-7-oxo-6-phenyl-2,3-dihydrothiazolo[3,2-a]pyrimidin-4-ium-5-olate.

25 Claims, No Drawings

METHOD FOR PREPARING AN ENANTIOMERICALLY ENRICHED FORM OF 3-(2-CHLOROTHIAZOL-5-YL)-8-METHYL-7-OXO-6-PHENYL-2,3-DIHYDROTHIAZOLO[3,2-AJPYRIMIDIN-4-IUM-5-OLATE

CROSS-REFERENCE TO RELATED APPLICATIONS

This is the U.S. national phase of International Application No. PCT/EP2022/051362, filed Jan. 21, 2022, which claims the benefit of European Patent Application No. 21153036.5, filed Jan. 22, 2021.

The present invention relates to a method for preparing an enantiomerically enriched form of 3-(2-chlorothiazol-5-yl)-8-methyl-7-oxo-6-phenyl-2,3-dihydrothiazolo[3,2-a]pyrimidin-4-ium-5-olate. The invention relates moreover to 2-[2-(2-chlorothiazol-5-yl)-2-hydroxy-ethyl]sulfanyl-6-hydroxy-3-methyl-5-phenyl-pyrimidin-4-one of the formula 2 as depicted below or enantiomerically enriched forms thereof, and to its use as intermediate in the preparation of 2,3-dihydrothiazolo[3,2-a]pyrimidinium compounds, specifically of 3-(2-chlorothiazol-5-yl)-8-methyl-7-oxo-6-phenyl-2,3-dihydrothiazolo[3,2-a]pyrimidin-4-ium-5-olate and enantiomerically enriched forms thereof.

TECHNICAL BACKGROUND 3-(2-Chlorothiazol-5-yl)-8-methyl-7-oxo-6-phenyl-2,3-dihydrothiazolo[3,2-a]pyrimidin-4-ium-5-olate and enantiomerically enriched forms thereof has insecticidal properties and is known, for example, from WO 2018/177970 or WO 2014/167084.

The methods thus far known for the preparation of this pyrimidinium compound are cumbersome and not yet satisfactory.

In WO 2018/177970, WO 2018/197541 and WO 2018/202654, non-racemic 2,3-dihydrothiazolo[3,2-a]pyrimidinium compounds are prepared by reaction of a non-racemic 4-heteroaryl-substituted thiazolidin-2-imine with a 2-substituted malonic acid derivative. In WO 2018/177970 and WO 2018/197541, the non-racemic 4-heteroaryl-substituted thiazolidin-2-imine is in turn prepared by catalytic asymmetric hydrogenation of a 1-heteroaryl-substituted ethanimine carrying in 2-position a leaving group. The resulting amine is then reacted with an isothiocyanate to the thiazolidin-2-imine. The reaction sequence is described in WO 2018/197541 as follows:

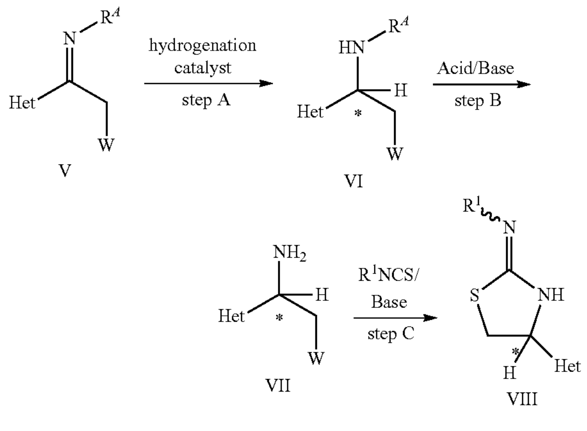

-continued

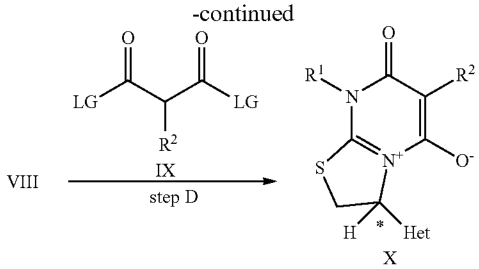

$R^A$ is a sulfanyl or sulfinyl, phosphoroxy, alkoxy or benzyl group; Het is optionally substituted pyridin-3-yl, thiazol-5-yl or pyrimidin-5-yl, W and LG are leaving groups, $R^1$ is a (cyclo)aliphatic group and $R^2$ is 5- or 6-membered carbo- or heterocyclic ring. In WO 2018/177970 the amine VII is obtained via another reaction path from the corresponding sulfinylimine.

WO 2018/177970 and WO 2018/202654 describe a further access to the non-racemic 4-heteroaryl-substituted thiazolidin-2-imine. This is here prepared starting from a heteroarylmethyl ketone, where the methyl group carries a leaving group, conversion of this leaving group into an alkylcarbonyloxy group, hydrolysis of the latter to a hydroxyl group, reaction of the resulting heteroarylhydroxymethyl ketone with a sulfamoyl halide to a 4-heteroaryl-5H-oxathiazole 2,2-dioxide, submission of the latter to a catalytic asymmetric hydrogenation to yield a non-racemic 4-heteroaryloxathiazolidine 2,2-dioxide and reaction thereof with an isothiocyanate to the thiazolidin-2-imine. The reaction sequence is described in WO 2018/202654 as follows:

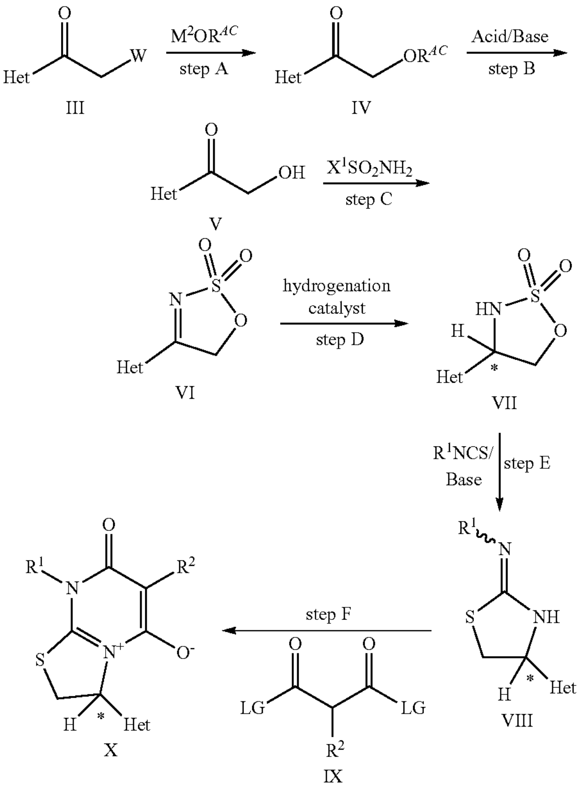

Het is optionally substituted pyridin-3-yl, thiazol-5-yl or pyrimidin-5-yl, W and LG are leaving groups, $M^2$ is Li, Na, K, Al, Ba, Cs, Ca or Mg, $R^{AC}$ is alkylcarbonyl, $X^1$ is halogen, $R^1$ is a (cyclo)aliphatic group and $R^2$ is 5- or 6-membered carbo- or heterocyclic ring.

These methods are however not very economic. Some reagents are expensive, recycling of some of the reagents which are not or not entirely consumed is difficult, the overall yield is not satisfactory and too many reaction steps are involved.

SUMMARY OF THE INVENTION

It was the object of the present invention to provide an economic process for the preparation of 3-(2-chlorothiazol-5-yl)-8-methyl-7-oxo-6-phenyl-2,3-dihydrothiazolo[3,2-a]pyrimidin-4-ium-5-olate and especially a process for the preparation of an enantiomerically enriched form thereof which yields the S or R enantiomer with high selectivity.

The problem is solved by a method for preparing an enantiomerically enriched form of 3-(2-chlorothiazol-5-yl)-8-methyl-7-oxo-6-phenyl-2,3-dihydrothiazolo[3,2-a]pyrimidin-4-ium-5-olate of the formula (I):

(I)

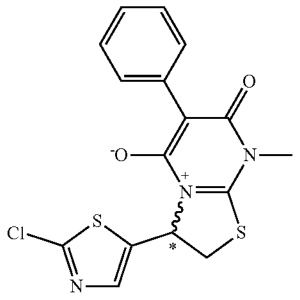

where the asterisk * shows the stereogenic center; which method comprises (a) reducing 2-[2-(2-chlorothiazol-5-yl)-2-oxo-ethyl]sulfanyl-6-hydroxy-3-methyl-5-phenyl-pyrimidin-4-one of the formula 1

1

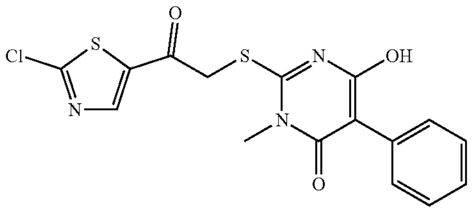

or a tautomer thereof or a mixture of different tautomers thereof with a reduction agent selected from the group consisting of formic acid HC(═O)OH, formates of the formula $HC(=O)O^-M^+$ and mixtures of formic acid HC(═O)OH and one or more formates of the formula $HC(=O)O^-M^+$, where $M^+$ is a cation equivalent; in the presence of a chiral transition metal catalyst and optionally of a base, where in case that formic acid is used as reduction agent, the reaction is carried out in the presence of a base;

to obtain a reaction mixture comprising an enantiomerically enriched form of 2-[2-(2-chlorothiazol-5-yl)-2-hydroxy-ethyl]sulfanyl-6-hydroxy-3-methyl-5-phenyl-pyrimidin-4-one of the formula 2

2

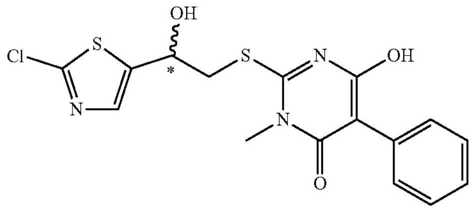

or of a tautomer thereof or a mixture of different tautomers thereof; and (b) reacting the reaction mixture obtained in step (a) with an activating agent which enhances electrophilicity of the carbon atom marked with the asterisk in the compound of the formula 1 without promoting racemization at said carbon atom; to obtain an enantiomerically enriched form of the compound of the formula (I).

The invention relates moreover to 2-[2-(2-chlorothiazol-5-yl)-2-hydroxy-ethyl]sulfanyl-6-hydroxy-3-methyl-5-phenyl-pyrimidin-4-one 2 or a tautomer thereof or a mixture of different tautomers thereof and to enantiomerically enriched forms thereof.

The invention relates also to the use of 2-[2-(2-chlorothiazol-5-yl)-2-hydroxy-ethyl]sulfanyl-6-hydroxy-3-methyl-5-phenyl-pyrimidin-4-one 2 or of a tautomer thereof or of a mixture of different tautomers thereof or of enantiomerically enriched forms thereof as intermediate in the preparation of 2,3-dihydrothiazolo[3,2-a]pyrimidinium compounds, specifically of 3-(2-chlorothiazol-5-yl)-8-methyl-7-oxo-6-phenyl-2,3-dihydrothiazolo[3,2-a]pyrimidin-4-ium-5-olate (I) and enantiomerically enriched forms thereof.

DETAILED DESCRIPTION OF THE INVENTION

Definitions

"Enantiomerically enriched form" of 3-(2-chlorothiazol-5-yl)-8-methyl-7-oxo-6-phenyl-2,3-dihydrothiazolo[3,2-a]pyrimidin-4-ium-5-olate of the formula (I) or the compound (I) in enantiomerically enriched form" and similar terms denote a non-racemic compound (I) in which either the S enantiomer or the R enantiomer predominates or is even present as only stereoisomer. The compound (I) has a single stereogenic center which is at the ring carbon atom carrying the thiazole ring and marked with an asterisk.

"Enantiomerically enriched form" of 2-[2-(2-chlorothiazol-5-yl)-2-hydroxy-ethyl]sulfanyl-6-hydroxy-3-methyl-5-phenyl-pyrimidin-4-one of the formula 2 or the compound 2 in enantiomerically enriched form" and similar terms denote a non-racemic compound 2 in which either the S enantiomer or the R enantiomer predominates or is even present as only stereoisomer. The compound 2 has a single stereogenic center which is at the aliphatic carbon atom carrying the OH group and marked with an asterisk.

$M^+$ is a cation equivalent. It stands for a metal cation or an ammonium cation (ammonium in this case stands for both the ammonium cation $NH_4^+$ in the proper sense, but also for substituted ammonium cations). In case of cations with double or triple charge, the cation equivalent can be depicted as $(M^{n+})_{1/n}$, where n is the charge number.

Formate in the context of the present invention is a salt of formic acid ($HC(=O)O^-M^+$, where $M^+$ is a cation equivalent). The term can also stand for the anion ($HC(=O)O^-$) of formic acid. In context of the present invention, the term does however not denote the esters, unless explicitly mentioned otherwise.

The organic moieties mentioned below are—like the term halogen—collective terms for individual listings of the individual group members. The prefix $C_n$-$C_m$ indicates in each case the possible number of carbon atoms in the group.

The term halogen denotes in each case fluorine, bromine, chlorine or iodine, in particular fluorine, chlorine or bromine.

The term "alkyl" as used herein and in the alkyl moieties of alkoxy refers to saturated straight-chain (linear) or branched hydrocarbon radicals having 1 to 3 ("$C_1$-$C_3$-alkyl"), 1 to 4 ("$C_1$-$C_4$-alkyl") or 1 to 6 ("$C_1$-$C_6$-alkyl") carbon atoms. $C_1$-$C_3$-Alkyl denotes a saturated linear or branched aliphatic radical with 1 to 3 carbon atoms. Examples are methyl, ethyl, n-propyl or isopropyl. $C_1$-$C_4$-Alkyl denotes a saturated linear or branched aliphatic radical with 1 to 4 carbon atoms. Examples are methyl, ethyl, n-propyl, isopropyl, n-butyl, sec-butyl, isobutyl and tert-butyl. $C_1$-$C_6$-Alkyl denotes a saturated linear or branched aliphatic radical with 1 to 6 carbon atoms. Examples are, in addition to those mentioned for $C_1$-$C_4$-alkyl, pentyl, 1-methylbutyl, 2-methylbutyl, 3-methylbutyl, 2,2-dimethylpropyl, 1-ethylpropyl, 1,1-dimethylpropyl, 1,2-dimethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, or 1-ethyl-2-methylpropyl.

The term "$C_1$-$C_4$-haloalkyl" as used herein, which can also be expressed as "alkyl which is partially or fully halogenated", refers to straight-chain or branched alkyl groups having 1 to 4 carbon atoms (as mentioned above), where some or all of the hydrogen atoms in these groups are replaced by halogen atoms as mentioned above. Examples are chloromethyl, bromomethyl, dichloromethyl, trichloromethyl, fluoromethyl, difluoromethyl, trifluoromethyl, chlorofluoromethyl, dichlorofluoromethyl, chlorodi-fluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl or pentafluoroethyl. $C_1$-$C_3$-haloalkyl is additionally, for example, 1-fluoropropyl, 2-fluoropropyl, 3-fluoropropyl, 1,1-difluoropropyl, 2,2-difluoropropyl, 1,2-difluoropropyl, 3,3-difluoropropyl, 3,3,3-trifluoropropyl, heptafluoro-propyl, 1,1,1-trifluoroprop-2-yl, 3-chloropropyl, 4-chlorobutyl and the like.

The term "$C_3$-$C_6$-cycloalkyl" as used herein refers to monocyclic saturated hydrocarbon radicals having 3 to 6 carbon atoms as (only) ring members. Examples are cyclopropyl, cyclobutyl, cyclopentyl and cyclohexyl.

The term $C_6$-$C_{10}$-bicycloalkyl refers to bicyclic bridged saturated hydrocarbon radicals containing 6 to 10 carbon atoms as (only) ring members. Examples are bicyclo[2.2.1]heptyl, bicyclo[3.1.1]heptyl, bicyclo [2.2.2]octyl, bicyclo[3.2.1]octyl and the like. Examples for $C_6$-$C_{10}$-bicycloalkyl substituted by alkyl and/or oxo are 7,7-dimethyl-bicyclo[2.2.1]hept-1-yl and 7,7-dimethyl-2-oxo-bicyclo[2.2.1]hept-1-yl.

The term $C_6$-$C_{10}$-bicycloalkyl-$C_1$-$C_3$-alkyl refers to a straight-chain or branched alkyl group having 1 to 3 carbon atoms, as defined above, where one hydrogen atom is replaced by a $C_6$-$C_{10}$-bicycloalkyl group, as defined above.

The term "$C_1$-$C_4$-alkoxy" refers to a $C_1$-$C_4$-alkyl group, as defined above, attached via an oxygen atom to the remainder of the molecule. Examples are methoxy, ethoxy, n-propoxy, 1-methylethoxy (isopropoxy), n-butoxy, 1-methylpropoxy (sec-butoxy), 2-methylpropoxy (isobutoxy) or 1,1-dimethylethoxy (tert-butoxy).

The term "$C_1$-$C_4$-alkoxy-$C_1$-$C_4$-alkyl" refers to a straight-chain or branched alkyl group having 1 to 4 carbon atoms, as defined above, where one hydrogen atom is replaced by a $C_1$-$C_4$-alkoxy group, as defined above. Examples are methoxymethyl, eth-oxymethyl, propoxymethyl, isopropoxymethyl, n-butoxymethyl, sec-butoxymethyl, iso-butoxymethyl, tert-butoxymethyl, 1-methoxyethyl, 1-ethoxyethyl, 1-propoxyethyl, 1-isopropoxyethyl, 1-n-butoxyethyl, 1-sec-butoxyethyl, 1-isobutoxyethyl, 1-tert-butoxyethyl, 2-methoxyethyl, 2-ethoxyethyl, 2-propoxyethyl, 2-isopropoxyethyl, 2-n-butoxyethyl, 2-sec-butoxyethyl, 2-isobutoxyethyl, 2-tert-butoxyethyl, 1-methoxypropyl, 1-ethoxypropyl, 1-propoxypropyl, 1-isopropoxypropyl, 1-n-butoxypropyl, 1-sec-butoxypropyl, 1-isobutoxypropyl, 1-tert-butoxypropyl, 2-methoxypropyl, 2-ethoxypropyl, 2-propoxypropyl, 2-isopropoxypropyl, 2-n-butoxypropyl, 2-sec-butoxypropyl, 2-isobutoxypropyl, 2-tert-butoxypropyl, 3-methoxypropyl, 3-ethoxypropyl, 3-propoxypropyl, 3-isopropoxypropyl, 3-n-butoxypropyl, 3-sec-butoxypropyl, 3-isobutoxypropyl, 3-tert-butoxypropyl and the like.

"Phenyl-$C_1$-$C_3$-alkyl" refers to straight-chain or branched alkyl groups having 1 to 3 carbon atoms (as mentioned above), where one hydrogen atom is replaced by a phenyl ring (in other words: a phenyl group bound via a $C_1$-$C_3$-alkylene linker to the remainder of the molecule).

Alkylene is a linear or branched divalent alkanediyl radical. $C_1$-$C_3$-Alkylene is a linear or branched divalent alkyl radical having 1, 2 or 3 carbon atoms. Examples are $-CH_2-$, $-CH_2CH_2-$, $-CH(CH_3)-$, $-CH_2CH_2CH_2-$, $-CH(CH_3)CH_2-$, $-CH_2CH(CH_3)-$ and $-C(CH_3)_2-$, $C_2$-$C_6$-Alkylene is a linear or branched divalent alkyl radical having 2, 3, 4, 5 or 6 carbon atoms. Examples are $-CH_2CH_2-$, $-CH(CH_3)-$, $-CH_2CH_2CH_2-$, $-CH(CH_3)CH_2-$, $-CH_2CH(CH_3)-$, $-C(CH_3)_2-$, $-CH_2CH_2CH_2CH_2-$, $-CH(CH_3)CH_2CH_2-$, $-CH_2CH_2CH(CH_3)-$, $-C(CH_3)_2CH_2-$, $-CH_2C(CH_3)_2-$, $-(CH_2)_5-$, $-(CH_2)_6-$, and positional isomers thereof.

Linear $C_3$-$C_6$-alkylene is $-(CH_2)_3-$, $-(CH_2)_4-$, $-(CH_2)_5-$ or $-(CH_2)_6-$.

5- or 6-membered saturated heterocyclic rings containing one nitrogen atom as ring member and optionally one further heteroatom selected from N and O as ring member are for example pyrrolidine, pyrazolidine, imidazolidine, oxazolidine, isoxazolidine, piperidine, piperazine, or morpholine.

Oxo is $=O$; i.e. the substituent "oxo" replaces a $CH_2$ group by a $C(=O)$ group.

Group VIII metal catalysts refer to catalysts having a metal from group VIII of the periodic system of elements as central metal. Group VIII relates to the IUPAC group definition valid before 1985 and corresponds to groups 8, 9 and 10 of the current IUPAC group designation.

The compound 1 can be present as a tautomer thereof or as a mixture of different tautomeric forms. An example for a tautomeric form of the compound of the formula 1 as depicted above is the following formula:

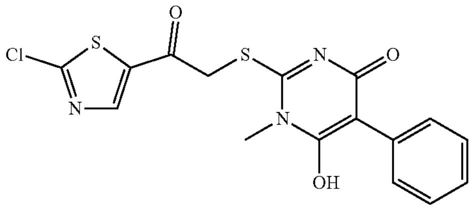 [SMILES: Cn1c(SCC(=O)c2cnc(Cl)s2)nc(=O)c(-c2ccccc2)c1O]

Mixtures of different tautomeric forms are for example mixtures of this tautomer the tautomer depicted above as formula 1.

The compound 2 can also be present as a tautomer thereof or as a mixture of different tautomeric forms. An example for a tautomeric form of the compound of the formula 2 as depicted above is the following formula:

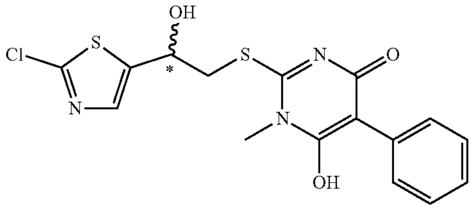 [SMILES: Cn1c(SCC(O)c2cnc(Cl)s2)nc(=O)c(-c2ccccc2)c1O]

Mixtures of different tautomeric forms are for example mixtures of this tautomer the tautomer depicted above as formula 2.

For the sake of simplicity, in the following only compounds 1 and 2 are mentioned. Nevertheless, all embodiments also relate to their tautomers and mixtures of different tautomeric forms thereof.

The condensed zwitterionic ring of the compound of formula (I) is mesomerically stabilized. The mesomeric forms of the condensed ring can for example be expressed in different isoelectronic formulae with the positive and negative charges distributed on different atoms, such as shown in the following:

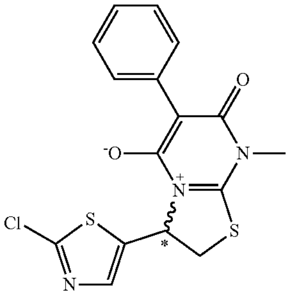

-continued

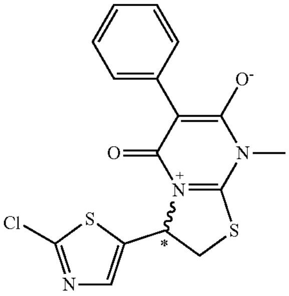

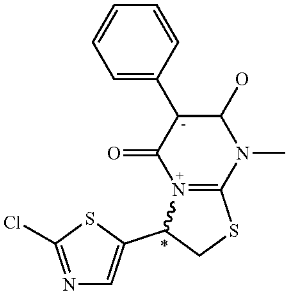

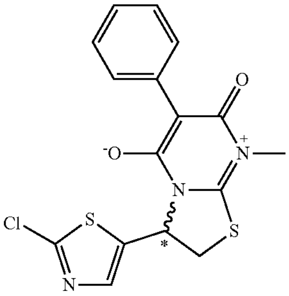

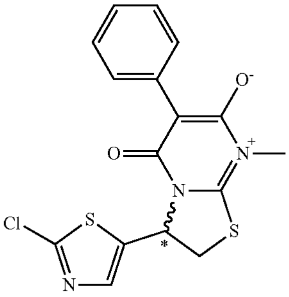

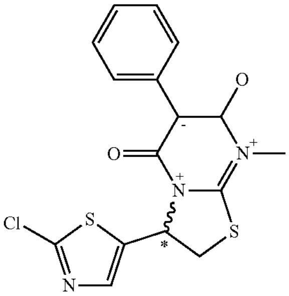

-continued

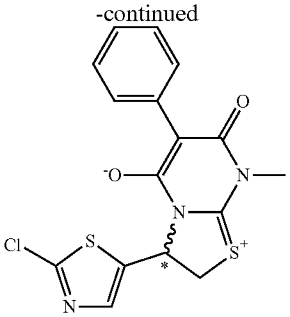

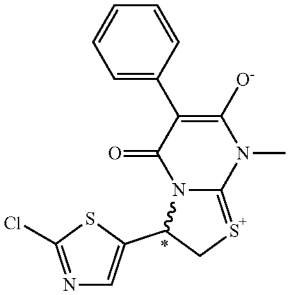

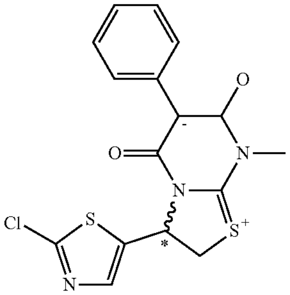

Embodiments (E.x) of the Invention

General and preferred embodiments E.x are summarized in the following, non-exhaustive list. Further preferred embodiments become apparent from the paragraphs following this list.

E.1. A method for preparing an enantiomerically enriched form of 3-(2-chlorothiazol-5-yl)-8-methyl-7-oxo-6-phenyl-2,3-dihydrothiazolo[3,2-a]pyrimidin-4-ium-5-olate of the formula (I):

(I)

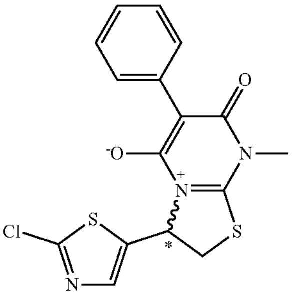

where the asterisk * shows the stereogenic center; which method comprises (a) reducing 2-[2-(2-chlorothiazol-5-yl)-2-oxo-ethyl]sulfanyl-6-hydroxy-3-methyl-5-phenyl-pyrimidin-4-one of the formula 1

1

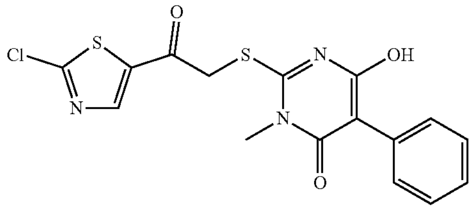

with a reduction agent selected from the group consisting of formic acid HC(═O)OH, formates of the formula $HC({=}O)O^-M^+$ and mixtures of formic acid HC(═O)OH and one or more formates of the formula $HC({=}O)O^-M^+$, where $M^+$ is a cation equivalent; in the presence of a chiral transition metal catalyst and optionally of a base, where in case that formic acid is used as reduction agent, the reaction is carried out in the presence of a base; to obtain a reaction mixture comprising an enantiomerically enriched form of 2-[2-(2-chlorothiazol-5-yl)-2-hydroxy-ethyl]sulfanyl-6-hydroxy-3-methyl-5-phenyl-pyrimidin-4-one of the formula 2

2

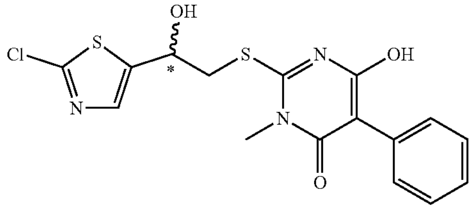

and (b) reacting the reaction mixture obtained in step (a) (without isolating the compound 2) with an activating agent which enhances electrophilicity of the carbon atom marked with the asterisk in the compound of the formula 1 without promoting racemization at said carbon atom;

to obtain an enantiomerically enriched form of the compound of the formula (I).

E.2. The method according to embodiment E.1, where $M^+$ is selected from the group consisting of alkali metal cations, ammonium cations of the formula $[NHR^1R^2R^3]^+$, where $R^1$, $R^2$ and $R^3$, independently of each other, are selected from the group consisting of hydrogen, $C_1$-$C_6$-alkyl, $C_3$-$C_6$-cycloalkyl, $C_1$-$C_4$-alkoxy and $C_1$-$C_4$-alkoxy-$C_1$-$C_4$-alkyl, protonated diamines of the formula $NR^1R^2$-A-$NR^3R^4$, where $R^1$, $R^2$, $R^3$ and $R^4$, independently of each other, are selected from the group consisting of hydrogen, $C_1$-$C_6$-alkyl, $C_3$-$C_6$-cycloalkyl, $C_1$-$C_4$-alkoxy and $C_1$-$C_4$-alkoxy-$C_1$-$C_4$-alkyl, and A is $(CH_2)_2$ or $(CH_2)_3$; and protonated 5- or 6-membered saturated heterocyclic rings containing one nitrogen atom as ring member and optionally one further heteroatom selected from N and O as ring member, where the ring may carry 1 to 6 $C_1$-$C_4$-alkyl groups and/or 1 or 2 OH groups.

E.3. The method according to embodiment E.2, where $M^+$ is selected from the group consisting of $Li^+$, $Na^+$, $K^+$, $Cs^+$, $NH_4^+$, $[NH_2(C_2H_5)_2]^+$, $[NH(C_2H_5)_3]^+$, [NH $(CH_2CH_2CH_2CH_3)_3]^+$, $[NH(C_2H_5)(CH(CH_3)_2]^+$, $[NH(CH_3)_2(CH(CH_3)]^+$, $[NH_2(C_2H_5)(C(CH_3)_3]^+$, $[NH_2(CH(CH_3)_2)(C(CH_3)_3]^+$, $[NH_2(C_2H_4OCH_3)(CH_3)]^+$, $[NH(cyclohexyl)_2(CH_3)]^+$, $[NH(cyclohexyl)(CH_3)_2]^+$, protonated N,N,N',N'-tetramethylethylenediamine, protonated N,N,N',N'-tetramethylpropylene-1,3-diamine, protonated piperdine, protonated N-methylpiperidine, protonated 2,2,6,6-tetramethylpiperidine, protonated N-methyl-2,6,6-tetramethylpiperidine, protonated N-methyl-4-hydroxy-2,2,6,6-tetramethylpiperidine, protonated morpholine, and protonated N-methylmorpholine.

E.4. The method according to embodiment E.2, where $M^+$ is selected from the group consisting of alkali metal cations and ammonium cations of the formula $[NHR^1R^2R^3]^+$, where $R^1$, $R^2$ and $R^3$, independently of each other, are selected from the group consisting of hydrogen and $C_1$-$C_6$-alkyl, where preferably at least one, preferably at least two of $R^1$, $R^2$ and $R^3$ are $C_1$-$C_6$-alkyl.

E.5. The method according to any of embodiments E.3 or E.4, where $M^+$ is selected from the group consisting of $[NH(C_2H_5)_3]^+$, $[NH(CH_2CH_2CH_2CH_3)_3]^+$ and $[NH(C_2H_5)(CH(CH_3)_2]^+$.

E.6. The method according to any of the preceding embodiments, where the base optionally or mandatorily used in step (a) is selected from the group consisting of alkali metal hydroxides, amines of the formula $NR^1R^2R^3$, where $R^1$, $R^2$ and $R^3$, independently of each other, are selected from the group consisting of hydrogen, $C_1$-$C_6$-alkyl, $C_3$-$C_6$-cycloalkyl, $C_1$-$C_4$-alkoxy and $C_1$-$C_4$-alkoxy-$C_1$-$C_4$-alkyl, where at least one of $R^1$, $R^2$ and $R^3$ is not hydrogen; diamines of the formula $NR^1R^2$-A-$NR^3R^4$, where $R^1$, $R^2$, $R^3$ and $R^4$, independently of each other, are selected from the group consisting of hydrogen, $C_1$-$C_6$-alkyl, $C_3$-$C_6$-cycloalkyl, $C_1$-$C_4$-alkoxy and $C_1$-$C_4$-alkoxy-$C_1$-$C_4$-alkyl, and A is $(CH_2)_2$ or $(CH_2)_3$; and a 5- or 6-membered saturated heterocyclic ring containing one nitrogen atom as ring member and optionally one further heteroatom selected from N and O as ring member, where the ring may carry 1 to 6 $C_1$-$C_4$-alkyl groups and/or 1 or 2 OH groups.

E.7. The method according to embodiment E.6, where the base is selected from the group consisting of LiOH, NaOH, KOH, diethylamine, triethylamine, tributylamine, diisopropylethylamine, dimethylisopropylamine, ethyl-tert-butylamine, isopropyl-tert-butylamine, (2-methoxyethyl)methylamine, N,N-dicyclohexylmethylamine, N-cyclohexyldimethylamine, N,N,N',N'-tetramethylethylenediamine, N,N,N',N'-tetramethylpropylene-1,3-diamine, piperdine, N-methylpiperidine, 2,2,6,6-tetramethylpiperidine, N-methyl-2,6,6-tetramethylpiperidine, N-methyl-4-hydroxy-2,2,6,6-tetramethylpiperidine, morpholine and N-methylmorpholine, where the bases can be used in supported from (i.e. on a support material).

E.8. The method according to embodiment E.6, where the base is selected from the group consisting of amines of the formula $NR^1R^2R^3$, where $R^1$, $R^2$ and $R^3$, independently of each other, are selected from the group consisting of hydrogen and $C_1$-$C_6$-alkyl, where at least one of $R^1$, $R^2$ and $R^3$ is $C_1$-$C_6$-alkyl.

E.9. The method according to any of embodiment E.7 or E.8, where the base is selected from the group consisting of triethylamine, tributylamine and diisopropylethylamine.

E.10. The method according to any of the preceding embodiments, where formic acid is used as reduction agent in step (a), where formic acid and the base are used in a molar ratio of from 100:1 to 1:10.

E.11. The method according to embodiment E.10, where formic acid and the base are used in a molar ratio of from 10:1 to 1:5.

E.12. The method according to embodiment E.11 where formic acid and the base are used in a molar ratio of from 10:1 to 1:2, E.13. The method according to embodiment E.12, where formic acid and the base are used in a molar ratio of 5:1 to 1:1.

E.14. The method according to any of the preceding embodiments, where the compound 1 and the reduction agent are used in a molar ratio of from 1:1 to 1:10.

E.15. The method according to embodiment E.14, where the compound 1 and the reduction agent are used in a molar ratio of from 1:1 to 1:5.

E.16. The method according to any of the preceding embodiments, where in the chiral transition metal catalyst one or more chiral ligands are coordinatively bound to the central transition metal.

E.17. The method according to any of the preceding embodiments, where the chiral transition metal catalyst used in step (a) is selected from group VIII metal catalysts.

E.18. The method according to embodiment E.17, where the chiral transition metal catalyst is selected from group 8 and 9 metal catalysts.

E.19. The method according to embodiment E.18, where the chiral transition metal catalyst is selected from Ru, Rh and Ir catalysts E.20. The method according to embodiment E.19, where the chiral transition metal catalyst is selected from Rh and Ir catalysts.

E.21. The method according to any of the preceding embodiments, where the chiral transition metal catalyst, calculated on the basis of the transition metal content, is used in an amount of from 0.01 to 10 mol %, relative to 1 mol of the compound 1.

E.22. The method according to embodiment E.21, where the chiral transition metal catalyst, calculated on the basis of the transition metal content, is used in an amount of from 0.05 to 5 mol-%, relative to 1 mol of the compound 1.

E.23. The method according to embodiment E.22, where the chiral transition metal catalyst, calculated on the basis of the transition metal content, is used in an amount of from 0.1 to 5 mol-%, e.g. 0.1 to 2 mol-%, relative to 1 mol of the compound 1.

E.24. The method according to any of the preceding embodiments, where the chiral transition metal catalyst is either preformed and contains one or more chiral ligands coordinated to the transition metal; or is formed in situ by reaction of a transition metal precursor compound and one or more chiral ligands.

E.25. The method according to embodiment E.24, where the chiral ligands are selected from the group consisting of bidentate amine-based chiral ligands.

E.26. The method according to embodiment E.25, where the chiral ligands are selected from the group consisting of chiral 1,2-diphenyl-ethylene-1,2-diamines, 1,2-cyclohexanediamines, and 1,2-bis(methylamino)cyclohexanes.

E.27. The method according to embodiment E.26, where the chiral ligands are selected from the group consisting of chiral 1,2-diphenyl-ethylene-1,2-diamines.

E.28. The method according to embodiment E.27, where the chiral ligands are selected from the group consisting of the chiral forms of 1,2-diphenyl-ethylene-1,2-diamines of the formula (II)

(II)

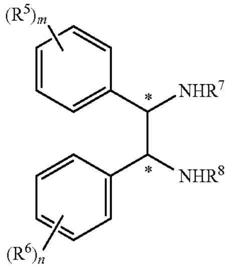

where the asterisk shows the stereogenic centers;

$R^5$ and $R^6$, independently of each other, are selected from the group consisting of OH, halogen, $C_1$-$C_4$-alkyl and $C_1$-$C_4$-alkoxy;

$R^7$ and $R^8$, independently of each other, are selected from the group consisting of hydrogen, $C_1$-$C_4$-alkyl, -L-phenyl, where the phenyl ring may carry 1, 2, 3, 4 or 5 substituents selected from the group consisting of $C_1$-$C_4$-alkyl, $C_1$-$C_4$-haloalkyl and $C_1$-$C_4$-alkoxy; and $SO_2R^9$;

L is a linker selected from the group consisting of $C_2$-$C_6$-alkylene, $C_1$-$C_3$-alkylene-O—$(CH_2)_p$, where p is 0, 1 or 2; and $C_1$-$C_3$-alkylene-(1,2-phenylene)-$(CH_2)_r$, where r is 0, 1 or 2;

$R^9$ is selected from the group consisting of $C_1$-$C_4$-alkyl, $C_1$-$C_4$-haloalkyl, phenyl, phenyl-$C_1$-$C_3$-alkyl, where phenyl in the two aforementioned radicals may carry 1, 2, 3, 4 or 5 substituents selected from the group consisting of halogen, $C_1$-$C_4$-alkyl, $C_1$-$C_4$-haloalkyl and $C_1$-$C_4$-alkoxy; naphthyl, $C_6$-$C_{10}$-bicycloalkyl-$C_1$-$C_3$-alkyl, where the bicycloalkyl ring may be substituted by 1, 2, 3, 4 or 5 substituents selected from the group consisting of $C_1$-$C_4$-alkyl and oxo; and $NR^{10}R^{11}$;

$R^{10}$ is hydrogen or $C_1$-$C_4$-alkyl;

$R^{11}$ is phenyl-$C_1$-$C_3$-alkyl, where the phenyl ring may carry 1, 2, 3, 4 or 5 substituents selected from the group consisting of halogen, $C_1$-$C_4$-alkyl, $C_1$-$C_4$-haloalkyl and $C_1$-$C_4$-alkoxy; and m and n, independently of each other, are 0, 1, 2, 3, 4 or 5.

E.29. The method according to embodiment E.28, where in compounds (II) $R^5$ and $R^6$ are $C_1$-$C_4$-alkoxy;

one of $R^7$ and $R^8$ is selected from the group consisting of hydrogen, $C_1$-$C_4$-alkyl and -L-phenyl, where phenyl may carry 1, 2, 3, 4 or 5 substituents selected from the group consisting of $C_1$-$C_4$-alkyl, $C_1$-$C_4$-haloalkyl and $C_1$-$C_4$-alkoxy; and the other of $R^7$ and $R^8$ is selected from the group consisting of hydrogen and $SO_2R^9$;

L is a linker selected from the group consisting of linear $C_3$-$C_6$-alkylene, $(CH_2)_o$—O—$(CH_2)_p$, where p and o are independently 1 or 2; and $(CH_2)_q$-(1,2-phenylene)-$(CH_2)_r$, where q and r are independently 0, 1 or 2, where at least one of q and r is not 0;

$R^9$ is selected from the group consisting of $C_1$-$C_4$-alkyl, $C_1$-$C_4$-haloalkyl, phenyl which may carry 1, 2, 3, 4 or 5 substituents selected from the group consisting of halogen, $C_1$-$C_4$-alkyl, $C_1$-$C_4$-haloalkyl and $C_1$-$C_4$-alkoxy; $C_7$-bicycloalkyl-methyl, where the bicycloalkyl ring may be substituted by 1, 2 or 3 substituents selected from the group consisting of $C_1$-$C_4$-alkyl and oxo; and $NR^{10}R^{11}$;

$R^{10}$ is hydrogen or $C_1$-$C_4$-alkyl;

$R^{11}$ is phenyl-$(CH_2)_s$-alkyl, where s is 2 or 3 and where the phenyl ring may carry 1, 2, 3, 4 or 5 substituents selected from the group consisting of halogen, $C_1$-$C_4$-alkyl, $C_1$-$C_4$-haloalkyl and $C_1$-$C_4$-alkoxy; and m and n are both 0 or are both 1; and are preferably both 0.

E.30. The method according to any of embodiments E.28 or E.29, where the chiral ligands are selected from the group consisting of the (1R,2R) or (1S,2S) forms of DPEN, TsDPEN, $CF_3$TsDPEN, MsDPEN, MeMsDPEN, MeTsDPEN, FsDPEN, TripsMesitylDPEN, CsDPEN, MesitylDPEN, RsDPEN, TsDiOMeDPEN and of a compound of the formula (II), wherein $R^7$ is $SO_2R^9$, where $R^9$ is $C_1$-$C_4$-alkyl or phenyl which may carry 1, 2 or 3 substituents selected from the group consisting of $C_1$-$C_4$-alkyl and $C_1$-$C_4$-haloalkyl, $R^8$ is —$(CH_2)_3$-phenyl or —$(CH_2)_4$-phenyl, where phenyl in the two last-mentioned radicals may carry 1, 2 or 3 substituents selected from the group consisting of $C_1$-$C_4$-alkyl, $C_1$-$C_4$-haloalkyl and $C_1$-$C_4$-alkoxy; and m and n are 0;

E.31. The method according to embodiment E.30, where the chiral ligands are selected from the group consisting of the (1R,2R) or (1S,2S) forms of TsDPEN, $CF_3$TsDPEN, MsDPEN, MeMsDPEN, MeTsDPEN, CsDPEN, MesitylDPEN, RsDPEN, TsDiOMeDPEN and of a compound of the formula (II), wherein $R^7$ is $SO_2R^9$, where $R^9$ is $C_1$-$C_4$-alkyl or phenyl which may carry 1, 2 or 3 substituents selected from the group consisting of $C_1$-$C_4$-alkyl and $C_1$-$C_4$-haloalkyl, $R^8$ is —$(CH_2)_3$-phenyl or —$(CH_2)_4$-phenyl; and m and n are 0.

E.32. The method according to embodiment E.31, where the chiral ligands are selected from the group consisting of the (1R,2R) or (1S,2S) forms of TsDPEN, MsDPEN and CsDPEN.

E.33. The method according to embodiment E.30, where the chiral transition metal catalysts are catalysts containing Ru, Rh or Ir as central metal and at least one ligand selected from the group consisting of the (1R, 2R) or (1S,2S) forms of DPEN, TsDPEN, $CF_3$TsDPEN, MsDPEN, MeMsDPEN, MeTsDPEN, FsDPEN, TripsMesitylDPEN, CsDPEN, MesitylDPEN, RsDPEN, TsDiOMeDPEN and of a compound of the formula (II), wherein $R^7$ is $SO_2R^9$, where $R^9$ is $C_1$-$C_4$-alkyl or phenyl which may carry 1, 2 or 3 substituents selected from the group consisting of $C_1$-$C_4$-alkyl and $C_1$-$C_4$-haloalkyl, $R^8$ is —$(CH_2)_3$-phenyl or —$(CH_2)_4$-phenyl, where phenyl in the two last-mentioned radicals may carry 1, 2 or 3 substituents selected from the group consisting of $C_1$-$C_4$-alkyl, $C_1$-$C_4$-haloalkyl and $C_1$-$C_4$-alkoxy; and m and n are 0.

E.34. The method according to any of embodiment E.31 and E.33, where the chiral transition metal catalysts are catalysts containing Ru, Rh or Ir as central metal and at least one ligand selected from the group consisting of the (1R,2R) or (1S,2S) forms of TsDPEN, $CF_3$TsDPEN, MsDPEN, MeMsDPEN, MeTsDPEN, CsDPEN, MesitylDPEN, RsDPEN, TsDiOMeDPEN and of a compound of the formula (II), wherein $R^7$ is $SO_2R^9$, where $R^9$ is $C_1$-$C_4$-alkyl or phenyl which may carry 1, 2 or 3 substituents selected from the group consisting of $C_1$-$C_4$-alkyl and $C_1$-$C_4$-haloalkyl, $R^8$ is —$(CH_2)_3$-phenyl or —$(CH_2)_4$-phenyl; and m and n are 0.

E.35. The method according to embodiment E.33, where the chiral transition metal catalysts are catalysts containing Ru, Rh or Ir as central metal and at least one ligand selected from the group consisting of the (1R,2R) or (1S,2S) forms of DPEN, TsDPEN, $CF_3$TsDPEN, MsDPEN, MeMsDPEN, MeTsDPEN, FsDPEN, TripsMesitylDPEN, CsDPEN, MesitylDPEN, RsDPEN and TsDiOMeDPEN; or are a catalyst containing Ru as central metal and at least one ligand selected from the (1R,2R) or (1S,2S) forms of the compounds of the formula (II), wherein $R^7$ is $SO_2R^9$, where $R^9$ is $C_1$-$C_4$-alkyl or phenyl which may carry 1, 2 or 3 substituents selected from the group consisting of $C_1$-$C_4$-alkyl and $C_1$-$C_4$-haloalkyl, $R^8$ is —$(CH_2)_3$-phenyl or —$(CH_2)_4$-phenyl, where phenyl in the two last-mentioned radicals may carry 1, 2 or 3 substituents selected from the group consisting of $C_1$-$C_4$-alkyl, $C_1$-$C_4$-haloalkyl and $C_1$-$C_4$-alkoxy; and m and n are 0.

E.36. The method according to embodiment E.35, where the chiral transition metal catalysts are catalysts containing Ru, Rh or Ir as central metal and at least one chiral ligand selected from the group consisting of the (1R,2R) or (1S,2S) forms of TsDPEN, $CF_3$TsDPEN, MsDPEN, MeMsDPEN, MeTsDPEN, CsDPEN, Mesit-ylDPEN, RsDPEN and TsDiOMeDPEN; or are a catalyst containing Ru as central metal and at least one chiral ligand selected from the (1R,2R) or (1S,2S) forms of the compounds of the formula (II), wherein $R^7$ is $SO_2R^9$, where $R^9$ is $C_1$-$C_4$-alkyl or phenyl which may carry 1, 2 or 3 substituents selected from the group consisting of $C_1$-$C_4$-alkyl and $C_1$-$C_4$-haloalkyl, $R^8$ is —$(CH_2)_3$-phenyl or —$(CH_2)_4$-phenyl; and m and n are 0.

E.37. The method according to embodiment E.36, where the chiral transition metal catalysts are catalysts containing Ru, Rh or Ir as central metal and at least one chiral ligand selected from the group consisting of the (1R,2R) or (1S,2S) forms of TsDPEN, $CF_3$TsDPEN, MsDPEN, MeMsDPEN, MeTsDPEN, CsDPEN, Mesit-ylDPEN, RsDPEN and TsDiOMeDPEN; or are a catalyst of the following formula

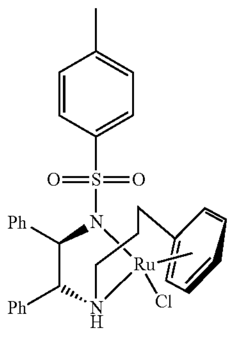

or

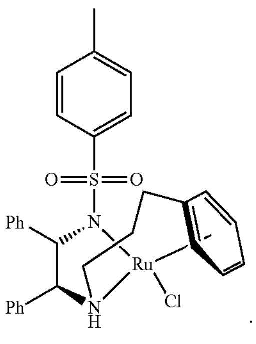

.

E.38. The method according to embodiment E.37, where the chiral transition metal catalysts are catalysts containing Ru, Rh or Ir as central metal and a chiral ligand selected from the group consisting of the (1R,2R) or (1S,2S) forms of TsDPEN, MeMsDPEN and CsDPEN.

E.39. The method according to any of embodiments E.28 to E.31 and E.33 to E.37, where in case that none of $R^7$ and $R^8$ is -L-phenyl or $SO_2R^9$ with $R^9$ being phenyl-$C_1$-$C_3$-alkyl or $NR^{10}R^{11}$, the catalyst contains additionally a ligand selected from aromatic rings.

E.40. The method according to embodiment E.39, where the aromatic rings are selected from the group consisting of Cp, Cp*, benzene, p-cymene, mesitylene and hexamethylbenzene.

E.41. The method according to embodiment E.40 where the aromatic rings are selected from the group consisting of Cp*, benzene, p-cymene, mesitylene and hexamethylbenzene, E.42. The method according to embodiment E.41, where the aromatic rings are selected from the group consisting of Cp*, p-cymene and mesitylene.

E.43. The method according to embodiment E.42, where the central metal is Rh or Ir and the aromatic ring is Cp*, or the central metal is Ru and the aromatic ring is p-cymene or mesitylene.

E.44. The method according to any of the preceding embodiments, where the chiral transition metal catalyst additionally contains one or two halogen or sulfonate ligands.

E.45. The method according to embodiment E.44, where chiral transition metal catalyst additionally contains one or two halogen ligands.

E.46. The method according to embodiment E.45, where chiral transition metal catalyst additionally contains one or two, preferably one, Cl ligand(s).

E.47. The method according to any of embodiments E.38 to E.46, where the chiral transition metal catalysts are catalysts containing Ru, Rh or Ir as central metal, a chiral ligand selected from the group consisting of the (1R,2R) or (1S,2S) forms of TsDPEN, MeMsDPEN and CsDPEN, a ligand selected from the group consisting of Cp*, p-cymene and mesitylene, and a halogen or sulfonate ligand, preferably a Cl ligand.

E.48. The method according to any of the preceding embodiments, for preparing in step (a) 2-[(2S)-2-(2-chlorothiazol-5-yl)-2-hydroxy-ethyl]sulfanyl-6-hydroxy-3-methyl-5-phenyl-pyrimidin-4-one of the formula 2-S

2-S

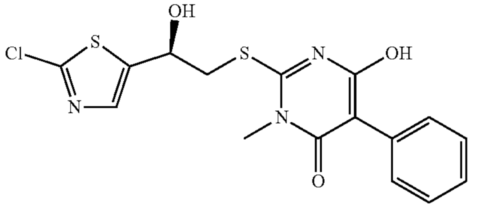

in an enantiomeric excess of at least 55% ee.

E.49. The method according to embodiment E.48, for preparing 2-[(2S)-2-(2-chlorothiazol-5-yl)-2-hydroxy-ethyl]sulfanyl-6-hydroxy-3-methyl-5-phenyl-pyrimidin-4-one of the formula 2-S in an enantiomeric excess of at least 60% ee.

E.50. The method according to embodiment E.49, for preparing 2-[(2S)-2-(2-chlorothiazol-5-yl)-2-hydroxy-ethyl]sulfanyl-6-hydroxy-3-methyl-5-phenyl-pyrimidin-4-one of the formula 2-S in an enantiomeric excess of at least 70% ee.

E.51. The method according to embodiment E.50, for preparing 2-[(2S)-2-(2-chlorothiazol-5-yl)-2-hydroxy-ethyl]sulfanyl-6-hydroxy-3-methyl-5-phenyl-pyrimidin-4-one of the formula 2-S in an enantiomeric excess of at least 80% ee.

E.52. The method according to embodiment E.51, for preparing 2-[(2S)-2-(2-chlorothiazol-5-yl)-2-hydroxy-ethyl]sulfanyl-6-hydroxy-3-methyl-5-phenyl-pyrimidin-4-one of the formula 2-S in an enantiomeric excess of at least 90% ee.

E.53. The method according to any of embodiments E.48 to E.52, where the chiral transition metal catalyst comprises a chiral ligand selected from the group consisting of (1S,2S)-DPEN, (1S,2S)-TsDPEN, (1S,2S)-$CF_3$TsDPEN, (1S,2S)-MsDPEN, (1S,2S)-MeMsDPEN, (1S,2S)-MeTsDPEN, (1S,2S)-FsDPEN, (1S,2S)-TripsMesitylDPEN, (1S,2S)-CsDPEN, (1S,2S)-MesitylDPEN, (1S,2S)-RsDPEN, (1S,2S)-Ts-DiOMeDPEN and the (1S,2S) form of a compound of the formula (II), wherein $R^7$ is $SO_2R^9$, where $R^9$ is $C_1$-$C_4$-alkyl or phenyl which may carry 1, 2 or 3 substituents selected from the group consisting of $C_1$-$C_4$-alkyl and $C_1$-$C_4$-haloalkyl, $R^8$ is —$(CH_2)_3$-phenyl or —$(CH_2)_4$-phenyl, where phenyl in the two last-mentioned radicals may carry 1, 2 or 3 substituents selected from the group consisting of $C_1$-$C_4$-alkyl, $C_1$-$C_4$-haloalkyl and $C_1$-$C_4$-alkoxy; and m and n are 0; and where the chiral ligand is preferably selected from the group consisting of (1S,2S)-TsDPEN, (1S,2S)-$CF_3$TsDPEN, (1S,2S)-MsDPEN, (1S,2S)-MeMsDPEN, (1S,2S)-MeTsDPEN, (1S,2S)-CsDPEN, (1S,2S)-MesitylDPEN, (1S,2S)-RsDPEN, (1S,2S)-Ts-DiOMeDPEN and the (1S,2S) form of a compound of the formula (II), wherein $R^7$ is $SO_2R^9$, where $R^9$ is $C_1$-$C_4$-alkyl or phenyl which may carry 1, 2 or 3 substituents selected from the group consisting of $C_1$-$C_4$-alkyl and $C_1$-$C_4$-haloalkyl, $R^8$ is —$(CH_2)_3$-phenyl or —$(CH_2)_4$-phenyl; and m and n are 0.

E.54. The method according to embodiment E.53, where the chiral ligand is selected from the group consisting of (1S,2S)-TsDPEN, (1S,2S)-MsDPEN and (1S,2S)-CsDPEN.

E.55. The method according to any of embodiments E.48 to E.54, where the chiral transition metal catalyst comprises as central metal Ru, Rh or Ir, and comprises a chiral ligand selected from the group consisting of (1S,2S)-DPEN, (1S,2S)-TsDPEN, (1S,2S)-$CF_3$TsDPEN, (1S,2S)-MsDPEN, (1S,2S)-MeMsDPEN, (1S,2S)-MeTsDPEN, (1S,2S)-FsDPEN, (1S,2S)-TripsMesitylDPEN, (1S,2S)-CsDPEN, (1S,2S)-MesitylDPEN, (1S,2S)-RsDPEN, (1S,2S)-Ts-DiOMeDPEN and the (1S,2S) form of a compound of the formula (II), wherein $R^7$ is $SO_2R^9$, where $R^9$ is $C_1$-$C_4$-alkyl or phenyl which may carry 1, 2 or 3 substituents selected from the group consisting of $C_1$-$C_4$-alkyl and $C_1$-$C_4$-haloalkyl, $R^8$ is —$(CH_2)_3$-phenyl or —$(CH_2)_4$-phenyl, where phenyl in the two last-mentioned radicals may carry 1, 2 or 3 substituents selected from the group consisting of $C_1$-$C_4$-alkyl, $C_1$-$C_4$-haloalkyl and $C_1$-$C_4$-alkoxy; and m and n are 0; where preferably the catalyst comprises as central metal Ru, Rh or Ir, and comprises a chiral ligand selected from the group consisting of (1S,2S)-TsDPEN, (1S,2S)-$CF_3$TsDPEN, (1S,2S)-MsDPEN, (1S,2S)-MeMsDPEN, (1S,2S)-MeTsDPEN, (1S,2S)-CsDPEN, (1S,2S)-MesitylDPEN, (1S,2S)-RsDPEN, (1S,2S)-Ts-DiOMeDPEN and the (1S,2S) form of a compound of the formula (II), wherein $R^7$ is $SO_2R^9$, where $R^9$ is $C_1$-$C_4$-alkyl or phenyl which may carry 1, 2 or 3 substituents selected from the group consisting of $C_1$-$C_4$-alkyl and $C_1$-$C_4$-haloalkyl, $R^8$ is —$(CH_2)_3$-phenyl or —$(CH_2)_4$-phenyl; and m and n are 0.

E.56. The method according to any of embodiments E.48 to E.55, where the chiral transition metal catalyst comprises as central metal Ru, Rh or Ir, and comprises a chiral ligand selected from the group consisting of (1S,2S)-DPEN, (1S,2S)-TsDPEN, (1S,2S)-$CF_3$TsDPEN, (1S,2S)-MsDPEN, (1S,2S)-MeMsDPEN, (1S,2S)-MeTsDPEN, (1S,2S)-FsDPEN, (1S,2S)-TripsMesitylDPEN, (1S,2S)-CsDPEN, (1S,2S)-MesitylDPEN, (1S,2S)-RsDPEN and (1S,2S)-Ts-DiOMeDPEN; or is a catalyst containing Ru as central metal and at least one ligand selected from the (1S,2S) form of compounds of the formula (II), wherein $R^7$ is $SO_2R^9$, where $R^9$ is $C_1$-$C_4$-alkyl or phenyl which may carry 1, 2 or 3 substituents selected from the group consisting of $C_1$-$C_4$-alkyl and $C_1$-$C_4$-haloalkyl, $R^8$ is —$(CH_2)_3$-phenyl or —$(CH_2)_4$-phenyl, where phenyl in the two last-mentioned radicals may carry 1, 2 or 3 substituents selected from the group consisting of $C_1$-$C_4$-alkyl, $C_1$-$C_4$-haloalkyl and $C_1$-$C_4$-alkoxy; and m and n are 0; where preferably the catalyst comprises as central metal Ru, Rh or Ir, and comprises a chiral ligand selected from the group consisting of (1S,2S)-TsDPEN, (1S,2S)-$CF_3$TsDPEN, (1S,2S)-MsDPEN, (1S,2S)-MeMsDPEN, (1S,2S)-MeTsDPEN, (1S,2S)-CsDPEN, (1S,2S)-MesitylDPEN, (1S,2S)-RsDPEN and (1S,2S)-TsDiOMeDPEN; or is a catalyst containing Ru as central metal and at least one ligand selected from the (1S,2S) form of compounds of the formula (II), wherein $R^7$ is $SO_2R^9$, where $R^9$ is $C_1$-$C_4$-alkyl or phenyl which may carry 1, 2 or 3 substituents selected from the group consisting of $C_1$-$C_4$-alkyl and $C_1$-$C_4$-haloalkyl, $R^8$ is —$(CH_2)_3$-phenyl or —$(CH_2)_4$-phenyl; and m and n are 0.

E.57. The method according to embodiment E.56, where the chiral transition metal catalyst comprises as central metal Ru, Rh or Ir, and comprises a chiral ligand selected from the group consisting of (1S,2S)-TsDPEN, (1S,2S)-$CF_3$TsDPEN, (1S,2S)-MsDPEN, (1S,2S)-MeMsDPEN, (1S,2S)-MeTsDPEN, (1S,2S)-CsDPEN, (1S,2S)-MesitylDPEN, (1S,2S)-RsDPEN and (1S,2S)-TsDiOMeDPEN; or is a catalyst of the following formula

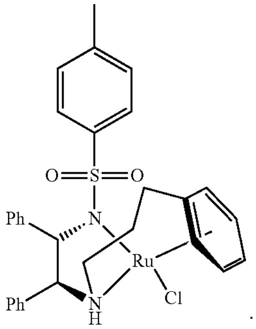

.

E.58. The method according to embodiment E.57, where the catalyst comprises as central metal Ru, Rh or Ir, and comprises a chiral ligand selected from the group consisting of (1S,2S)-TsDPEN, (1S,2S)-MsDPEN and (1S,2S)-CsDPEN.

E.59. The method according to any of embodiments E.1 to E.47, for preparing in step (a) 2-[(2R)-2-(2-chloro-thiazol-5-yl)-2-hydroxy-ethyl]sulfanyl-6-hydroxy-3-methyl-5-phenyl-pyrimidin-4-one of the formula 2-R

2-R

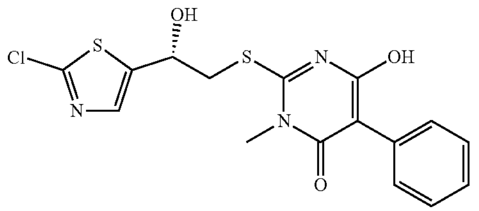

in an enantiomeric excess of at least 55% ee.

E.60. The method according to embodiment E.59, for preparing 2-[(2R)-2-(2-chlorothiazol-5-yl)-2-hydroxy-ethyl]sulfanyl-6-hydroxy-3-methyl-5-phenyl-pyrimidin-4-one of the formula 2-R in an enantiomeric excess of at least 60% ee.

E.61. The method according to embodiment E.60, for preparing 2-[(2R)-2-(2-chlorothiazol-5-yl)-2-hydroxy-ethyl]sulfanyl-6-hydroxy-3-methyl-5-phenyl-pyrimidin-4-one of the formula 2-R in an enantiomeric excess of at least 70% ee.

E.62. The method according to embodiment E.61, for preparing 2-[(2R)-2-(2-chlorothiazol-5-yl)-2-hydroxy-ethyl]sulfanyl-6-hydroxy-3-methyl-5-phenyl-pyrimidin-4-one of the formula 2-R in an enantiomeric excess of at least 80% ee.

E.63. The method according to embodiment E.62, for preparing 2-[(2R)-2-(2-chlorothiazol-5-yl)-2-hydroxy-ethyl]sulfanyl-6-hydroxy-3-methyl-5-phenyl-pyrimidin-4-one of the formula 2-R in an enantiomeric excess of at least 90% ee.

E.64. The method according to any of embodiments E.59 to E.63, where the chiral transition metal catalyst comprises a chiral ligand selected from the group consisting of (1R,2R)-DPEN, (1R,2R)-TsDPEN, (1R,2R)-$CF_3$TsDPEN, (1R,2R)-MsDPEN, (1R,2R)-MeMsDPEN, (1R,2R)-MeTsDPEN, (1R,2R)-FsDPEN, (1R,2R)-TripsMesitylDPEN, (1R,2R)-CsDPEN, (1R,2R)-MesitylDPEN, (1R,2R)-RsDPEN, (1R,2R)-Ts-DiOMeDPEN and the (1R,2R) form of a compound of the formula (II), wherein $R^7$ is $SO_2R^9$, where $R^9$ is $C_1$-$C_4$-alkyl or phenyl which may carry 1, 2 or 3 substituents selected from the group consisting of $C_1$-$C_4$-alkyl and $C_1$-$C_4$-haloalkyl, $R^8$ is $-(CH_2)_3$-phenyl or $-(CH_2)_4$-phenyl, where phenyl in the two last-mentioned radicals may carry 1, 2 or 3 substituents selected from the group consisting of $C_1$-$C_4$-alkyl, $C_1$-$C_4$-haloalkyl and $C_1$-$C_4$-alkoxy; and m and n are 0; where preferably the chiral ligand is selected from the group consisting of (1R,2R)-TsDPEN, (1R,2R)-$CF_3$TsDPEN, (1R,2R)-MsDPEN, (1R,2R)-MeMsDPEN, (1R,2R)-MeTsDPEN, (1R,2R)-CsDPEN, (1R,2R)-MesitylDPEN, (1R,2R)-RsDPEN, (1R,2R)-TsDiOMeDPEN and the (1R,2R) form of a compound of the formula (II), wherein $R^7$ is $SO_2R^9$, where $R^9$ is $C_1$-$C_4$-alkyl or phenyl which may carry 1, 2 or 3 substituents selected from the group consisting of $C_1$-$C_4$-alkyl and $C_1$-$C_4$-haloalkyl, $R^8$ is $-(CH_2)_3$-phenyl or $-(CH_2)_4$-phenyl; and m and n are 0.

E.65. The method according to embodiment E.64, where the chiral ligand is selected from the group consisting of (1R,2R)-TsDPEN, (1R,2R)-MsDPEN and (1R,2R)-CsDPEN.

E.66. The method according to any of embodiments E.59 to E.64, where the chiral transition metal catalyst comprises as central metal Ru, Rh or Ir, and comprises a chiral ligand selected from the group consisting of (1R,2R)-DPEN, (1R,2R)-TsDPEN, (1R,2R)-$CF_3$TsDPEN, (1R,2R)-MsDPEN, (1R,2R)-MeMsDPEN, (1R,2R)-MeTsDPEN, (1R,2R)-FsDPEN, (1R,2R)-TripsMesitylDPEN, (1R,2R)-CsDPEN, (1R,2R)-MesitylDPEN, (1R,2R)-RsDPEN, (1R,2R)-Ts-DiOMeDPEN and the (1R,2R) form of a compound of the formula (II), wherein $R^7$ is $SO_2R^9$, where $R^9$ is $C_1$-$C_4$-alkyl or phenyl which may carry 1, 2 or 3 substituents selected from the group consisting of $C_1$-$C_4$-alkyl and $C_1$-$C_4$-haloalkyl, $R^8$ is $-(CH_2)_3$-phenyl or $-(CH_2)_4$-phenyl, where phenyl in the two last-mentioned radicals may carry 1, 2 or 3 substituents selected from the group consisting of $C_1$-$C_4$-alkyl, $C_1$-$C_4$-haloalkyl and $C_1$-$C_4$-alkoxy; and m and n are 0; where preferably the catalyst comprises as central metal Ru, Rh or Ir, and comprises a chiral ligand selected from the group consisting of (1R,2R)-TsDPEN, (1R,2R)-$CF_3$TsDPEN, (1R,2R)-MsDPEN, (1R,2R)-MeMsDPEN, (1R,2R)-MeTsDPEN, (1R,2R)-CsDPEN, (1R,2R)-MesitylDPEN, (1R,2R)-RsDPEN, (1R,2R)-TsDiOMeDPEN and the (1R,2R) form of a compound of the formula (II), wherein $R^7$ is $SO_2R^9$, where $R^9$ is $C_1$-$C_4$-alkyl or phenyl which may carry 1, 2 or 3 substituents selected from the group consisting of $C_1$-$C_4$-alkyl and $C_1$-$C_4$-haloalkyl, $R^8$ is $-(CH_2)_3$-phenyl or $-(CH_2)_4$-phenyl; and m and n are 0.

E.67. The method according to any of embodiments E.59 to E.66, where the chiral transition metal catalyst comprises as central metal Ru, Rh or Ir, and comprises a chiral ligand selected from the group consisting of (1R,2R)-DPEN, (1R,2R)-TsDPEN, (1R,2R)-$CF_3$TsDPEN, (1R,2R)-MsDPEN, (1R,2R)-MeMsDPEN, (1R,2R)-MeTsDPEN, (1R,2R)-FsDPEN, (1R,2R)-TripsMesitylDPEN, (1R,2R)-CsDPEN, (1R,2R)-MesitylDPEN, (1R,2R)-RsDPEN and (1R,2R)-Ts-DiOMeDPEN, or is a catalyst containing Ru as central metal and at least one ligand selected from the (1R,2R) form of compounds of the formula (II), wherein $R^7$ is $SO_2R^9$, where $R^9$ is $C_1$-$C_4$-alkyl or phenyl which may carry 1, 2 or 3 substituents selected from the group consisting of $C_1$-$C_4$-alkyl and $C_1$-$C_4$-haloalkyl, $R^8$ is $-(CH_2)_3$-phenyl or $-(CH_2)_4$-phenyl, where phenyl in the two last-mentioned radicals may carry 1, 2 or 3 substituents selected from the group consisting of $C_1$-$C_4$-alkyl, $C_1$-$C_4$-haloalkyl and $C_1$-$C_4$-alkoxy; and m and n are 0; where preferably the catalyst comprises as central metal Ru, Rh or Ir, and comprises a chiral ligand selected from the group consisting of (1R,2R)-TsDPEN, (1R,2R)-$CF_3$TsDPEN, (1R,2R)-MsDPEN, (1R,2R)-MeMsDPEN, (1R,2R)-MeTsDPEN, (1R,2R)-CsDPEN, (1R,2R)-MesitylDPEN, (1R,2R)-RsDPEN and (1R,2R)-TsDiOMeDPEN, or is a catalyst containing Ru as central metal and at least one ligand selected from the (1R,2R) form of compounds of the formula (II), wherein $R^7$ is $SO_2R^9$, where $R^9$ is $C_1$-$C_4$-alkyl or phenyl which may carry 1, 2 or 3 substituents selected from the group consisting of $C_1$-$C_4$-alkyl and $C_1$-$C_4$-haloalkyl, $R^8$ is —$(CH_2)_3$-phenyl or —$(CH_2)_4$-phenyl; and m and n are 0.

E.68. The method according to embodiment E.67, where the chiral transition metal catalyst comprises as central metal Ru, Rh or Ir, and comprises a chiral ligand selected from the group consisting of (1R,2R)-TsDPEN, (1R,2R)-$CF_3$TsDPEN, (1R,2R)-MsDPEN, (1R,2R)-MeMsDPEN, (1R,2R)-MeTsDPEN, (1R,2R)-CsDPEN, (1R,2R)-MesitylDPEN, (1R,2R)-RsDPEN and (1R,2R)-TsDiOMeDPEN, or is a catalyst of the following formula:

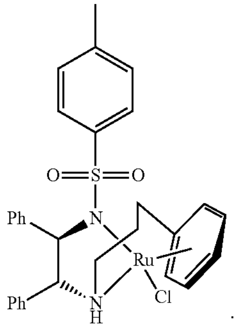

E.69. The method according to embodiment E.68, where the catalyst comprises as central metal Ru, Rh or Ir, and comprises a chiral ligand selected from the group consisting of (1R,2R)-TsDPEN, (1R,2R)-MsDPEN and (1R,2R)-CsDPEN.

E.70. The method according to any of the preceding embodiments, where the reaction in step (a) is carried out at a temperature of from −20 to 120° C.

E.71. The method according to embodiment E.70, where the reaction in step (a) is carried out at a temperature of from −15 to 25° C.

E.72. The method according to embodiment E.70, where the reaction in step (a) is carried out at a temperature of from 30 to 100° C.

E.73. The method according to embodiment E.72, where the reaction in step (a) is carried out at a temperature of from 50 to 90° C.

E.74. The method according to any of the preceding embodiments, where the reaction in step (a) and (b) is carried out in the presence of a solvent, E.75. The method according to embodiment E.74, where the solvent is selected from the group consisting of polar aprotic solvents, $C_1$-$C_4$-alkyl acetates, chlorinated alkanes, aromatic solvents, heterocyclic solvents, mixtures of the aforementioned solvents and mixtures of the aforementioned solvents with water;

where in case that formic acid and/or a base which is liquid at the reaction temperature is used, at least the reaction in step (a) can alternatively be carried out neat.

E.76. The method according to embodiment E.75, where the solvent is selected from the group consisting of dimethylformamide, diethylformamide, dibutylformamide, dimethylacetamide, tetrahydrofuran, 2-methyltetrahydrofuran, the dioxanes, dimethylsulfoxide, acetonitrile, N-methylpyrrolidone, N-(n-butyl)-pyrrolidone, N-(tert-butyl)-pyrrolidone, sulfolane, dimethylcarbonate, diethylcarbonate, propylene carbonate, γ-valerolactone, N,N,N',N'-tetrabutyl urea, 1,3-dimethyl-2-imidazolinone, ethyl acetate, isopropyl acetate, dichloromethane, trichloromethane, dichloroethane, benzene, toluene,α,α,α-trifluorotoluene (benzotrifluoride), the xylenes, fluorobenzene, chlorobenzene, dichlorobenzene, anisole (methoxybenzene), 4-formylmorpholine, dihydrolevoglucosenone (Cyrene®), mixtures of the aforementioned solvents and mixtures of the aforementioned solvents with up to 15% by weight, preferably up to 10% by weight, in particular up to 5% by weight, specifically up to 3% by weight of water, relative to the overall weight of the solvent.

E.77. The method according to embodiment E.76, where the solvent is selected from the group consisting of from dimethylformamide, dimethylacetamide, dichloromethane, trichloromethane, dichloroethane, α,α,α-trifluorotoluene (benzotrifluoride), fluorobenzene, chlorobenzene, dichlorobenzene, anisole (methoxybenzene) and mixtures thereof; in particular from dimethylformamide, dimethylacetamide and mixtures thereof.

E.78. The method according to any of the preceding embodiments, where during the reaction in step (a) an inert gas different from $CO_2$ is sparged through the reaction mixture; or where alternatively or additionally the reaction is carried out under reduced pressure.

E.79. The method according to embodiment E.78, where gas different from $CO_2$ is selected from the group consisting of argon, nitrogen, and mixtures of oxygen and nitrogen containing 1-8 vol-% of oxygen, relative to the total amount of the oxygen/nitrogen mixture.

E.80. The method according to embodiment E.79, where gas different from $CO_2$ is nitrogen.

E.81. The method according to any of the preceding embodiments, where the reaction in steps (a) and (b) is carried out in the presence of an additive selected from the group consisting of diethyl phosphite, borate esters and zinc salts, where the zinc salt are preferably selected from the group consisting of zinc halides, zinc acetate and zinc trifluoromethanesulfonate.

E.82. The method according to embodiment E.81, where the additive is diethyl phosphite or a zinc salt.

E.83. The method according to any of embodiments E.81 or E.82, where the additive is used in such an amount that the molar ratio of additive and the compound 1 is in the range of from 1:10000 to 10:1.

E.84. The method according to embodiment E.83, where the molar ratio of additive and the compound 1 is in the range of from 1:10000 to 5:1.

E.85. The method according to embodiment E.84, where the molar ratio of additive and the compound 1 is in the range of from 1:10000 to 2:1.

E.86. The method according to any of the preceding embodiments, where the activating agent used in step (b) is selected from the group consisting of $P(OR^1)_2Cl$, $P(OR^1)Cl_2$, $P(=O)(OR^1)_2Cl$, $P(=O)(OR^1)Cl_2$, where each $R^1$ in the four aforementioned compounds is independently $C_1$-$C_4$-alkyl; $PCl_3$, $P(=O)Cl_3$, polyphosphoric acid, $P_4O_{10}$, Mitsunobu-type reagents, triphenylphosphine in combination with a halogenating agent, $SO_3$ complexes with Lewis bases selected from amines, carboxamides and heteroaromatic compounds containing 1, 2 or 3 basic nitrogen ring atoms; $S(O)Cl_2$, $CH_3S(O)_2Cl$, carbonyldiimidazole (CDI), Vilsmeier reagent, complexes of N,N-dimethylformamide and/or N,N-dimethylacetamide with a Lewis acid; and mixtures of two or more of the aforementioned activating agents.

E.87. The method according to embodiment E.86, where the activating agent used in step (b) is selected from the group consisting of $P(OR^1)_2Cl$, $P(OR^1)Cl_2$, $P(=O)(OR^1)_2Cl$, where each $R^1$ in the three aforementioned compounds is independently $C_1$-$C_4$-alkyl; $PCl_3$, $P(O)Cl_3$, $SO_3$/dimethyl formamide complex, $SOCl_2$, $CH_3S(=O)_2Cl$, CDI and Mitsunobu-type reagents; and in particular from $P(OR^1)_2Cl$, where each $R^1$ is independently $C_1$-$C_4$-alkyl; and $PCl_3$.

E.88. The method according to embodiment E.87, where the activating agent used in step (b) is selected from the group consisting of dimethyl chlorophosphite ($P(OCH_3)_2Cl$), diethyl chlorophosphite ($P(OCH_2CH_3)_2Cl$), methyl dichlorophosphite ($P(OCH_3)Cl_2$), ethyl dichlorophosphite ($P(OCH_2CH_3)Cl_2$), $PCl_3$, $P(O)Cl_3$, $SOCl_2$, $CH_3S(=O)_2Cl$, CDI and Mitsunobu-type reagents; preferably from dimethyl chlorophosphite ($P(OCH_3)_2Cl$), diethyl chlorophosphite ($P(OCH_2CH_3)_2Cl$), methyl dichlorophosphite ($P(OCH_3)Cl_2$), ethyl dichlorophosphite ($P(OCH_2CH_3)Cl_2$), $PCl_3$, $P(O)Cl_3$, $CH_3S(=O)_2C_1$ and CDI.

E.89. The method according to embodiment E.88, where the activating agent used in step (b) is selected from the group consisting of dimethyl chlorophosphite ($P(OCH_3)_2Cl$), diethyl chlorophosphite ($P(OCH_2CH_3)_2Cl$), methyl dichlorophosphite ($P(OCH_3)Cl_2$), ethyl dichlorophosphite ($P(OCH_2CH_3)Cl_2$), $PCl_3$ and $P(O)Cl_3$, and in particular from dimethyl chlorophosphite ($P(OCH_3)_2Cl$), diethyl chlorophosphite ($P(OCH_2CH_3)_2Cl$) and $PCl_3$.

E.90. The method according to embodiment E.89, where the activating agent used in step (b) is selected from the group consisting of dimethyl chlorophosphite ($P(OCH_3)_2Cl$) and diethyl chlorophosphite ($P(OCH_2CH_3)_2Cl$).

E.91. The method according to any of the preceding embodiments, where the activating agent is used in such an amount that the molar ratio of the compound of the formula 1 and the activating agent is in the range of from 10:1 to 1:10.

E.92. The method according to embodiment E.91, where the activating agent is used in such an amount that the molar ratio of the compound of the formula 1 and the activating agent is in the range of from 2:1 to 1:5, preferably 1:1 to 1:4.

E.93. The method according to embodiment E.92, where the activating agent is used in such an amount that the molar ratio of the compound of the formula 1 and the activating agent is in the range of from 1:1 to 1:3.

E.94. The method according to embodiment E.93, where the activating agent is used in such an amount that the molar ratio of the compound of the formula 1 and the activating agent is in the range of from 1:1 to 1:2.

E.95. The method according to any of the preceding embodiments, where the reaction in step (b) is carried out at a temperature of from −80 to 120° C.

E.96. The method according to embodiment E.95, where the reaction in step (b) is carried out at a temperature of from −20 to 100° C.

E.97. The method according to embodiment E.96, where the reaction in step (b) is carried out at a temperature of from −10 to 90° C.

E.98. The method according to any of the preceding embodiments, for preparing (3R)-3-(2-chlorothiazol-5-yl)-8-methyl-7-oxo-6-phenyl-2,3-dihydrothiazolo[3,2-a]pyrimidin-4-ium-5-olate of the formula (I-R)

(I-R)

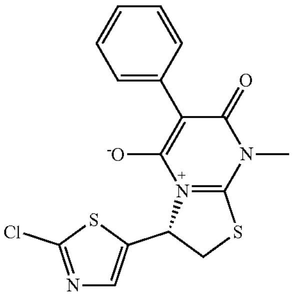

in an enantiomeric excess of at least 55% ee; which method comprises (a.1) reducing the compound of formula 1 so that a reaction mixture containing 2-[(2S)-2-(2-chlorothiazol-5-yl)-2-hydroxy-ethyl]sulfanyl-6-hydroxy-3-methyl-5-phenyl-pyrimidin-4-one of the formula 2-S

2-S

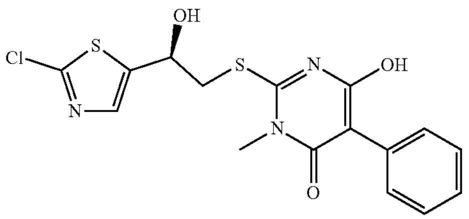

in an enantiomeric excess of at least 55% ee is formed; and (b.1) reacting the reaction mixture obtained in step (a.1) with an activating agent as defined in any of embodiments E.1 or E.86 to E.94.

E.99. The method according to embodiment E.98, for preparing (3R)-3-(2-chlorothiazol-5-yl)-8-methyl-7-oxo-6-phenyl-2,3-dihydrothiazolo[3,2-a]pyrimidin-4-ium-5-olate of the formula (I-R) in an enantiomeric excess of at least 60% ee, which method comprises (a.1) reducing the compound of formula 1 so that a reaction mixture containing 2-[(2S)-2-(2-chlorothiazol-5-yl)-2-hydroxy-ethyl]sulfanyl-6-hydroxy-3-methyl-5-phenyl-pyrimidin-4-one of the formula 2-S in an enantiomeric excess of at least 60% ee is formed; and (b.1) reacting the reaction mixture obtained in step (a.1) with an activating agent as defined in any of embodiments E.86 to E.94.

E.100. The method according to embodiment E.99, for preparing (3R)-3-(2-chlorothiazol-5-yl)-8-methyl-7-oxo-6-phenyl-2,3-dihydrothiazolo[3,2-a]pyrimidin-4-ium-5-olate of the formula (I-R) in an enantiomeric excess of at least 70% ee, which method comprises (a.1) reducing the compound of formula 1 so that a reaction mixture containing 2-[(2S)-2-(2-chlorothiazol-5-yl)-2-hydroxy-ethyl]sulfanyl-6-hydroxy-3-methyl-5-phenyl-pyrimidin-4-one of the formula 2-S in an enantiomeric excess of at least 70% ee is formed; and (b.1) reacting the reaction mixture obtained in step (a.1) with an activating agent as defined in any of embodiments E.86 to E.94.

E.101. The method according to embodiment E.100, for preparing (3R)-3-(2-chlorothiazol-5-yl)-8-methyl-7-oxo-6-phenyl-2,3-dihydrothiazolo[3,2-a]pyrimidin-4-ium-5-olate of the formula (I-R) in an enantiomeric excess of at least 80% ee, which method comprises (a.1) reducing the compound of formula 1 so that a reaction mixture containing 2-[(2S)-2-(2-chlorothiazol-5-yl)-2-hydroxy-ethyl]sulfanyl-6-hydroxy-3-methyl-5-phenyl-pyrimidin-4-one of the formula 2-S in an enantiomeric excess of at least 80% ee is formed; and (b.1) reacting the reaction mixture obtained in step (a.1) with an activating agent as defined in any of embodiments E.86 to E.94.

E.102. The method according to embodiment E.101, for preparing (3R)-3-(2-chlorothiazol-5-yl)-8-methyl-7-oxo-6-phenyl-2,3-dihydrothiazolo[3,2-a]pyrimidin-4-ium-5-olate of the formula (I-R) in an enantiomeric excess of at least 90% ee, which method comprises (a.1) reducing the compound of formula 1 so that a reaction mixture containing 2-[(2S)-2-(2-chlorothiazol-5-yl)-2-hydroxy-ethyl]sulfanyl-6-hydroxy-3-methyl-5-phenyl-pyrimidin-4-one of the formula 2-S in an enantiomeric excess of at least 90% ee is formed; and (b.1) reacting the reaction mixture obtained in step (a.1) with an activating agent as defined in any of embodiments E.86 to E.94.

E.103. The method according to any of embodiments E.1 to E.97, for preparing (3S)-3-(2-chlorothiazol-5-yl)-8-methyl-7-oxo-6-phenyl-2,3-dihydrothiazolo[3,2-a]pyrimidin-4-ium-5-olate of the formula (I-S)

(I-S)

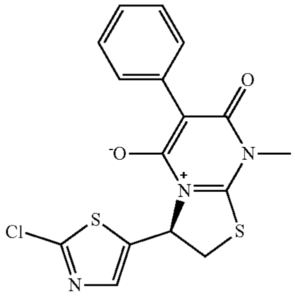

in an enantiomeric excess of at least 55% ee; which method comprises (a.2) reducing the compound of formula 1 so that a reaction mixture containing 2-[(2R)-2-(2-chlorothiazol-5-yl)-2-hydroxy-ethyl]sulfanyl-6-hydroxy-3-methyl-5-phenyl-pyrimidin-4-one of the formula 2-R

2-R

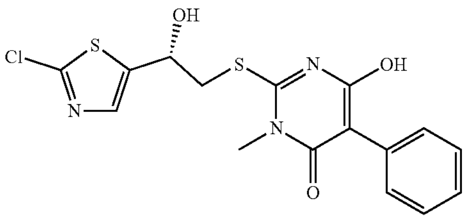

in an enantiomeric excess of at least 55% ee is formed; and (b.2) reacting the reaction mixture obtained in step (a.1) with an activating agent as defined in any of embodiments E.1 or E.86 to E.94.

E.104. The method according to embodiment E.103, for preparing (3S)-3-(2-chlorothiazol-5-yl)-8-methyl-7-oxo-6-phenyl-2,3-dihydrothiazolo[3,2-a]pyrimidin-4-ium-5-olate of the formula (I-S) in an enantiomeric excess of at least 60% ee, which method comprises (a.2) reducing the compound of formula 1 so that a reaction mixture containing 2-[(2R)-2-(2-chlorothiazol-5-yl)-2-hydroxy-ethyl]sulfanyl-6-hydroxy-3-methyl-5-phenyl-pyrimidin-4-one of the formula 2-R in an enantiomeric excess of at least 60% ee is formed; and (b.2) reacting the reaction mixture obtained in step (a.1) with an activating agent as defined in any of embodiments E.86 to E.94.

E.105. The method according to embodiment E.104, for preparing (3S)-3-(2-chlorothiazol-5-yl)-8-methyl-7-oxo-6-phenyl-2,3-dihydrothiazolo[3,2-a]pyrimidin-4-ium-5-olate of the formula (I-S) in an enantiomeric excess of at least 70% ee, which method comprises (a.2) reducing the compound of formula 1 so that a reaction mixture containing 2-[(2R)-2-(2-chlorothiazol-5-yl)-2-hydroxy-ethyl]sulfanyl-6-hydroxy-3-methyl-5-phenyl-pyrimidin-4-one of the formula 2-R in an enantiomeric excess of at least 70% ee is formed; and (b.2) reacting the reaction mixture obtained in step (a.1) with an activating agent as defined in any of embodiments E.86 to E.94.

E.106. The method according to embodiment E.105, for preparing (3S)-3-(2-chlorothiazol-5-yl)-8-methyl-7-oxo-6-phenyl-2,3-dihydrothiazolo[3,2-a]pyrimidin-4-ium-5-olate of the formula (I-S) in an enantiomeric excess of at least 80% ee, which method comprises (a.2) reducing the compound of formula 1 so that a reaction mixture containing 2-[(2R)-2-(2-chlorothiazol-5-yl)-2-hydroxy-ethyl]sulfanyl-6-hydroxy-3-methyl-5-phenyl-pyrimidin-4-one of the formula 2-R in an enantiomeric excess of at least 80% ee is formed; and (b.2) reacting the reaction mixture obtained in step (a.1) with an activating agent as defined in any of embodiments E.86 to E.94.

E.107. The method according to embodiment E.106, for preparing (3S)-3-(2-chlorothiazol-5-yl)-8-methyl-7-oxo-6-phenyl-2,3-dihydrothiazolo[3,2-a]pyrimidin-4-ium-5-olate of the formula (I-S) in an enantiomeric excess of at least 90% ee, which method comprises (a.2) reducing the compound of formula 1 so that a reaction mixture containing 2-[(2R)-2-(2-chlorothiazol-5-yl)-2-hydroxy-ethyl]sulfanyl-6-hydroxy-3-methyl-5-phenyl-pyrimidin-4-one of the formula 2-R in an enantiomeric excess of at least 90% ee is formed; and (b.2) reacting the reaction mixture obtained in step (a.1) with an activating agent as defined in any of embodiments E.86 to E.94.

The reaction sequence can be depicted as follows:

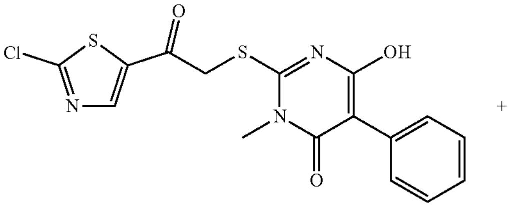

1

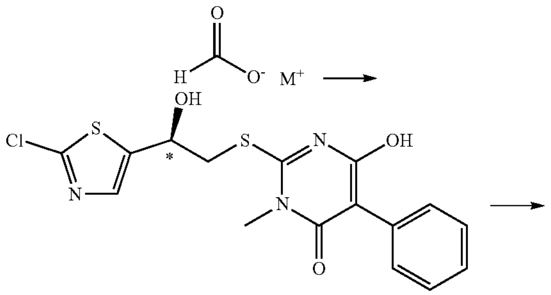

2

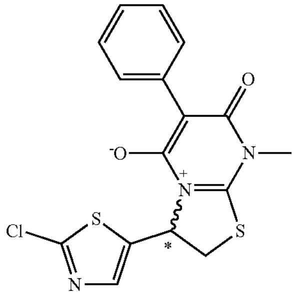

(I)

Here, only the formate is shown as reduction agent, but formic acid (in the presence of a base) or a mixture of formic acid and a formate (optionally in the presence of a base) can be used alternatively.

The reaction in step (a) can be classified as an asymmetric transfer hydrogenation. The reaction in step (b) can be classified as an intramolecular $S_N$ reaction.

$M^+$ is preferably selected from the group consisting of alkali metal cations, ammonium cations of the formula $[NHR^1R^2R^3]^+$, where $R^1$, $R^2$ and $R^3$, independently of each other, are selected from the group consisting of hydrogen, $C_1$-$C_6$-alkyl, $C_3$-$C_6$-cycloalkyl, $C_1$-$C_4$-alkoxy and $C_1$-$C_4$-alkoxy-$C_1$-$C_4$-alkyl, protonated diamines of the formula $NR^1R^2$-A-$NR^3R^4$, where $R^1$, $R^2$, $R^3$ and $R^4$, independently of each other, are selected from the group consisting of hydrogen, $C_1$-$C_6$-alkyl, $C_3$-$C_6$-cycloalkyl, $C_1$-$C_4$-alkoxy and $C_1$-$C_4$-alkoxy-$C_1$-$C_4$-alkyl, and A is $(CH_2)_2$ or $(CH_2)_3$; and protonated 5- or 6-membered saturated heterocyclic rings containing one nitrogen atom as ring member and optionally one further heteroatom selected from N and O as ring member, where the ring may carry 1 to 6 $C_1$-$C_4$-alkyl groups and/or 1 or 2 OH groups.

In the ammonium cations of the formula $[NHR^1R^2R^3]^+$ derived from monoamines, preferably at most one of $R^1$, $R^2$ and $R^3$ is hydrogen and the other two or all three thereof, independently of each other, are selected from the group consisting of hydrogen, $C_1$-$C_6$-alkyl, $C_3$-$C_6$-cycloalkyl and $C_1$-$C_4$-alkoxy-$C_1$-$C_4$-alkyl. Such ammonium cations are the protonated form of the corresponding amines $NR^1R^2R^3$. In the diamines $NR^1R^2$-A-$NR^3R^4$, preferably at least one of $R^1$, $R^2$, $R^3$ and $R^4$ is not hydrogen. More preferably, none of $R^1$, $R^2$, $R^3$ and $R^4$ is hydrogen. Preferably, $R^1$, $R^2$, $R^3$ and $R^4$ are independently of each other $C_1$-$C_4$-alkyl.

Protonated diamines $NR^1R^2$-A-$NR^3R^4$ can be monoprotonated ($[NHR^1R^2\text{-A-}NR^3R^4]^+$) or bisprotonated ($[NHR^1R^2\text{-A-}NHR^3R^4]^{2+}$). In the latter case, $M^+$ is more precisely depicted as $(M^{2+})_{1/2}$ or ($[N\ H\ R^1R^2\text{-A-}N\ H\ R^3R^4]^{2+})_{1/2}$.

The protonated 5- or 6-membered saturated heterocyclic rings are preferably derived from pyrrolidine, pyrazolidine, imidazolidine, oxazolidine, isoxazolidine, piperidine, piperazine, or morpholine. In case of two nitrogen ring atoms, like in pyrazolidine, imidazolidine or piperazine, the rings can also be bisprotonated. The protonated 5- or 6-membered saturated heterocyclic rings can carry 1 to 6 $C_1$-$C_4$-alkyl and/or 1 or 2 hydroxyl groups on the nitrogen and/or carbon ring atoms. Particularly, the protonated saturated heterocyclic rings are 6-membered and thus preferably derived from piperidine, piperazine, or morpholine, which may carry 1 to 6 $C_1$-$C_4$-alkyl and/or 1 or 2 hydroxyl groups on the nitrogen and/or carbon ring atoms.

In particular, $M^+$ is selected from the group consisting of $Li^+$, $Na^+$, $K^+$, $Cs^+$, $NH_4^+$, $[NH_2(C_2H_5)_2]^+$, $[NH(C_2H_5)_3]^+$, $[NH(CH_2CH_2CH_2CH_3)_3]^+$, $[NH(C_2H_5)(CH(CH_3)_2]^+$, $[NH(CH_3)_2(CH(CH_3)]^+$, $[NH_2(C_2H_5)(C(CH_3)_3]^+$, $[NH_2(CH(CH_3)_2)(C(CH_3)_3]^+$, $[NH_2(C_2H_4OCH_3)(CH_3)]^+$, $[NH(\text{cyclohexyl})_2(CH_3)]^+$, $[NH(\text{cyclohexyl})(CH_3)_2]^+$, protonated N,N,N',N'-tetramethylethylenediamine, protonated N,N,N',N'-tetramethylpropylene-1,3-diamine, protonated piperdine, protonated N-methylpiperidine, protonated 2,2,6,6-tetramethylpiperidine, protonated N-methyl-2,6,6-tetramethylpiperidine, protonated N-methyl-4-hydroxy-2,2,6,6-tetramethylpiperidine, protonated morpholine, and protonated N-methylmorpholine. More particularly, $M^+$ is selected from the group consisting of alkali metal cations (such as $Li^+$, $Na^+$, $K^+$ or $Cs^+$) and ammonium cations of the formula $[NHR^1R^2R^3]^+$, where $R^1$, $R^2$ and $R^3$, independently of each other, are selected from the group consisting of hydrogen and $C_1$-$C_6$-alkyl, where preferably at least one, preferably at least two of $R^1$, $R^2$ and $R^3$ are $C_1$-$C_6$-alkyl (such as $[NH_2(C_2H_5)_2]^+$, $[NH(C_2H_5)_3]^+$, $[NH(CH_2CH_2CH_2CH_3)_3]^+$, $[NH(C_2H_5)(CH(CH_3)_2]^+$, $[NH(CH_3)_2(CH(CH_3)]^+$, $[NH_2(C_2H_5)(C(CH_3)_3]^+$, or $[NH_2(CH(CH_3)_2)(C(CH_3)_3]^+$). Specifically, $M^+$ is selected from the group consisting of $Na^+$, $K^+$, $[NH(C_2H_5)_3]^+$, $[NH(CH_2CH_2CH_2CH_3)_3]^+$ and $[NH(C_2H_5)(CH(CH_3)_2]^+$, more specifically from $Na^+$, $K^+$, $[NH(C_2H_5)_3]^+$, $[NH(CH_2CH_2CH_2CH_3)_3]^+$ and $[NH(C_2H_5)(CH(CH_3)_2]^+$, and very specifically from $[NH(C_2H_5)_3]^+$, $[NH(CH_2CH_2CH_2CH_3)_3]^+$ and $[NH(C_2H_5)(CH(CH_3)_2]^+$.

The reduction agent is selected from the group consisting of formic acid HC(═O)OH, formates of the formula $HC({=}O)O^-M^+$ and mixtures of formic acid HC(═O)OH and one or more formates of the formula $HC({=}O)O^-M^+$, where $M^+$ is a cation equivalent. If formic acid is used as reduction agent, the reaction is mandatorily carried out in the presence of a base. Depending on the amount of base, formic acid can be converted partially or completely to the corresponding formate in situ.

The formates of the formula $HC({=}O)O^-M^+$ and mixtures of formic acid HC(═O)OH and one or more formates of the formula $HC({=}O)O^-M^+$ can be used in the reaction either in preformed form or can be formed in situ by mixing formic acid with the corresponding base in the adequate molar ratio. For obtaining formates or mixtures of formic acid and a formate wherein $M^+$ is a metal cation, e.g. an alkali metal cation, formic acid is for example mixed with a metal hydroxide, e.g. an alkali metal hydroxide, or with a metal carbonate, e.g. an alkali metal carbonate. For obtaining formates or mixtures of formic acid and a formate wherein $M^+$ is an ammonium cation or a protonated diamine or a protonated heterocyclic ring as described above, formic acid is suitably mixed with the corresponding monoamine $NR^1R^2R^3$, diamine $NR^1R^2$-A-$NR^3R^4$ or the 5- or 6-membered saturated heterocyclic ring defined above.

In context of the present invention, the base optionally or mandatorily used is one different from the formate(s) $HC(=O)O^-M^+$.

The base which is optionally or mandatorily used, depending on the reduction agent, is preferably selected from the group consisting of alkali metal hydroxides, amines of the formula $NR^1R^2R^3$, where $R^1$, $R^2$ and $R^3$, independently of each other, are selected from the group consisting of hydrogen, $C_1$-$C_6$-alkyl, $C_3$-$C_6$-cycloalkyl, $C_1$-$C_4$-alkoxy and $C_1$-$C_4$-alkoxy-$C_1$-$C_4$-alkyl, where at least one of $R^1$, $R^2$ and $R^3$ is not hydrogen; diamines of the formula $NR^1R^2$-A-$NR^3R^4$, where $R^1$, $R^2$, $R^3$ and $R^4$, independently of each other, are selected from the group consisting of hydrogen, $C_1$-$C_6$-alkyl, $C_3$-$C_6$-cycloalkyl, $C_1$-$C_4$-alkoxy and $C_1$-$C_4$-alkoxy-$C_1$-$C_4$-alkyl, and A is $(CH_2)_2$ or $(CH_2)_3$; and a 5- or 6-membered saturated heterocyclic ring containing one nitrogen atom as ring member and optionally one further heteroatom selected from N and O as ring member, where the ring may carry 1 to 6 $C_1$-$C_4$-alkyl groups and/or 1 or 2 OH groups.

If a formate or a mixture of formic acid and formate is used as reduction agent, the base corresponds preferably to the cation $M^+$ in the formate; especially if $M^+$ is derived from a monoamine $NR^1R^2R^3$, a diamine $NR^1R^2$-A-$NR^3R^4$, or said 5- or 6-membered saturated heterocyclic ring.

More preferably, the base is selected from the group consisting of LiOH, NaOH, KOH, diethylamine, triethylamine, tributylamine, diisopropylethylamine, dimethylisopropylamine, ethyl-tert-butylamine, isopropyl-tert-butylamine, (2-methoxyethyl)methylamine, N,N-dicyclohexylmethylamine, N-cyclohexyldimethylamine, N,N,N',N'-tetramethylethylenediamine, N,N,N',N'-tetramethylpropylene-1,3-diamine, piperdine, N-methylpiperidine, 2,2,6,6-tetramethylpiperidine, N-methyl-2,6,6-tetramethylpiperidine, N-methyl-4-hydroxy-2,2,6,6-tetramethylpiperidine, morpholine and N-methylmorpholine, where the bases can be used in supported from (i.e. on a support material). Among these, preference is given to amines $NR^1R^2R^3$, where $R^1$, $R^2$ and $R^3$, independently of each other, are selected from the group consisting of hydrogen and $C_1$-$C_6$-alkyl, where at least one of $R^1$, $R^2$ and $R^3$ is $C_1$-$C_6$-alkyl, such as diethylamine, triethylamine, tributylamine, diisopropylethylamine, dimethylisopropylamine, ethyl-tert-butylamine, or isopropyl-tert-butylamine. Specifically, the base is selected from triethylamine, tributylamine and diisopropylethylamine.

Suitable support materials for bases/supported bases are for example silica ($SiO_2$) and organic polymers, such as polystyrene or acrylic ester based supports, for example polymers typically used in ion exchange resins, e.g. styrene (co)polymers containing sulfonic acid groups, specifically styrene-divinyl benzene copolymers containing sulfonic acid groups. Commercial examples for such ion exchanger supports are materials commercialized under the Lewatit® (Lanxess), Purolite® (The Purolite Company), Dowex® (Dow Chemical Company), Amberlite® (Rohm and Haas Company) or Amberlyst® (Rohm and Haas Company) brands.

If a formate $HC(=O)O^-M^+$ is used as only reduction agent, it is expedient to use this in admixture with water.

If a mixture of formic acid $HC(=O)OH$ and one or more formates of the formula $HC(=O)O^-M^+$ is used as reduction agent, formic acid and the formate(s) can be used in any mixing ratio. If however formic acid predominates substantially in the mixture (i.e. is present in an amount of at least 90 mol %), it is expedient to carry out the reaction in the presence of a base. In inversely the formate(s) predominate(s) substantially in the mixture (i.e. is present in an amount of at least 90 mol %), it is expedient to carry out the reaction in the presence of water.

Preferably, formic acid is used as a reduction agent. It is thus mandatory to carry out the reaction in the presence of a base.

Formic acid and the base are preferably used in a molar ratio of from 100:1 to 1:10, preferably from 10:1 to 1:5, in particular from 10:1 to 1:2, and specifically from 5:1 to 1:1.

Compound 1 and the reduction agent are preferably used in a molar ratio of from 1:1 to 1:10, more preferably from 1:1 to 1:5.

The chiral transition metal catalyst is preferably selected from group VIII metal catalysts. Group VIII metal catalysts refer to catalysts having a metal from group VIII of the periodic system of elements as central metal. Group VIII relates to the IUPAC group definition valid before 1985 and corresponds to groups 8, 9 and 10 of the current IUPAC group designation. Group 8 comprises Fe, Ru and Os, group 9 Co, Rh and Ir and group 10 Ni, Pd and Pt. Preference is given to group 8 and 9 metal catalysts. Among these, in turn, preference is given to Ru, Rh and Ir catalysts. Specifically, the chiral transition metal catalyst is one with Rh or Ir as central atom.

Preferably, the chiral transition metal catalyst, calculated on the basis of the transition metal content, is used in an amount of 0.01 to 10 mol %, more preferably from 0.05 to 5 mol-%, and in particular from 0.1 to 5 mol %, e.g. from 0.1 to 2 mol-%, relative to 1 mol of the compound 1.

Chirality of the chiral transition metal catalyst is preferably based on the presence of one or more chiral ligands coordinatively bound to the central transition metal.

The chiral transition metal catalyst can be used in preformed form. In the preformed catalyst, the central metal is coordinatively bound to one or more chiral ligands. Alternatively, the chiral transition metal catalyst is formed in situ by reaction of a transition metal precursor compound and one or more chiral ligands.

The chiral ligands are preferably selected from bidentate amine-based chiral ligands. Suitable bidentate amine-based chiral ligands are based on 1,2-ethylenediamine substituted thusly that at least one of the carbon atoms carrying the amino groups is asymmetric; i.e. is a stereogenic center. Preferably, one or both of the carbon atoms of the 1,2-ethylenediamine ligand carry a phenyl, naphthyl or cyclohexyl ring or the two carbon atoms are part of a ring system imparting chirality. More preferably, the chiral ligands are selected from the group consisting of chiral 1,2-diphenylethylene-1,2-diamines, 1,2-cyclohexanediamines, and 1,2-bis(methylamino)cyclohexanes.

Even more preferably, the chiral ligands are selected from the group consisting of chiral 1,2-diphenyl-ethylene-1,2-diamines, and in particular from the chiral forms of 1,2-diphenyl-ethylene-1,2-diamines of the formula (II)

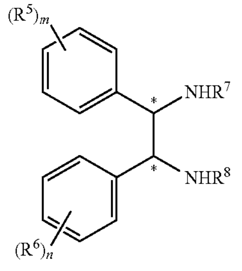

(II)

where the asterisk shows the stereogenic centers;

$R^5$ and $R^6$, independently of each other, are selected from the group consisting of OH, halogen, $C_1$-$C_4$-alkyl and $C_1$-$C_4$-alkoxy;

$R^7$ and $R^8$, independently of each other, are selected from the group consisting of hydrogen, $C_1$-$C_4$-alkyl, -L-phenyl, where the phenyl ring may carry 1, 2, 3, 4 or 5 substituents selected from the group consisting of $C_1$-$C_4$-alkyl, $C_1$-$C_4$-haloalkyl and $C_1$-$C_4$-alkoxy; and $SO_2R^9$;

L is a linker selected from the group consisting of $C_2$-$C_6$-alkylene, $C_1$-$C_3$-alkylene-O—$(CH_2)_p$, where p is 0, 1 or 2; and $C_1$-$C_3$-alkylene-(1,2-phenylene)-$(CH_2)_r$, where r is 0, 1 or 2;

$R^9$ is selected from the group consisting of $C_1$-$C_4$-alkyl, $C_1$-$C_4$-haloalkyl, phenyl, phenyl-$C_1$-$C_3$-alkyl, where phenyl in the two aforementioned radicals may carry 1, 2, 3, 4 or 5 substituents selected from the group consisting of halogen, $C_1$-$C_4$-alkyl, $C_1$-$C_4$-haloalkyl and $C_1$-$C_4$-alkoxy; naphthyl, $C_6$-$C_{10}$-bicycloalkyl-$C_1$-$C_3$-alkyl, where the bicycloalkyl ring may be substituted by 1, 2, 3, 4 or 5 substituents selected from the group consisting of $C_1$-$C_4$-alkyl and oxo; and $NR^{10}R^{11}$;

$R^{10}$ is hydrogen or $C_1$-$C_4$-alkyl;

$R^{11}$ is phenyl-$C_1$-$C_3$-alkyl, where the phenyl ring may carry 1, 2, 3, 4 or 5 substituents selected from the group consisting of halogen, $C_1$-$C_4$-alkyl, $C_1$-$C_4$-haloalkyl and $C_1$-$C_4$-alkoxy; and m and n, independently of each other, are 0, 1, 2, 3, 4 or 5.

Preferably, in compounds (II)

$R^5$ and $R^6$ are $C_1$-$C_4$-alkoxy;

one of $R^7$ and $R^8$ is selected from the group consisting of hydrogen, $C_1$-$C_4$-alkyl and -L-phenyl, where phenyl may carry 1, 2, 3, 4 or 5 substituents selected from the group consisting of $C_1$-$C_4$-alkyl, $C_1$-$C_4$-haloalkyl and $C_1$-$C_4$-alkoxy; and the other of $R^7$ and $R^8$ is selected from the group consisting of hydrogen and $SO_2R^9$;

L is a linker selected from the group consisting of linear $C_3$-$C_6$-alkylene, $(CH_2)_o$—O—$(CH_2)_p$, where p and o are independently 1 or 2; and $(CH_2)_q$-(1,2-phenylene)-$(CH_2)_r$, where q and r are independently 0, 1 or 2, where at least one of q and r is not 0;

$R^9$ is selected from the group consisting of $C_1$-$C_4$-alkyl, $C_1$-$C_4$-haloalkyl, phenyl which may carry 1, 2, 3, 4 or 5 substituents selected from the group consisting of halogen, $C_1$-$C_4$-alkyl, $C_1$-$C_4$-haloalkyl and $C_1$-$C_4$-alkoxy; $C_7$-bicycloalkyl-methyl, where the bicycloalkyl ring may be substituted by 1, 2 or 3 substituents selected from the group consisting of $C_1$-$C_4$-alkyl and oxo; and $NR^{10}R^{11}$;

$R^{10}$ is hydrogen or $C_1$-$C_4$-alkyl;

$R^{11}$ is phenyl-$(CH_2)_s$-alkyl, where s is 2 or 3 and where the phenyl ring may carry 1, 2, 3, 4 or 5 substituents selected from the group consisting of halogen, $C_1$-$C_4$-alkyl, $C_1$-$C_4$-haloalkyl and $C_1$-$C_4$-alkoxy; and m and n are both 0 or both 1, and are preferably both 0.

To be chiral, either both stereogenic centers (i.e. the carbon atoms marked in formula II with an asterisk) have to be in the R configuration or both have to be in the S configuration. If one is S and the other is R, an achiral meso system results.

Such ligands are known from Noyori-type asymmetric transfer hydrogenations and are generally commercially available. Preferred ligands of the formula (II) are the chiral forms (i.e. the (1S,2S) or (1R,2R) forms; positions 1 and 2 relate to the two carbon atoms marked in formula II with the asterisk which carry the phenyl rings and the amino groups) of DPEN, TsDPEN, $CF_3$TsDPEN, MsDPEN, MeMsDPEN, MeTsDPEN, FsDPEN, TripsMesitylDPEN, CsDPEN, MesitylDPEN, RsDPEN, TsDiOMeDPEN and of a compound of the formula (II), wherein $R^7$ is $SO_2R^9$, where $R^9$ is $C_1$-$C_4$-alkyl or phenyl which may carry 1, 2 or 3 substituents selected from the group consisting of $C_1$-$C_4$-alkyl and $C_1$-$C_4$-haloalkyl, $R^8$ is —$(CH_2)_3$-phenyl or —$(CH_2)_4$-phenyl, where phenyl in the two last-mentioned radicals may carry 1, 2 or 3 substituents selected from the group consisting of $C_1$-$C_4$-alkyl, $C_1$-$C_4$-haloalkyl and $C_1$-$C_4$-alkoxy; and m and n are 0. The acronyms correspond to following formulae:

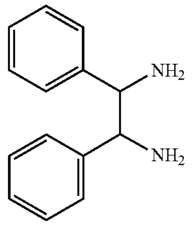

DPEN

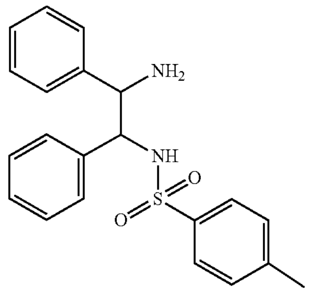

TsDPEN

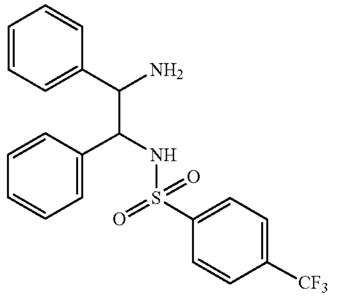

$CF_3$TsDPEN

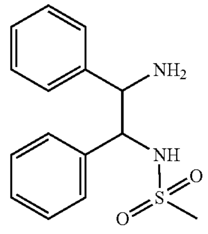

MsDPEN

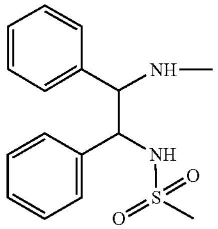

MeMsDPEN

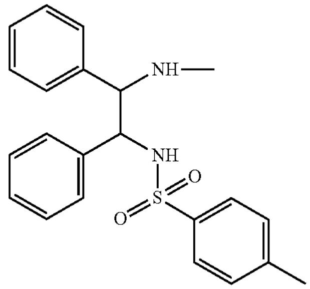

MeTsDPEN

-continued

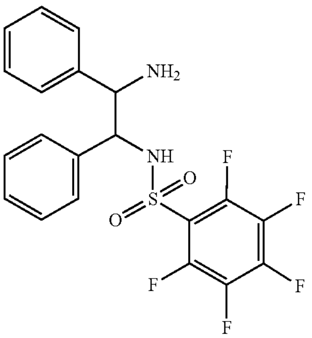

FsDPEN

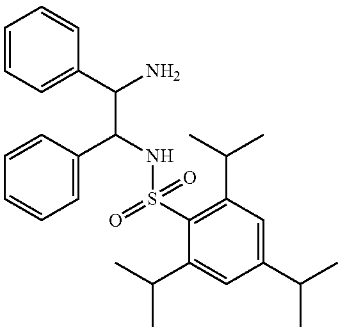

TripsMesitylDPEN

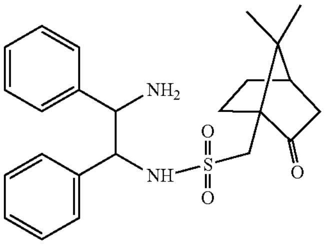

CsDPEN

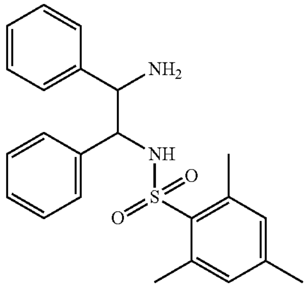

MesitylDPEN

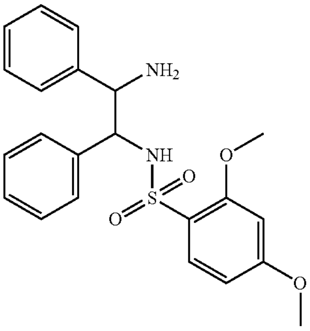

RsDPEN

-continued

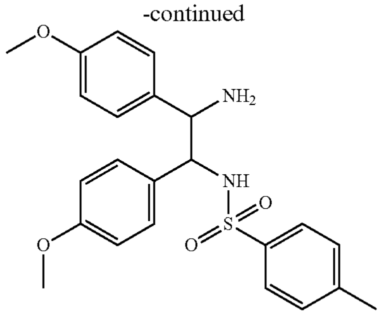

TsDiOMeDPEN

In addition to the two carbon atoms marked in formula II with the asterisk which carry the phenyl rings and the amino groups, CsDPEN has two further stereogenic centers in the camphor moiety (to be more precise on the norbornanone ring), namely at the carbon atoms which form the bridge points (positions 1 and 4; position 1 being the carbon ring atom bound to $—CH_2—SO_2—NH—$ . . . ). The stereochemistry of the camphor moiety does however not have a significant influence on the stereoselectivity of the hydrogenation reaction, so that CsDPEN derived from racemic camphor or from any of the camphor enantiomers (1S,4R or 1R,4S) or non-racemic mixtures of enantiomers can be used. In a specific embodiment, however, CsDPEN is derived from the 1S,4R enantiomer, i.e. specifically, N-[(1S,2S)-2-amino-1,2-diphenyl-ethyl]-1-[(1S,4R)-7,7-dimethyl-2-oxo-norbornan-1-yl]methanesulfonamide as (1S,2S)-CsDPEN and N-[(1R,2R)-2-amino-1,2-diphenyl-ethyl]-1-[(1S,4R)-7,7-dimethyl-2-oxo-norbornan-1-yl]methanesulfonamide as (1R,2R)-CsDPEN.

The chiral transition metal catalyst is in particular selected from catalysts containing Ru, Rh or Ir as central metal and at least one ligand selected from the group consisting of the (1R,2R) or (1S,2S) forms of DPEN, TsDPEN, $CF_3$TsDPEN, MsDPEN, MeMsDPEN, MeTsDPEN, FsDPEN, TripsMesitylDPEN, CsDPEN, MesitylDPEN, RsDPEN, TsDiOMeDPEN and of a compound of the formula (II), wherein $R^7$ is $SO_2R^9$, where $R^9$ is $C_1$-$C_4$-alkyl or phenyl which may carry 1, 2 or 3 substituents selected from the group consisting of $C_1$-$C_4$-alkyl and $C_1$-$C_4$-haloalkyl, $R^8$ is $—(CH_2)_3$-phenyl or $—(CH_2)_4$-phenyl, where phenyl in the two last-mentioned radicals may carry 1, 2 or 3 substituents selected from the group consisting of $C_1$-$C_4$-alkyl, $C_1$-$C_4$-haloalkyl and $C_1$-$C_4$-alkoxy; and m and n are 0. More particularly, the chiral transition metal catalyst is selected from catalysts containing Ru, Rh or Ir as central metal and at least one ligand selected from the group consisting of the (1R,2R) or (1S,2S) forms of TsDPEN, $CF_3$TsDPEN, MsDPEN, MeMsDPEN, MeTsDPEN, CsDPEN, MesitylDPEN, RsDPEN, TsDiOMeDPEN and of a compound of the formula (II), wherein $R^7$ is $SO_2R^9$, where $R^9$ is $C_1$-$C_4$-alkyl or phenyl which may carry 1, 2 or 3 substituents selected from the group consisting of $C_1$-$C_4$-alkyl and $C_1$-$C_4$-haloalkyl, $R^8$ is $—(CH_2)_3$-phenyl or $—(CH_2)_4$-phenyl, where phenyl in the two last-mentioned radicals may carry 1, 2 or 3 substituents selected from the group consisting of $C_1$-$C_4$-alkyl, $C_1$-$C_4$-haloalkyl and $C_1$-$C_4$-alkoxy; and m and n are 0.

Specifically, the chiral transition metal catalyst selected from catalysts containing Ru, Rh or Ir as central metal and at least one ligand selected from the group consisting of the (1R,2R) or (1S,2S) forms of DPEN, TsDPEN, $CF_3$TsDPEN, MsDPEN, MeMsDPEN, MeTsDPEN, FsDPEN, TripsMesitylDPEN, CsDPEN, MesitylDPEN, RsDPEN and TsDiOMeDPEN; and catalysts containing Ru as central metal and at least one ligand selected from the (1R,2R) or (1S,2S) form of compounds of the formula (II), wherein $R^7$ is $SO_2R^9$, where $R^9$ is $C_1$-$C_4$-alkyl or phenyl which may carry 1, 2 or 3 substituents selected from the group consisting of $C_1$-$C_4$-alkyl and $C_1$-$C_4$-haloalkyl, $R^8$ is —$(CH_2)_3$-phenyl or —$(CH_2)_4$-phenyl, where phenyl in the two last-mentioned radicals may carry 1, 2 or 3 substituents selected from the group consisting of $C_1$-$C_4$-alkyl, $C_1$-$C_4$-haloalkyl and $C_1$-$C_4$-alkoxy; and m and n are 0; and more specifically from catalysts containing Ru, Rh or Ir as central metal and at least one ligand selected from the group consisting of the (1R,2R) or (1S,2S) forms of TsDPEN, $CF_3$TsDPEN, MsDPEN, MeMsDPEN, MeTsDPEN, CsDPEN, MesitylDPEN, RsDPEN and TsDiOMeDPEN; and catalysts containing Ru as central metal and at least one ligand selected from the (1R,2R) or (1S,2S) form of compounds of the formula (II), wherein $R^7$ is $SO_2R^9$, where $R^9$ is $C_1$-$C_4$-alkyl or phenyl which may carry 1, 2 or 3 substituents selected from the group consisting of $C_1$-$C_4$-alkyl and $C_1$-$C_4$-haloalkyl, $R^8$ is —$(CH_2)_3$-phenyl or —$(CH_2)_4$-phenyl, where phenyl in the two last-mentioned radicals may carry 1, 2 or 3 substituents selected from the group consisting of $C_1$-$C_4$-alkyl, $C_1$-$C_4$-haloalkyl and $C_1$-$C_4$-alkoxy; and m and n are 0.

More specifically, the chiral transition metal catalyst selected from catalysts containing Ru, Rh or Ir as central metal and at least one ligand selected from the group consisting of the (1R,2R) or (1S,2S) forms of TsDPEN, $CF_3$TsDPEN, MsDPEN, MeMsDPEN, MeTsDPEN, CsDPEN, MesitylDPEN, RsDPEN and TsDiOMeDPEN; and a catalyst of the following formula

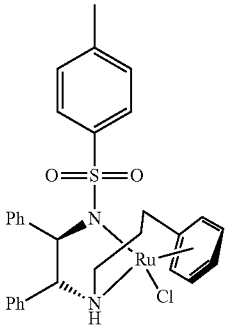

or

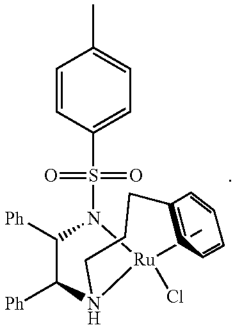

.

Very specifically, the chiral transition metal catalyst selected from catalysts containing Ru, Rh or Ir as central metal and at least one ligand selected from the group consisting of the (1R,2R) or (1S,2S) forms of TsDPEN, MsDPEN and CsDPEN.

The chiral transition metal catalyst generally contains just one of the aforementioned bidentate amine ligands.

The optionally substituted phenyl ring in -L-phenyl as a meaning of $R^7$ or $R^8$, the optionally substituted phenyl ring in phenyl-$C_1$-$C_3$-alkyl is as a meaning of $R^9$ and the optionally substituted phenyl ring in phenyl-$C_1$-$C_3$-alkyl as a meaning of $R^{11}$ generally acts as an additional (tethered) ligand for the central metal. Such complexes containing aromatic ligands tethered to an ethylene diamine ligand are generally known as Wills catalysts.

In case that none of $R^7$ and $R^8$ is -L-phenyl or $SO_2R^9$ with $R^9$ being phenyl-$C_1$-$C_3$-alkyl or $NR^{10}R^{11}$, the catalyst preferably contains additionally a ligand selected from aromatic rings. Such ligands have generally a higher hapticity, i.e. they coordinate to the metal center via more than one atom, and specifically via an uninterrupted and contiguous series of atoms. Generally, they act as $\eta^5$ or $\eta^6$ ligands. Typical aromatic $\eta^5$ and $\eta^6$ ligands are substituted or unsubstituted benzene and substituted or unsubstituted cyclopentadiene. The aromatic rings are preferably selected from Cp, Cp*, benzene, p-cymene, mesitylene and hexamethylbenzene, in particular from Cp*, benzene, p-cymene, mesitylene and hexamethylbenzene, and specifically from Cp*, p-cymene and mesitylene, and more specifically from Cp*. In tendency, 5-membered aromatic ligands, such as Cp and Cp* are better suited for Rh or Ir as central metal; and 6-membered aromatic ligands, such as benzene, p-cymene, mesitylene and hexamethylbenzene, are better suited for Ru as central metal. Thus, very specifically, the aromatic ring is Cp* if the central metal is Rh or Ir, and is p-cymene or mesitylene if the central metal is Ru.

Generally, the catalysts contain one or two further ligand of which at least one is replaced during reaction by a hydride ligand from the reduction agent under basic conditions. Generally, the further ligand is a halogen (e.g. Cl, Br or I; among which Cl is preferred) or a sulfonate (e.g. triflate, mesylate, tosylate or nonaflate; among which triflate is preferred) ligand, in particular a halogen ligand, specifically Cl.

Specifically, the chiral transition metal catalyst is selected from catalysts containing Ru, Rh or Ir as central metal, a chiral ligand selected from the group consisting of the (1R,2R) or (1S,2S) forms of TsDPEN, MsDPEN and CsDPEN, a ligand selected from halogen or sulfonate ligands, preferably from Cl, and a further ligand selected from Cp*, p-cymene and mesitylene.

Many of the above-described ligands and catalysts are commercially available or can be prepared by standard reactions starting from suitable catalyst precursors and ligands.

Catalyst precursors are generally salts of the central metal or complexes of the central metal with ligands different from the chiral ligand. In case of the preferably used catalysts with Ru, Rh or Ir as central metal, the catalyst precursor is specifically a binuclear complex containing an aromatic ring ligand and 2 halogen ligands. Non-exhaustive examples are $[Ru(para\text{-}cymene)Cl_2]_2$, $[Ru(mesitylene)Cl_2]_2$, $[Rh(III)Cl_2Cp^*]_2$, or $[Ir(III)Cl_2Cp^*]_2$. Such complexes are generally commercially available or can be prepared by standard methods.

Preformed catalysts are generally prepared by mixing the catalyst precursor with the chiral ligand. The reaction is generally carried out in a solvent. Depending on the catalyst precursor, it might be useful to carry out the reaction in the presence of a base. For instance, if the above-mentioned binuclear complexes of Ru, Rh or Ir containing an aromatic ring ligand and 2 halogen ligands are used as precursor compounds, the presence of a base is useful to ease or allow the reaction, i.e. the conversion of the binuclear complex into a mononuclear complex containing the desired chiral ligand.

The catalyst precursor and the chiral ligand are generally mixed in a molar ratio of from 2:1 to 1:5, preferably 1.5:1 to 1:4 and in particular 1.2:1 to 1:3, where the molar ratio is based on the amount of transition metal (in mol) in the catalyst precursor. The formed catalyst can either be isolated before being used in the reaction or the obtained reaction mixture can be used without isolation of the complex.

If the catalyst is formed in situ, catalyst precursor and chiral ligand come into contact with each other in the presence of at least one of the reactants, e.g. of starting compound 1, the reduction agent and/or base (if used). Depending on the nature of the catalyst precursor, the formation of the catalyst might only start when a base is present. The base can be either the base mentioned above which is mandatorily used if HCOOH is used as reduction agent, or can be the formate if the reduction agent is used in this form. Preferably, catalyst precursor and chiral ligand are brought into contact with each other under conditions under which the catalyst precursor and chiral ligand can form the catalyst complex (in which the central metal is bound to the chiral ligand) before being contacted with starting compound 1. Thus, preferably, catalyst precursor and chiral ligand are brought into contact in the presence of the base (if used) and optionally also of the reduction agent, or in the presence of the formate if no additional base is used; and optionally also in the presence of a solvent, if the reaction is not to be carried out neat; and only thereafter the resulting mixture is brought into contact with starting compound 1. The catalyst precursor and the chiral ligand are generally used in a molar ratio of from 2:1 to 1:5, preferably from 1.5:1 to 1:4 and in particular from 1.2:1 to 1:3, where the molar ratio is based on the amount of transition metal (in mol) in the catalyst precursor.

In a preferred embodiment, in the compound 2 obtained in step (a) the S enantiomer is enriched (to the expense of the R-enantiomer, of course). Thus, in a preferred embodiment, step (a) serves for preparing 2-[(2S)-2-(2-chlorothiazol-5-yl)-2-hydroxy-ethyl]sulfanyl-6-hydroxy-3-methyl-5-phenyl-pyrimidin-4-one of the formula 2-S

2-S

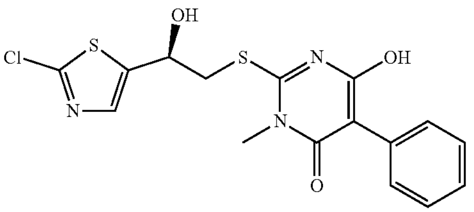

in enantiomeric excess, to be more precise in an enantiomeric excess of at least 55% ee, preferably at least 60% ee, more preferably at least 70% ee, in particular at least 80% ee and specifically at least 90% ee.

This is obtained by using the suitable chiral catalyst. This is preferably a transition metal catalyst, preferably a group VIII transition metal catalyst, more preferably a group 8 or 9 metal catalyst, in particular a Ru, Rh or Ir catalyst comprising a chiral ligand selected from the group consisting of (1S,2S)-DPEN, (1S,2S)-TsDPEN, (1S,2S)-$CF_3$TsDPEN, (1S,2S)-MsDPEN, (1S,2S)-MeMsDPEN, (1S,2S)-MeTsDPEN, (1S,2S)-FsDPEN, (1S,2S)-TripsMesitylDPEN, (1S,2S)-CsDPEN, (1S,2S)-MesitylDPEN, (1S,2S)-RsDPEN, (1S,2S)-TsDiOMeDPEN and the (1S,2S) form of a compound of the formula (II), wherein $R^7$ is $SO_2R^9$, where $R^9$ is $C_1$-$C_4$-alkyl or phenyl which may carry 1, 2 or 3 substituents selected from the group consisting of $C_1$-$C_4$-alkyl and $C_1$-$C_4$-haloalkyl, $R^8$ is —$(CH_2)_3$-phenyl or —$(CH_2)_4$-phenyl, where phenyl in the two last-mentioned radicals may carry 1, 2 or 3 substituents selected from the group consisting of $C_1$-$C_4$-alkyl, $C_1$-$C_4$-haloalkyl and $C_1$-$C_4$-alkoxy; and m and n are 0; and preferably comprising a chiral ligand selected from the group consisting of (1S,2S)-TsDPEN, (1S,2S)-$CF_3$TsDPEN, (1S,2S)-MsDPEN, (1S,2S)-MeMsDPEN, (1S,2S)-MeTsDPEN, (1S,2S)-CsDPEN, (1S,2S)-MesitylDPEN, (1S,2S)-RsDPEN, (1S,2S)-TsDiOMeDPEN and the (1S,2S) form of a compound of the formula (II), wherein $R^7$ is $SO_2R^9$, where $R^9$ is $C_1$-$C_4$-alkyl or phenyl which may carry 1, 2 or 3 substituents selected from the group consisting of $C_1$-$C_4$-alkyl and $C_1$-$C_4$-haloalkyl, $R^8$ is —$(CH_2)_3$-phenyl or —$(CH_2)_4$-phenyl, where phenyl in the two last-mentioned radicals may carry 1, 2 or 3 substituents selected from the group consisting of $C_1$-$C_4$-alkyl, $C_1$-$C_4$-haloalkyl and $C_1$-$C_4$-alkoxy; and m and n are 0.

In particular, the chiral transition metal catalyst used for obtaining 2-S in enantiomeric excess comprises as central metal Ru, Rh or Ir and comprises a chiral ligand selected from the group consisting of (1S,2S)-DPEN, (1S,2S)-TsDPEN, (1S,2S)-$CF_3$TsDPEN, (1S,2S)-MsDPEN, (1S,2S)-MeMsDPEN, (1S,2S)-MeTsDPEN, (1S,2S)-FsDPEN, (1S,2S)-TripsMesitylDPEN, (1S,2S)-CsDPEN, (1S,2S)-MesitylDPEN, (1S,2S)-RsDPEN and (1S,2S)-TsDiOMeDPEN; or is a catalyst containing Ru as central metal and at least one ligand selected from the (1S,2S) form of compounds of the formula (II), wherein $R^7$ is $SO_2R^9$, where $R^9$ is $C_1$-$C_4$-alkyl or phenyl which may carry 1, 2 or 3 substituents selected from the group consisting of $C_1$-$C_4$-alkyl and $C_1$-$C_4$-haloalkyl, $R^8$ is —$(CH_2)_3$-phenyl or —$(CH_2)_4$-phenyl, where phenyl in the two last-mentioned radicals may carry 1, 2 or 3 substituents selected from the group consisting of $C_1$-$C_4$-alkyl, $C_1$-$C_4$-haloalkyl and $C_1$-$C_4$-alkoxy; and m and n are 0. More particularly, the chiral transition metal catalyst used for obtaining 2-S in enantiomeric excess comprises as central metal Ru, Rh or Ir and comprises a chiral ligand selected from the group consisting of (1S,2S)-TsDPEN, (1S,2S)-$CF_3$TsDPEN, (1S,2S)-MsDPEN, (1S,2S)-MeMsDPEN, (1S,2S)-MeTsDPEN, (1S,2S)-CsDPEN, (1S,2S)-MesitylDPEN, (1S,2S)-RsDPEN and (1S,2S)-TsDiOMeDPEN; or is a catalyst containing Ru as central metal and at least one ligand selected from the (1S,2S) form of compounds of the formula (II), wherein $R^7$ is $SO_2R^9$, where $R^9$ is $C_1$-$C_4$-alkyl or phenyl which may carry 1, 2 or 3 substituents selected from the group consisting of $C_1$-$C_4$-alkyl and $C_1$-$C_4$-haloalkyl, $R^8$ is —$(CH_2)_3$-phenyl or —$(CH_2)_4$-phenyl, where phenyl in the two last-mentioned radicals may carry 1, 2 or 3 substituents selected from the group consisting of $C_1$-$C_4$-alkyl, $C_1$-$C_4$-haloalkyl and $C_1$-$C_4$-alkoxy; and m and n are 0.

More specifically, the chiral transition metal catalyst used for obtaining 2-S in enantiomeric excess is selected from catalysts containing Ru, Rh or Ir as central metal and at least one ligand selected from the group consisting of (1S,2S)-TsDPEN, (1S,2S)-$CF_3$TsDPEN, (1S,2S)-MsDPEN, (1S,2S)-MeMsDPEN, (1S,2S)-MeTsDPEN, (1S,2S)-CsDPEN, (1S,2S)-MesitylDPEN, (1S,2S)-RsDPEN and (1S,2S)-TsDiOMeDPEN, or is catalyst of the following formula:

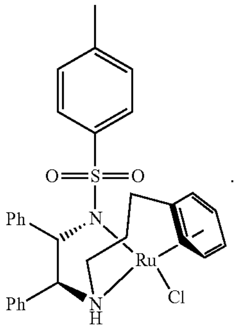

.

Very specifically, the chiral transition metal catalyst used for obtaining 2-S in enantiomeric excess is selected from catalysts containing Ru, Rh or Ir as central metal and at least one ligand selected from the group consisting of (1S,2S)-TsDPEN, (1S,2S)-MsDPEN and (1S,2S)-CsDPEN.

More particularly, the chiral transition metal catalyst used for obtaining 2-S in enantiomeric excess comprises as central metal Ru, Rh or Ir and comprises a chiral ligand selected from the group consisting of (1S,2S)-DPEN, (1S,2S)-TsDPEN, (1S,2S)-$CF_3$TsDPEN, (1S,2S)-MsDPEN, (1S,2S)-MeMsDPEN, (1S,2S)-MeTsDPEN, (1S,2S)-FsDPEN, (1S,2S)-TripsMesitylDPEN, (1S,2S)-CsDPEN, (1S,2S)-MesitylDPEN, (1S,2S)-RsDPEN and (1S,2S)-Ts-DiOMeDPEN, and comprises additionally a ligand selected from aromatic rings such as substituted or unsubstituted benzene and substituted or unsubstituted cyclopentadiene, e.g. Cp, Cp*, benzene, p-cymene, mesitylene or hexamethylbenzene. As already explained above, 5-membered $\eta^5$ aromatic ligands, such as Cp and Cp* are better suited for Rh or Ir as central metal; therefore in case of Rh and Ir as central metal, the additional aromatic ligand is preferably selected from Cp and Cp*, and is specifically Cp*. In case of Ru as central metal, the additional aromatic ligand is preferably selected from cymene and mesitylene. Even more particularly, the chiral transition metal catalyst used for obtaining (2-S) in enantiomeric excess comprises as central metal Ru, Rh or Ir and comprises a chiral ligand selected from the group consisting of (1S,2S)-TsDPEN, (1S,2S)-$CF_3$TsDPEN, (1S,2S)-MsDPEN, (1S,2S)-MeMsDPEN, (1S,2S)-MeTsDPEN, (1S,2S)-CsDPEN, (1S,2S)-MesitylDPEN, (1S,2S)-RsDPEN and (1S,2S)-TsDiOMeDPEN, and comprises additionally a ligand selected from aromatic rings such as substituted or unsubstituted benzene and substituted or unsubstituted cyclopentadiene, e.g. Cp, Cp*, benzene, p-cymene, mesitylene or hexamethylbenzene; in case of Rh and Ir as central metal specifically the $\eta^5$ ligand Cp*; and in case of Ru as central metal specifically cymene or mesitylene.

Moreover, the catalyst comprises a further ligand, in general a halide or sulfonate, preferably halide, specifically Cl, which is to be replaced by a hydride from the reduction agent.

Alternatively, the catalyst used for obtaining 2-S in enantiomeric excess contains Ru as central metal and at least one ligand selected from the (1S,2S) form of compounds of the formula (II), wherein $R^7$ is $SO_2R^9$, where $R^9$ is $C_1$-$C_4$-alkyl or phenyl which may carry 1, 2 or 3 substituents selected from the group consisting of $C_1$-$C_4$-alkyl and $C_1$-$C_4$-haloalkyl, $R^8$ is —$(CH_2)_3$-phenyl or —$(CH_2)_4$-phenyl, where phenyl in the two last-mentioned radicals may carry 1, 2 or 3 substituents selected from the group consisting of $C_1$-$C_4$-alkyl, $C_1$-$C_4$-haloalkyl and $C_1$-$C_4$-alkoxy; and m and n are 0. Generally, also this type of catalyst contains a further ligand, in general a halide or sulfonate, preferably halide, specifically Cl, which is to be replaced by a hydride from the reduction agent. This type of catalyst is specifically a compound of the following formula:

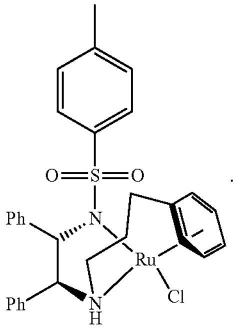

Specifically, the chiral transition metal catalyst used for obtaining 2-S in enantiomeric excess is selected from catalysts containing Ru, Rh or Ir as central metal, a chiral ligand selected from the group consisting of (1S,2S)-TsDPEN, (1S,2S)-MsDPEN and (1S,2S)-CsDPEN, a ligand selected from halogen ligands, preferably, a Cl ligand, and a further ligand selected from Cp*, p-cymene and mesitylene.

In another preferred embodiment, in the compound 2 obtained in step (a) the R enantiomer is enriched (to the expense of the S-enantiomer, of course). Thus, in a preferred embodiment, step (a) serves for preparing 2-[(2R)-2-(2-chlorothiazol-5-yl)-2-hydroxy-ethyl]sulfanyl-6-hydroxy-3-methyl-5-phenyl-pyrimidin-4-one of the formula 2-R

2-R

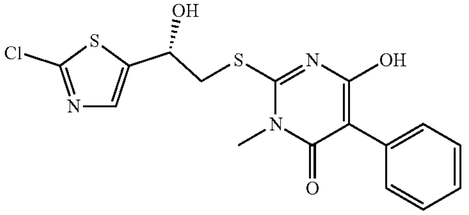

in enantiomeric excess, to be more precise in an enantiomeric excess of at least 55% ee, preferably at least 60% ee, more preferably at least 70% ee, in particular at least 80% ee and specifically at least 90% ee.

This is obtained by using the suitable chiral catalyst. This is preferably a transition metal catalyst, preferably a group VIII transition metal catalyst, more preferably a group 8 or 9 metal catalyst, in particular a Ru, Rh or Ir catalyst comprising a chiral ligand selected from the group consisting of (1R,2R)-DPEN, (1R,2R)-TsDPEN, (1R,2R)-$CF_3$TsDPEN, (1R,2R)-MsDPEN, (1R,2R)-MeMsDPEN, (1R,2R)-MeTsDPEN, (1R,2R)-FsDPEN, (1R,2R)-TripsMesitylDPEN, (1R,2R)-CsDPEN, (1R,2R)-MesitylDPEN, (1R,2R)-RsDPEN, (1R,2R)-TsDiOMeDPEN and of the (1R,2R) form of a compound of the formula (II), wherein $R^7$ is $SO_2R^9$, where $R^9$ is $C_1$-$C_4$-alkyl or phenyl which may carry 1, 2 or 3 substituents selected from the group consisting of $C_1$-$C_4$-alkyl and $C_1$-$C_4$-haloalkyl, $R^8$ is —$(CH_2)_3$-phenyl or —$(CH_2)_4$-phenyl, where phenyl in the two last-mentioned radicals may carry 1, 2 or 3 substituents selected from the group consisting of $C_1$-$C_4$-alkyl, $C_1$-$C_4$-haloalkyl and $C_1$-$C_4$-alkoxy; and m and n are 0; and preferably comprising a chiral ligand selected from the group consisting of (1R,2R)-TsDPEN, (1R,2R)-$CF_3$TsDPEN, (1R,2R)-MsDPEN, (1R,2R)-MeMsDPEN, (1R,2R)-MeTsDPEN, (1R,2R)-CsDPEN, (1R,2R)-MesitylDPEN, (1R,2R)-RsDPEN, (1R, 2R)-TsDiOMeDPEN and of the (1R,2R) form of a compound of the formula (II), wherein $R^7$ is $SO_2R^9$, where $R^9$ is $C_1$-$C_4$-alkyl or phenyl which may carry 1, 2 or 3 substituents selected from the group consisting of $C_1$-$C_4$-alkyl and $C_1$-$C_4$-haloalkyl, $R^8$ is —$(CH_2)_3$-phenyl or —$(CH_2)_4$-phenyl, where phenyl in the two last-mentioned radicals may carry 1, 2 or 3 substituents selected from the group consisting of $C_1$-$C_4$-alkyl, $C_1$-$C_4$-haloalkyl and $C_1$-$C_4$-alkoxy; and m and n are 0.

In particular, the chiral transition metal catalyst used for obtaining 2-R in enantiomeric excess comprises as central metal Ru, Rh or Ir and comprises a chiral ligand selected from the group consisting of (1R,2R)-DPEN, (1R,2R)-TsDPEN, (1R,2R)-$CF_3$TsDPEN, (1R,2R)-MsDPEN, (1R,2R)-MeMsDPEN, (1R,2R)-MeTsDPEN, (1R,2R)-FsDPEN, (1R,2R)-TripsMesitylDPEN, (1R,2R)-CsDPEN, (1R,2R)-MesitylDPEN, (1R,2R)-RsDPEN and (1R,2R)-TsDiOMeDPEN; or is a catalyst containing Ru as central metal and at least one ligand selected from the (1R,2R) form of compounds of the formula (II), wherein $R^7$ is $SO_2R^9$, where $R^9$ is $C_1$-$C_4$-alkyl or phenyl which may carry 1, 2 or 3 substituents selected from the group consisting of $C_1$-$C_4$-alkyl and $C_1$-$C_4$-haloalkyl, $R^8$ is —$(CH_2)_3$-phenyl or —$(CH_2)_4$-phenyl, where phenyl in the two last-mentioned radicals may carry 1, 2 or 3 substituents selected from the group consisting of $C_1$-$C_4$-alkyl, $C_1$-$C_4$-haloalkyl and $C_1$-$C_4$-alkoxy; and m and n are 0. More particularly, the chiral transition metal catalyst used for obtaining 2-R in enantiomeric excess comprises as central metal Ru, Rh or Ir and comprises a chiral ligand selected from the group consisting of (1R,2R)-TsDPEN, (1R,2R)-$CF_3$TsDPEN, (1R,2R)-MsDPEN, (1R,2R)-MeMsDPEN, (1R,2R)-MeTsDPEN, (1R,2R)-CsDPEN, (1R,2R)-MesitylDPEN, (1R,2R)-RsDPEN and (1R,2R)-TsDiOMeDPEN; or is a catalyst containing Ru as central metal and at least one ligand selected from the (1R,2R) form of compounds of the formula (II), wherein $R^7$ is $SO_2R^9$, where $R^9$ is $C_1$-$C_4$-alkyl or phenyl which may carry 1, 2 or 3 substituents selected from the group consisting of $C_1$-$C_4$-alkyl and $C_1$-$C_4$-haloalkyl, $R^8$ is —$(CH_2)_3$-phenyl or —$(CH_2)_4$-phenyl, where phenyl in the two last-mentioned radicals may carry 1, 2 or 3 substituents selected from the group consisting of $C_1$-$C_4$-alkyl, $C_1$-$C_4$-haloalkyl and $C_1$-$C_4$-alkoxy; and m and n are 0.

More specifically, the chiral transition metal catalyst used for obtaining 2-R in enantiomeric excess is selected from catalysts containing Ru, Rh or Ir as central metal and at least one ligand selected from the group consisting of (1R,2R)-TsDPEN, (1R,2R)-$CF_3$TsDPEN, (1R,2R)-MsDPEN, (1R,2R)-MeMsDPEN, (1R,2R)-MeTsDPEN, (1R,2R)-CsDPEN, (1R,2R)-MesitylDPEN, (1R,2R)-RsDPEN and (1R,2R)-TsDiOMeDPEN, or is a catalyst of the following formula:

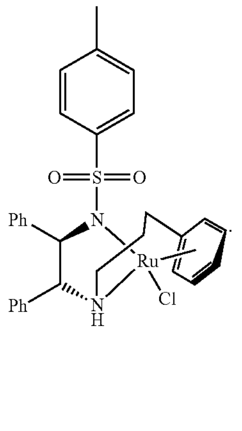

Very specifically, the chiral transition metal catalyst used for obtaining 2-R in enantiomeric excess is selected from catalysts containing Ru, Rh or Ir as central metal and at least one ligand selected from the group consisting of (1R,2R)-TsDPEN, (1R,2R)-MsDPEN anf (1R,2R)-CsDPEN.

More particularly, the chiral transition metal catalyst used for obtaining 2-R in enantiomeric excess comprises as central metal Ru, Rh or Ir and comprises a chiral ligand selected from the group consisting of (1R,2R)-DPEN, (1R,2R)-TsDPEN, (1R,2R)-$CF_3$TsDPEN, (1R,2R)-MsDPEN, (1R,2R)-MeMsDPEN, (1R,2R)-MeTsDPEN, (1R,2R)-FsDPEN, (1R,2R)-TripsMesitylDPEN, (1R,2R)-CsDPEN, (1R,2R)-MesitylDPEN, (1R,2R)-RsDPEN and (1R,2R)-TsDiOMeDPEN, and comprises additionally a ligand selected from aromatic rings such as substituted or unsubstituted benzene and substituted or unsubstituted cyclopentadiene, e.g. Cp, Cp*, benzene, p-cymene, mesitylene or hexamethylbenzene. As already explained above, 5-membered $\eta^5$ aromatic ligands, such as Cp and Cp* are better suited for Rh or Ir as central metal; therefore in case of Rh and Ir as central metal, the additional aromatic ligand is preferably selected from Cp and Cp*, and specifically Cp*. In case of Ru as central metal, the additional aromatic ligand is preferably selected from cymene and mesitylene. Even more particularly, the chiral transition metal catalyst used for obtaining (2-R) in enantiomeric excess comprises as central metal Ru, Rh or Ir and comprises a chiral ligand selected from the group consisting of (1R,2R)-TsDPEN, (1R,2R)-$CF_3$TsDPEN, (1R,2R)-MsDPEN, (1R,2R)-MeMsDPEN, (1R,2R)-MeTsDPEN, (1R,2R)-CsDPEN, (1R,2R)-MesitylDPEN, (1R,2R)-RsDPEN and (1R,2R)-TsDiOMeDPEN, and comprises additionally a ligand selected from aromatic rings such as substituted or unsubstituted benzene and substituted or unsubstituted cyclopentadiene, e.g. Cp, Cp*, benzene, p-cymene, mesitylene or hexamethylbenzene; in case of Rh and Ir as central metal specifically the $\eta^5$ ligand Cp*; and in case of Ru as central metal specifically cymene or mesitylene.

Moreover, the catalyst comprises a further ligand, in general a halide or sulfonate, preferably a halide, specifically Cl, which is to be replaced by a hydride from the reduction agent.

Alternatively, the catalyst used for obtaining 2-R in enantiomeric excess contains Ru as central metal and at least one ligand selected from the (1R,2R) form of compounds of the formula (II), wherein $R^7$ is $SO_2R^9$, where $R^9$ is $C_1$-$C_4$-alkyl or phenyl which may carry 1, 2 or 3 substituents selected from the group consisting of $C_1$-$C_4$-alkyl and $C_1$-$C_4$-haloalkyl, $R^8$ is —$(CH_2)_3$-phenyl or —$(CH_2)_4$-phenyl, where phenyl in the two last-mentioned radicals may carry 1, 2 or 3 substituents selected from the group consisting of $C_1$-$C_4$-alkyl, $C_1$-$C_4$-haloalkyl and $C_1$-$C_4$-alkoxy; and m and n are 0. Generally, also this type of catalyst contains a further ligand, in general a halide or sulfonate, preferably halide, specifically Cl, which is to be replaced by a hydride from the reduction agent. This type of catalyst is specifically a compound of the following formula:

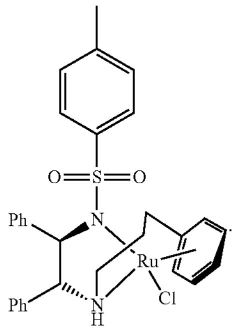

Specifically, the chiral transition metal catalyst used for obtaining 2-R in enantiomeric excess is selected from catalysts containing Ru, Rh or Ir as central metal, a chiral ligand selected from the group consisting of (1R,2R)-TsDPEN, (1R,2R)-MsDPEN and (1R,2R)-CsDPEN, a ligand selected from halogen ligands, preferably, a Cl ligand, and a further ligand selected from Cp*, p-cymene and mesitylene.

The reaction, both in steps (a) and (b) can be carried out in the presence of a solvent. The solvent is preferably selected from the group consisting of polar aprotic solvents, chlorinated alkanes, aromatic solvents, heterocyclic solvents and mixtures of the aforementioned solvents. In some cases, e.g. if $PCl_3$ is used as activating agent, mixtures of said organic solvents with minor amounts of water may be advantageous. Moreover, if formate is used as only reduction agent or if it predominates in the formic acid/formate mixture used as reduction agent, the presence of water is also necessary.

Polar aprotic solvents are polar solvents without a functional group from which a proton can dissociate. Examples for suitable polar aprotic solvents are amides, such as dimethylformamide (DMF), diethylformamide, dibutylformamide, and dimethylacetamide; cyclic ethers, such as tetrahydrofuran, 2-methyltetrahydrofuran, 1,3-dioxane and 1,4-dioxane; sulfoxides, such as dimethylsulfoxide (DMSO); nitriles, such as acetonitrile; lactams, such as N-methylpyrrolidone (NMP), N-(n-butyl)-pyrrolidone or N-(tert-butyl)-pyrrolidone; sulfones, such as sulfolane; carbonic acid esters, such as dimethylcarbonate, ethylenecarbonate or propylene carbonate; lactones, such as γ-butyrolactone or γ-valerolactone; ureas, such as N,N,N',N'-tetramethyl urea, N,N,N',N'-tetrabutyl urea, dimethylpropylene urea (DMPU) or 1,3-dimethyl-2-imidazolinone (DMEU; DMI); and nitro compounds, such as nitromethane.

Examples for suitable $C_1$-$C_4$-alkyl acetates are methyl acetate, ethyl acetate, n-propyl acetate, isopropyl acetate and n-butyl acetate.

Examples for suitable chlorinated alkanes are dichloromethane, trichloromethane or dichloroethane.

Examples for suitable aromatic solvents are benzene, toluene, α,α,α-trifluorotoluene (benzotrifluoride), the xylenes (i.e. 1,2-xylene, 1,3-xylene or 1,4-xylene), fluorobenzene, chlorobenzene, dichlorobenzene or anisole (methoxybenzene).

Examples for suitable heterocyclic solvents are 4-formyl morpholine or dihydrolevoglucosenone (Cyrene®).

If mixtures of the listed organic solvents with water are used, these contain generally up to 15% by weight of water (e.g. 0.5 to 15% by weight), preferably up to 10% by weight of water (e.g. 1 to 10% by weight), in particular up to 5% by weight of water (e.g. 1 to 5% by weight), specifically up to 3% by weight of water of water (e.g. 1 to 3% by weight), relative to the overall weight of the solvent (to be more precise of the mixture of organic solvent and water).

More preferably, the solvent is selected from the group consisting of dimethylformamide, diethylformamide, dibutylformamide, dimethylacetamide, tetrahydrofuran, 2-methyltetrahydrofuran, the dioxanes (i.e. 1,3- and 1,4-dioxane), dimethylsulfoxide, acetonitrile, N-methylpyrrolidone, N-(n-butyl)-pyrrolidone, N-(tert-butyl)-pyrrolidone, sulfolane, dimethylcarbonate, diethylcarbonate, propylene carbonate, γ-valerolactone, N,N,N',N'-tetrabutyl urea, 1,3-dimethyl-2-imidazolinone, ethyl acetate, isopropyl acetate, dichloromethane, trichloromethane, dichloroethane, benzene, toluene, α,α,α-trifluorotoluene, the xylenes, fluorobenzene, chlorobenzene, dichlorobenzene, anisole, 4-formyl morpholine, dihydrolevoglucosenone (Cyrene®), mixtures of the aforementioned solvents, and mixtures of the aforementioned solvents with water; in particular from dimethylformamide, dimethylacetamide, dichloromethane, trichloromethane, dichloroethane and mixtures thereof; and specifically from dimethylformamide, dimethylacetamide and mixtures thereof.

If however formic acid is used as or comprised in the reduction agent and/or a base is used which is liquid at the reaction temperature, the reaction in step (a) can alternatively be carried out neat.

If a formate is used as only reduction agent, it is expedient to use this in admixture with water. In this case, the solvent comprises preferably also water.

During reaction in step (a), formic acid or the formate is oxidized to $CO_2$. Given that $CO_2$ inhibits the activity of a number of catalysts, it is expedient to remove $CO_2$ during reaction in step (a). This can for example be carried out by sparging a gas inert to the reaction through the reaction mixture or by applying a vacuum. Therefore, in a preferred embodiment, during the reaction in step (a), an inert gas different from $CO_2$ and which preferably selected from the group consisting of argon, nitrogen, and mixtures of oxygen and nitrogen containing 1-8 vol-% of oxygen, relative to the total amount of the oxygen/nitrogen mixture, is sparged through the reaction mixture; or alternatively or additionally the reaction is carried out under reduced pressure. Specifically, nitrogen is used to remove $CO_2$. The inert gas is typically used at a flow rate of from 1 to 200 l/h, preferably from 1 to 80 l/h, more preferably from 1 to 50 l/h, in particular from 1 to 20 l/h. On industrial scale, the flow rate can of course be distinctly higher, e.g. up to 5000 l/h.

The reaction in steps (a) and (b) can be carried out in the presence of an additive which accelerates the reaction rate. Typical additives are diethyl phosphite, borate esters and zinc salts. Suitable zinc salts are for example zinc halides, zinc acetate or zinc trifluoromethanesulfonate. Specifically, diethyl phosphite or a zinc salt, especially zinc acetate, is used. The additive is preferably used in such an amount that the molar ratio of additive and the compound 1 is in the range of from 1:10000 to 10:1, in particular from 1:10000 to 5:1, specifically from 1:10000 to 2:1.

The reaction in step (a) is carried out at a temperature of preferably from −20 to 120° C. The optimum temperature depends inter alia from the catalyst used. For instance, for some Ru catalysts higher reaction temperatures might be advantageous, so that the reaction temperature in this case is preferably in the range of from 30 to 100° C., e.g. from 50 to 90° C., whereas in case of Rh and Ir lower reaction temperatures are sufficient, so that the reaction temperature in this case is preferably in the range of from −20 to 30° C., and in particular from −15 to 25° C. But Ru catalysts also work at temperatures in this range, especially at 10 to 30° C.

The reaction time of step (a) depends on various factors, such as the reaction temperature, the concentration of the reactants in the reaction mixture and the like. Typically, it is in the range of from about 0 to 48 h, preferably from 1 to 16 h. A reaction time of "0 h" in this context means that after complete addition of all components, the reaction can be sufficiently complete to continue with step (b). This can for example be the case if the addition of the reactants has lasted rather long or if it is intended to recycle the non-reacted starting material.

The reaction in step (a) is generally carried out by mixing the reduction agent, optionally the base (where in case of the use of formic acid as only reduction agent, mixing with the base is mandatory), the chiral catalyst (either in preformed form or in form of a catalyst precursor and a chiral ligand), optionally the solvent and optionally the additive at the desired reaction temperature or mixing the components and bringing then the temperature to the desired range. The order of addition is not particularly critical.

For instance, (i) the reduction agent and optionally the base (in case of formic acid as only reduction agent: mandatorily the base) are added as a mixture or separately (where separate addition can be carried out simultaneously or successively) to a mixture of the compound 1 and the chiral catalyst in a solvent; or (ii) the chiral catalyst in a solvent is added to a mixture of the compound 1, the reduction agent, optionally the base (in case of formic acid as only reduction agent: mandatorily the base) and optionally a solvent (if a formate is used as only reduction agent and no liquid base is used: mandatorily a solvent); or (iii) the reduction agent, optionally in a solvent, is added to a mixture of the compound 1, the chiral catalyst, optionally the base (in case of formic acid as only reduction agent: mandatorily the base) and optionally a solvent (if no liquid base is used: mandatorily a solvent); or (iv) compound 1 in a solvent is added to a mixture of the chiral catalyst, the reduction agent, optionally the base (in case of formic acid as only reduction agent: mandatorily the base) and optionally a solvent (if a formate is used as only reduction agent and no liquid base is used: mandatorily a solvent).

The reaction mixture obtained in step (a) is reacted in subsequent step (b) without isolating the compound 2. Compound 2 is quite sensitive and may degrade to some extent upon storage or even when applying usual isolation methods. In tendency, not isolating compound 2 yields the compound (I) in higher yields as compared to a method where compound 2 is isolated before being subjected to step (b).

Generally, reacting the reaction mixture of step (a) in step (b) without isolating the compound 2 is done by simply bringing the activating compound into contact with the reaction mixture of obtained in step (a), i.e. by adding the activating compound to the reaction mixture of obtained in step (a).

The activating agent used in step (b) is a compound which enhances electrophilicity of the carbon atom marked with the asterisk in the compound of the formula 2 without promoting racemization at said carbon atom. The reaction of 2 to the compound (I) is an intramolecular nucleophilic substitution in which the unsubstituted nitrogen atom of the pyrimidinone ring attacks the aliphatic carbon atom marked with the asterisk and substitutes the OH group, thus forming a condensed ring system. To preserve the chiral information of 2 in compound (I) to a maximum extent, conditions of this reaction are expediently such that racemization at the carbon atom marked with the asterisk is suppressed or at least minimized. This is expediently done by ensuring a nucleophilic attack under $S_N2$ conditions. The activating agent is thus alternatively defined as a compound which promotes an intermolecular $S_N2$ attack at the carbon atom marked with the asterisk in the compound of the formula 2.

Suitable activating agents are oxygenophilic compounds, such as various phosphorus compounds, but also certain compounds or compositions of compounds with Lewis acid properties.

Preferably, the activating agent is selected from the group consisting of $P(OR^1)_2Cl$, $P(OR^1)Cl_2$, $P(=O)(OR^1)_2Cl$, $P(=O)(OR^1)Cl_2$, where each $R^1$ in the four aforementioned compounds is independently $C_1$-$C_4$-alkyl; $PCl_3$, $P(=O)Cl_3$, polyphosphoric acid, $P_4O_{10}$, Mitsunobu-type reagents, triphenylphosphine in combination with a halogenating agent, $SO_3$ complexes with Lewis bases selected from amines, carboxamides and heteroaromatic compounds containing 1, 2 or 3 basic nitrogen ring atoms; $S(O)Cl_2$, $CH_3S(O)_2Cl$, carbonyldiimidazole (CDI), Vilsmeier reagent, complexes of N,N-dimethylformamide and/or N,N-dimethylacetamide with a Lewis acid; and mixtures of two or more of the aforementioned activating agents.

Mitsunobu-type reagents are combinations of triphenylphosphine with an azodicarboxylate, such as diethylazodicarboxylate (DEAD) or diisopropylazodicarboxylate (DIAD), or combinations of triphenylphosphine with an azodicarboxamide, such as tetramethylazodicarboxamide (TMAD). These combinations are either used as mixtures or are admixed in situ during reaction. Expediently, they can be used as commercially available mixtures.

Examples for halogenating agents to be used in combination with triphenylphosphine are N-chlorosuccinimide (NCS), N-bromosuccinimide (NBS), elementary chlorine, elementary bromine or elementary iodine. These combinations are either used as mixtures or are admixed in situ during reaction.

Examples for $SO_3$ complexes with Lewis bases selected from amines, carboxamides and heteroaromatic compounds containing 1, 2 or 3 basic nitrogen ring atoms are $SO_3$ complexes with trimethylamine, triethylamine, N,N-dimethylaniline, N,N-dimethylformamide, pyridine or polyvinylpyridine. These combinations are either used as mixtures or are admixed in situ during reaction. Expediently, they can be used as commercially available mixtures.

Vilsmeier reagent is the product of the reaction of a formamide ($HC(O)NR_2$, where each R is independently $C_1$-$C_4$-alkyl) with phosphoryl chloride ($P(O)Cl_3$), oxalyl chloride ($ClC(O)—C(O)Cl$) or thionyl chloride ($S(O)Cl_2$), which results in a chloroiminium ion ($ClHC=NR_2^+$). Generally, dimethylformamide is used, i.e. both R are methyl.

One examples for a Lewis acid in the complexes of N,N-dimethylformamide and/or N,N-dimethylacetamide with a Lewis acid is $BF_3$.

The activating agent is more preferably selected from the group consisting of $P(OR^1)_2Cl$, $P(OR^1)Cl_2$, $P(=O)(OR^1)_2Cl$, where each $R^1$ in the three aforementioned compounds is independently $C_1$-$C_4$-alkyl; $PCl_3$, $P(O)Cl_3$, $SO_3$/dimethyl formamide complex, $SOCl_2$, $CH_3S(=O)_2Cl$, CDI and Mitsunobu-type reagents; and in particular from dimethyl chlorophosphite ($P(OCH_3)_2Cl$), diethyl chlorophosphite ($P(OCH_2CH_3)_2Cl$), methyl dichlorophosphite ($P(OCH_3)Cl_2$), ethyl dichlorophosphite ($P(OCH_2CH_3)Cl_2$), $PCl_3$, $P(O)Cl_3$, $SOCl_2$, $CH_3S(=O)_2Cl$, CDl and Mitsunobu-type reagents. More particularly, the activating agent is selected from the group consisting of dimethyl chlorophosphite ($P(OCH_3)_2Cl$), diethyl chlorophosphite ($P(OCH_2CH_3)_2Cl$), methyl dichlorophosphite ($P(OCH_3)Cl_2$), ethyl dichlorophosphite ($P(OCH_2CH_3)Cl_2$), $PCl_3$ and $P(O)Cl_3$. Even more particularly, the activating agent is selected from the group consisting of $P(OR^1)_2Cl$, specifically dimethyl chlorophosphite ($P(OCH_3)_2Cl$) and diethyl chlorophosphite ($P(OCH_2CH_3)_2Cl$), and $PCl_3$. Specifically, the activating agent is dimethyl chlorophosphite ($P(OCH_3)_2Cl$) or diethyl chlorophosphite ($P(OCH_2CH_3)_2Cl$).

The compound of the formula 2 and the activating agent are preferably used in a molar ratio of from 10:1 to 1:10, more preferably from 2:1 to 1:5, even more preferably from 1:1 to 1:4, in particular from 1:1 to 1:3 and specifically from 1:1 to 1:2.

The reaction in step (b) is preferably carried out in the presence of a solvent. If step (a) has been carried out in formic acid and/or a liquid base as solvent without any additional, typical solvent, it is expedient to add such a solvent. Suitable solvents are polar aprotic solvents, mixtures of polar aprotic solvents and water, $C_1$-$C_4$-alkyl acetates, chlorinated alkanes, aromatic solvents, heterocyclic solvents and mixtures thereof. Although aqueous solvents are generally considered to promote the $S_N1$ path in substitution reactions because they solubilize the generally ionic leaving group, in the present case, mixtures of polar aprotic solvents and water have nevertheless been found to be suitable; at least in combination with certain activating agents, such as $PCl_3$; see above remarks.

Polar aprotic solvents are polar solvents without a functional group from which a proton can dissociate. Examples for suitable polar aprotic solvents are amides, such as dimethylformamide (DMF), diethylformamide, dibutylformamide, and dimethylacetamide; cyclic ethers, such as tetrahydrofuran, 2-methyltetrahydrofuran, 1,3-dioxane and 1,4-dioxane; sulfoxides, such as dimethylsulfoxide (DMSO); nitriles, such as acetonitrile; lactams, such as N-methylpyrrolidone (NMP), N-(n-butyl)-pyrrolidone or N-(tert-butyl)-pyrrolidone; sulfones, such as sulfolan; carbonic acid esters, such as dimethylcarbonate, ethylenecarbonate or propylene carbonate; lactones, such as γ-butyrolactone or γ-valerolactone; ureas, such as N,N,N',N'-tetramethyl urea, N,N,N',N'-tetrabutyl urea, dimethylpropylene urea (DMPU) or 1,3-dimethyl-2-imidazolinone (DMEU; DMI); and nitro compounds, such as nitromethane.

In mixtures of polar aprotic solvents and water, the mixture contains water in an amount of preferably from 0.5 to 15% by weight, preferably from 1 to 10% by weight, in particular from 1 to 6% by weight, specifically from 1 to 4% by weight, based on the total weight of the mixture.

Examples for suitable $C_1$-$C_4$-alkyl acetates are methyl acetate, ethyl acetate, n-propyl acetate and isopropyl acetate.

Examples for suitable chlorinated alkanes are dichloromethane, trichloromethane or dichloroethane.

Examples for suitable aromatic solvents are benzene, toluene, α,α,α-trifluorotoluene (benzotrifluoride), the xylenes (i.e. 1,2-xylene, 1,3-xylene or 1,4-xylene), fluorobenzene, chlorobenzene, dichlorobenzene or anisole (methoxybenzene).

Examples for suitable heterocyclic solvents are 4-formyl morpholine or dihydrolevoglucosenone (Cyrene®).

More preferably, the solvent is selected from the group consisting of dimethylformamide, diethylformamide, dibutylformamide, dimethylacetamide, tetrahydrofuran, mixtures of tetrahydrofuran and water (e.g. containing water in an amount of from 0.5 to 15% by weight, preferably from 1 to 10% by weight, in particular from 1 to 6% by weight, specifically from 1 to 4% by weight, based on the total weight of the THF/water mixture), 2-methyltetrahydrofuran, the dioxanes (i.e. 1,3-dioxane and 1,4-dioxane), dimethylsulfoxide, acetonitrile, N-methylpyrrolidone, N-(n-butyl)-pyrrolidone, N-(tert-butyl)-pyrrolidone, sulfolane, dimethylcarbonate, diethylcarbonate, propylene carbonate, γ-valerolactone, N,N,N',N'-tetrabutyl urea, 1,3-dimethyl-2-imidazolinone, ethyl acetate, isopropyl acetate, dichloromethane, trichloromethane, dichloroethane, benzene, toluene, trifluorotoluene, the xylenes, chlorobenzene, dichlorobenzene, 4-formyl-morpholine, dihydrolevoglucosenone (Cyrene®) and mixtures thereof. In particular the solvent is selected from the group consisting of dimethylformamide, diethylformamide, dibutylformamide, dimethylacetamide, tetrahydrofuran, mixtures of tetrahydrofuran and water (e.g. containing water in an amount of from 0.5 to 15% by weight, preferably from 1 to 10% by weight, in particular from 1 to 6% by weight, specifically from 1 to 4% by weight, based on the total weight of the THE/water mixture), 2-methyltetrahydrofuran, 1,4-dioxane, acetonitrile, ethyl acetate, dichloromethane, toluene, chlorobenzene and mixtures thereof; in particular from dimethylformamide, dimethylacetamide, dichloromethane, trichloromethane and mixtures thereof; and specifically from dimethylformamide, dimethylacetamide and mixtures thereof.

If step (a) has not been carried out in the presence of a base (the base being different from the formate), it is possible to add in step (b) a base. The base is preferably selected from the group consisting of alkali metal hydroxides, amines of the formula $NR^1R^2R^3$, where $R^1$, $R^2$ and $R^3$, independently of each other, are selected from the group consisting of hydrogen, $C_1$-$C_6$-alkyl, $C_3$-$C_6$-cycloalkyl, $C_1$-$C_4$-alkoxy and $C_1$-$C_4$-alkoxy-$C_1$-$C_4$-alkyl, where at least one of $R^1$, $R^2$ and $R^3$ is not hydrogen; diamines of the formula $NR^1R^2$-A-$NR^3R^4$, where $R^1$, $R^2$, $R^3$ and $R^4$, independently of each other, are selected from the group consisting of hydrogen, $C_1$-$C_6$-alkyl, $C_3$-$C_6$-cycloalkyl, $C_1$-$C_4$-alkoxy and $C_1$-$C_4$-alkoxy-$C_1$-$C_4$-alkyl, and A is $(CH_2)_2$ or $(CH_2)_3$; and a 5- or 6-membered saturated heterocyclic ring containing one nitrogen atom as ring member and optionally one further heteroatom selected from N and O as ring member, where the ring may carry 1 to 6 $C_1$-$C_4$-alkyl groups and/or 1 or 2 OH groups. In particular, the base is selected from the group consisting of LiOH, NaOH, KOH, diethylamine, triethylamine, tributylamine, diisopropylethylamine, dimethylisopropylamine, ethyl-tert-butylamine, isopropyl-tert-butylamine, (2-methoxyethyl)methylamine, N,N-dicyclohexylmethylamine, N-cyclohexyldimethylamine, N,N,N',N'-tetramethylethylenediamine, N,N,N',N'-tetramethylpropylene-1,3-diamine, piperdine, N-methylpiperidine, 2,2,6,6-tetramethylpiperidine, N-methyl-2,6,6-tetramethylpiperidine, N-methyl-4-hydroxy-2,2,6,6-tetramethylpiperidine, morpholine and N-methylmorpholine, where the bases can be used in supported from (i.e. on a support material); and specifically from triethylamine, tributylamine and diisopropylethylamine.

Suitable support materials are listed above.

The addition of a base in step (b) is however not necessary. Base in this context refers to an additional base, i.e. a base which is different from the mandatory reactants. For instance, the formate of step (a) is basic; some activators contain basic components, such as the amines or heteroaromatic compounds in the $SO_3$ complexes with Lewis bases.

The reaction in step (b) is carried out at a temperature of preferably from −80 to 120° C., more preferably from −20 to 100° C., and in particular from −10 to 90° C. If step (b) is to be carried out at another temperature of step (a), this is expediently realized by adjusting the temperature of the reaction mixture obtained in step (a) to the desired temperature before adding the activating agent.

The reaction time of step (b) depends on various factors, such as the reaction temperature, the concentration of the reactants in the reaction mixture and the like. Typically, it is in the range of from about 15 min to 48 h, preferably from 1 to 10 h.

The reaction in step (b) is generally carried out by adding the activating agent to the reaction mixture obtained in step (a). Depending on the activating agent used, it can be expedient to add the agent to the reaction mixture obtained in step (a) cooled to −80 to 10° C., e.g. to −20 to 0° C., and warm the reaction mixture only after completion of addition if a higher reaction temperature than the temperature at addition is desired. Depending on the reactivity of the activating agent, it can be expedient to add the latter gradually (continuously or portion-wise) to avoid heat development. The reactivity is not only dependent from the type of activating agent, but also from its state after storage, so that preliminary tests are expedient.

Alternatively, step (b) is carried out by adding the reaction mixture obtained in step (a) to the activating agent. To this purpose, the activating agent is suitably provided in a solvent. Suitable solvents are those listed above for step (b).

In a preferred embodiment, the method of the invention serves for preparing (3R)-3-(2-chlorothiazol-5-yl)-8-methyl-7-oxo-6-phenyl-2,3-dihydrothiazolo[3,2-a]pyrimidin-4-ium-5-olate of the formula (I-R)

(I-R)

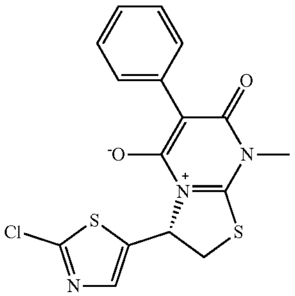

in an enantiomeric excess of at least 55% ee, preferably at least 60% ee, more preferably at least 70% ee, in particular at least 80% ee and specifically at least 90% ee.

To this purpose, compound 1 is hydrogenated under such conditions that a reaction mixture is obtained in which the S enantiomer of the compound 2 predominates, i.e. a reaction mixture containing 2-[(2S)-2-(2-chlorothiazol-5-yl)-2-hydroxy-ethyl]sulfanyl-6-hydroxy-3-methyl-5-phenyl-pyrimidin-4-one of the formula 2-S

2-S

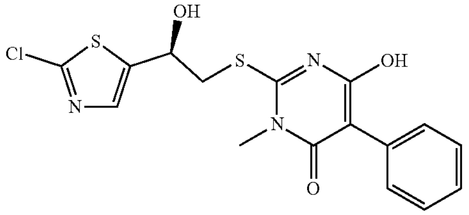

in an enantiomeric excess of at least 55% ee, preferably at least 60% ee, more preferably at least 70% ee, in particular at least 80% ee and specifically at least 90% ee. This is then reacted with an activating agent as described above.

The intramolecular nucleophilic attack proceeds predominantly from the reverse side to the OH leaving group, and thus with inversion of configuration at the asymmetric carbon atom (given that nucleophile and nucleofuge have the same priority according to the Cahn-Ingold-Prelog rules, the absolute configuration also changes from S to R).

Reaction conditions which yield reaction mixtures in which the S enantiomer of the compound 2 predominates are described above in context with step (a).

In another preferred embodiment, the method of the invention serves for preparing (3S)-3-(2-chlorothiazol-5-yl)-8-methyl-7-oxo-6-phenyl-2,3-dihydrothiazolo[3,2-a]pyrimidin-4-ium-5-olate of the formula (I-S)

(I-S)

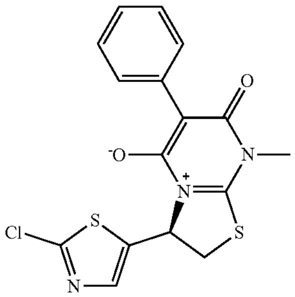

in an enantiomeric excess of at least 55% ee, preferably at least 60% ee, more preferably at least 70% ee, in particular at least 80% ee and specifically at least 90% ee.

To this purpose, compound 1 is hydrogenated under such conditions that a reaction mixture is obtained in which the R enantiomer of the compound 2 predominates, i.e. a reaction mixture containing 2-[(2R)-2-(2-chlorothiazol-5-yl)-2-hydroxy-ethyl]sulfanyl-6-hydroxy-3-methyl-5-phenyl-pyrimidin-4-one of the formula 1-R

1-R

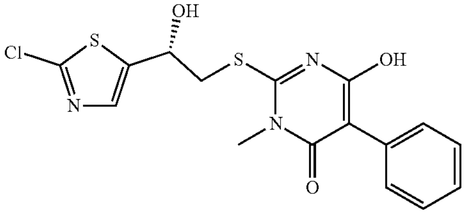

in an enantiomeric excess of at least 55% ee, preferably at least 60% ee, more preferably at least 70% ee, in particular at least 80% ee and specifically at least 90% ee. This is then reacted with an activating agent as described above.

The intramolecular nucleophilic attack proceeds predominantly from the reverse side to the OH leaving group, and thus with inversion of configuration at the asymmetric carbon atom (given that nucleophile and nucleofuge have the same priority according to the Cahn-Ingold-Prelog rules, the absolute configuration also changes from R to S).

Reaction conditions which yield reaction mixtures in which the R enantiomer of the compound 2 predominates are described above in context with step (a).

After completion of the reaction, the pyrimidinone of the formula (I) in enantiomerically enriched form is generally isolated from the reaction mixture. Isolation typically comprises steps suitable for precipitating the compound (I). For instance, the solvent can be partially removed, optionally under reduced pressure, upon which the desired compound (I) precipitates. Depending on the temperature applied for partially removing the solvent, on the amount of solvent removed and of course on the nature of the solvent, it might be expedient to cool the residual mixture, where cooling can occur continually or stepwise. Alternatively or additionally, a further solvent in which compound (I) has low solubility can be added, expediently after partial removal of the reaction solvent, upon which compound (I) precipitates; as the case may be after cooling (again continually or stepwise). Suitable solvents in which compound (I) has low solubility are for example aromatic hydrocarbons, such as benzene, toluene, trifluorotoluene, the xylenes (i.e. 1,2-xylene, 1,3-xylene or 1,4-xylene), chlorobenzene or dichlorobenzene; $C_1$-$C_4$-alkyl acetates, such as methyl acetate, ethyl acetate, n-propyl acetate and isopropyl acetate; $C_1$-$C_4$-alkanols, such as methanol, ethanol, n-propanol, isopropanol, n-butanol, sec-butanol, isobutanol and tert-butanol; glycols, such as ethylene glycol, propylene glycol, diethylene glycol and triethylene glycol; glycerol, water or mixtures of the aforementioned solvents.

The precipitate can be isolated by usual methods, such as filtration, centrifugation, sedimentation and removal of the supernatant etc., where filtration is preferred. The filter cake can be further purified by washing with suitable solvents, such as the above-listed solvent with low solubility for compound (I).

If desired, the catalyst can be recycled. For this purpose, the catalyst is for example recovered from the mother liquor of the precipitate of the compound of formula (I), e.g. the filtrate, centrifugate or supernatant; if desired purified and then used in step (a). The most straightforward way of recycling the catalyst is the use of the mother liquor of the precipitate (e.g. the filtrate, centrifugate or supernatant) in step (a), optionally after concentration. Alternatively, only the transition metal is recovered, and not the complete catalyst. The metal can for example be recovered by adsorption on a suitable adsorbent material, such as charcoal or a resin. To this end, the adsorbent material is added to said mother liquor. On a larger scale, the mother liquor can alternatively be passed once or several times through one or more columns filled with adsorbent. Separation of the metal from the adsorbent can be done by elution (especially when a resin is used), but generally, the adsorbent material is simply burnt. The metal can then be refined and converted into the desired catalyst or catalyst precursor by known methods and used again in step (a). Alternatively, the transition metal can be recovered from the mother liquor (optionally after neutralization) by removing the solvent of this phase and burning of the remainder. The metal can then be refined and converted into the desired catalyst or catalyst precursor by known methods and used again in the reduction process. The catalyst can also be first extracted from the mother liquor into a suitable organic solvent (e.g. into one with a lower boiling point, the removal of which is less energy-consuming), which is then subjected to the described treatment, optionally after neutralization.

The compound 1 is obtainable, for example, by reaction of N-methylthiourea with an alkyl 2-phenylmalonate to 6-hydroxy-3-methyl-5-phenyl-2-sulfanyl-pyrimidin-4-one or the corresponding thiolate and reaction thereof with 2-chloro-1-(2-chlorothiazol-5-yl)ethanone.

These reactions are described in EP application no. 21153040.7.

N-methylthiourea and alkyl 2-phenylmalonates are commercially available. 2-Chloro-1-(2-chlorothiazol-5-yl)ethanone can be prepared, for example, as described in WO 2018/197541 or WO 2018/202654 by reaction of 2-chlorothiazole with a Grignard reagent to the corresponding chloro-(2-chlorothiazol-5-yl) magnesium species and reaction thereof with 2-chloro-N-methoxy-N-methyl-acetamide. Alternatively, the compound 3 can be prepared from thiourea according the method described by T. Chalopin et al. in Org. Biomol. Chem., 2016, 14, 3913-3925.

The present method leads to the compound (I) in high yields and high stereoselectivity.

The present invention is further illustrated in the following examples.

EXAMPLES

Abbreviations:
DMAC N,N-dimethylacetamide
DMF N,N-dimethylformamide
DMSO dimethylsulfoxide
EtOAc ethyl acetate
Me-THF 2-methyltetrahydrofuran
THE tetrahydrofuran
TEA triethylamine
r.t. room temperature
t time
d day(s)
h hour(s)
min minute(s)
rt retention time

Example 1: Preparation of (3R)-3-(2-chlorothiazol-5-yl)-8-methyl-7-oxo-6-phenyl-2,3-dihydrothiazolo[3,2-a]pyrimidin-4-ium-5-olate 1.1 Preparation of 2-[2-(2-chlorothiazol-5-yl)-2-oxo-ethyl]sulfanyl-6-hydroxy-3-methyl-5-phenyl-pyrimidin-4-one In a 20 L jacketed reactor, a solution of N-methylthiourea (778 g, 8.38 mol) and $NaOCH_3$ (1584 g, 8.79 mol, 30 wt % solution in methanol) and methanol (384 g, 12 mol) under $N_2$ was warmed to an internal temperature of 65° C. Then diethyl 2-phenylmalonate (2121 g, 8.79 mol) was dosed over 30 min, and the pump was washed with methanol (384 g, 12 mol). The reaction was then stirred for 4 h at an internal temperature of 65° C., and then for 18 h at 50° C. Over this time a suspension formed. Then a solution of 2-chloro-1-(2-chlorothiazole-5-yl)ethanone (1859 g, 9.00 mol) in ethanol (8.050 g, 175 mol) was dosed over 30 min. The reaction was stirred 75 min at 50° C., and a large precipitation of solid occurred. At this point ethanol (2.300 g, 50 mol) was added, and the stirring speed was increased. The reaction was stirred at 50° C. a further 36 h and then reaction was then cooled to 20° C. over 16 h. The formed solid was then isolated via filtration in three 4 L fritted funnels. Each filtercake was washed with 500 mL of ethanol. The filtercake was then returned to the 20 L reactor and slurried with 15 L of water at 75° C. for 1 h. The slurry was then filtered in two 4 L fritted funnels, and each filtercake washed three times with 500 mL of room temperature water, and then dried at 80° C. and 5 mbar in a vacuum drying oven. After drying 3040 g (91%) of the title compound in form of a brown solid in 99 wt % purity were isolated.

$^1$H NMR (400 MHz, DMSO-d6): δ=8.75 (s, 1H), 7.15-7.45 (m, 5H), 4.9 (s, 2H), 3.46 (s, 3H).

1.2 Preparation of (3R)-3-(2-chlorothiazol-5-yl)-8-methyl-7-oxo-6-phenyl-2,3-dihydrothiazolo[3,2-a]pyrimidin-4-ium-5-olate 25.3 g (99%, 1.00 eq) of 2-[2-(2-chlorothiazol-5-yl)-2-oxo-ethyl]sulfanyl-6-hydroxy-3-methyl-5-phenyl-pyrimidin-4-one were dissolved in 165 g of dimethyl acetamide, cooled to −5° C. and a nitrogen sparge was applied. 8.3 g (99%, 1.00 eq) of diisopropyl ethylamine and 3.5 g (100%, 1.20 eq) of formic acid were subsequently added, followed by a solution of 0.13 g (94%, 0.003 eq) of the preformed catalyst Rh(III)ClCp*·(1S,2S-TsDPEN) (obtained by reacting 1 equivalent of [Rh(III)$Cl_2$Cp*]$_2$ with 2 equivalents of 1S,2S-TsDPEN in the presence of 4 equivalents of triethylamine) in 10 g of dimethyl acetamide. The reaction mixture was stirred for 2 h and 13.6 g (95%, 1.30 eq) of diethyl chlorophosphite were added. The reaction mixture was warmed up to 30° C. in 3 h, then to 80° C. in 2.5 h. Distillation of the solvent (−154 g) was performed by decreasing the pressure to 45 mbar, then the vacuum was broken and 72 g of ethyl acetate were dosed. The temperature was cooled to 20° C. in 4 h. The precipitate was filtered, washed with ethyl acetate (2×63 g) and water (2×63 g) and finally dried in vacuo (~100° C.). 20.6 g (>99% ee, 99%, 83% yield) of (3R)-3-(2-chlorothiazol-5-yl)-8-methyl-7-oxo-6-phenyl-2,3-dihydrothiazolo[3,2-a]pyrimidin-4-ium-5-olate were obtained as off-white solid.

$^1$H NMR (400 MHz, DMSO-d6): δ=7.96 (s, 1H), 7.6 (d, J=7.5 Hz, 1H), 7.21-7.26 (m, 2H), 7.06-7.11 (m, 1H), 6.48 (d, J=8.1 Hz, 1H), 4.25-4.32 (m, 1H), 3.94 (d, J=12 Hz, 1H), 3.42, (s, 3H).

m/z (M+H$^+$)=378

Example 2: Preparation of (3R)-3-(2-chlorothiazol-5-yl)-8-methyl-7-oxo-6-phenyl-2,3-dihydrothiazolo [3,2-a]pyrimidin-4-ium-5-olate 34.1 g (99%, 1.00 eq) of 2-[2-(2-chlorothiazol-5-yl)-2-oxo-ethyl]sulfanyl-6-hydroxy-3-methyl-5-phenyl-pyrimidin-4-one were dissolved in 216 g of dimethyl acetamide, cooled to −5° C. and a nitrogen sparge was applied. 6.7 g of formic acid (1.10 eq)/triethyl amine (0.27 eq) mixture (molar ratio 4.1:1) were added, followed by a solution of 0.47 g (94%, 0.003 eq) of the preformed catalyst Rh(III)ClC*·(1S, 2S-TsDPEN) (obtained by reacting 1 equivalent of [Rh(III) $Cl_2$Cp*]$_2$ with 2 equivalents of 1S,2S-TsDPEN in the presence of 4 equivalents of triethylamine) in 20 g of dimethyl acetamide. The reaction mixture was stirred for 1.5 h and 15.5 g (95%, 1.10 eq) of diethyl chlorophosphite were added. The reaction mixture was warmed up to 25° C. in 2.5 h, then to 80° C. in 2.5 h. Distillation of the solvent (−205 g) was performed by decreasing the pressure to 45 mbar, then the vacuum was broken and 87 g of ethyl acetate were dosed. The temperature was cooled to 20° C. in 4 h. The precipitate was filtered, washed with ethyl acetate (2×85 g) and water (2×85 g) and finally dried in vacuo (~100° C.). 28.8 g (>99% ee, 99%, 87% yield) of (3R)-3-(2-chlorothiazol-5-yl)-8-methyl-7-oxo-6-phenyl-2,3-dihydrothiazolo[3,2-a]pyrimidin-4-ium-5-olate were obtained as off-white to beige solid.

Example 3: Preparation of (3S)-3-(2-chlorothiazol-5-yl)-8-methyl-7-oxo-6-phenyl-2,3-dihydrothiazolo [3,2-a]pyrimidin-4-ium-5-olate 29.9 g (99%, 1.00 eq) of 2-[2-(2-chlorothiazol-5-yl)-2-oxo-ethyl]sulfanyl-6-hydroxy-3-methyl-5-phenyl-pyrimidin-4-one were dissolved in 230 g of dimethyl acetamide, cooled to −5° C. and a nitrogen sparge was applied. A mixture of 5.2 g formic acid (1.50 eq)/3.5 g diisopropylethylamine (0.36 eq) was added, followed by a solution of 0.17 g (92%, 0.003 eq) of the preformed catalyst Ir(Ill)ClCp*-(1R,2R-MsDPEN) (obtained by reacting 1 equivalent of [Ir(III)$Cl_2$Cp*]$_2$ with 2.1 equivalents of 1R,2R-MsDPEN in the presence of 4 equivalents of triethylamine) in 10 g of dimethyl acetamide. The reaction mixture was stirred for 9 h and 21.0 g (95%, 1.70 eq) of diethyl chlorophosphite were added. The reaction mixture was warmed up to 30° C. in 3 h, then to 80° C. in 2.5 h. Distillation of the solvent (−207 g) was performed by decreasing the pressure to 45 mbar, then the vacuum was broken and 82 g of ethyl acetate were dosed. The temperature was cooled to 20° C. in 4 h and stirred overnight. The precipitate was filtered, washed with ethyl acetate (2×75 g) and water (2×75 g) and finally dried in vacuo (~100° C.). 23.5 g (>99% ee, >99%, 83% yield) of (3S)-3-(2-chlorothiazol-5-yl)-8-methyl-7-oxo-6-phenyl-2,3-dihydrothiazolo[3,2-a]pyrimidin-4-ium-5-olate were obtained as off-white solid.

Example 4: Preparation of (3R)-3-(2-chlorothiazol-5-yl)-8-methyl-7-oxo-6-phenyl-2,3-dihydrothiazolo [3,2-a]pyrimidin-4-ium-5-olate 2-[2-(2-chlorothiazol-5-yl)-2-oxo-ethyl]sulfanyl-6-hydroxy-3-methyl-5-phenyl-pyrimidin-4-one (30 g, 75.48 mmol, 1 eq.) was added to a solution of dimethyl acetamide (165 g) and diisopropyl ethylamine (11.83 g, 90.58 mmol, 1.20 eq) at −5° C. and a nitrogen sparge was applied. Then formic acid (4.21 g, 90.58 mmol, 1.20 eq), followed by a solution of [(4S,5S)-2-chloro-1-methylsulfonyl-4,5-diphenyl-1,3-diaza-2Δ4-rhodacyclopent-2-yl]; 1,2,3,4,5-pentamethylcyclopentadienyl (formed in situ in said solution by mixing [Rh(III)$Cl_2$Cp*]$_2$, 1S,2S-MsDPEN and Hunig's base (diisopropylethylamine) used in a molar ratio of 1:3:7) (assuming 100% conversion: 0.084 g of catalyst, 0.151 mmol, 0.002 eq) in 10 g of dimethyl acetamide were sequentially added. The reaction mixture was stirred for 4 h and then diethyl chlorophosphite (15.7 g, 83.30 mmol, 1.1 eq) was added. The reaction mixture was warmed to 30° C. over 3 h, then to 80° C. over 2.5 h. The pressure was then reduced to 45 mbar, and 154 g of dimethyl acetamide was removed by distillation, then the vacuum was broken and 72 g ethyl acetate was added over 1 h. The temperature was then reduced to 20° C. over 4 h, during which time a suspension formed. The solid was isolated by filtration, washed with ethyl acetate (2×63 g) and water (2×63 g) and finally dried in vacuo at 100° C. to afford 24.2 g (>99% ee, 85% yield) of (3R)-3-(2-chlorothiazol-5-yl)-8-methyl-7-oxo-6-phenyl-2,3-dihydrothiazolo[3,2-a]pyrimidin-4-ium-5-olate was obtained as off-white solid.

Example 5: Preparation of (3R)-3-(2-chlorothiazol-5-yl)-8-methyl-7-oxo-6-phenyl-2,3-dihydrothiazolo [3,2-a]pyrimidin-4-ium-5-olate 2-[2-(2-Chlorothiazol-5-yl)-2-oxo-ethyl]sulfanyl-6-hydroxy-3-methyl-5-phenyl-pyrimidin-4-one (5.0 g, 12.65 mmol, 1 eq.) was dissolved in dimethyl formamide (36.3 g), then cooled to 0° C. and a nitrogen sparge was applied. A solution of the preformed catalyst [(4S,5S)-2-chloro-1-methylsulfonyl-4,5-diphenyl-1,3-diaza-2Δ4-rhodacyclopent-2-yl]; 1,2,3,4,5-pentamethylcyclopentadienyl (0.051 g, 0.08 mmol, 0.006 eq) in 15 ml of dimethyl formamide was added, followed by addition of 0.98 g of a formic acid (1.10 eq)/triethyl amine (0.27 eq) mixture (molar ratio 4.1:1). The reaction mixture was stirred for 3 h and then diethyl chlorophosphite (3.5 g, 21.51 mmol, 1.7 eq) was added. The reaction mixture was warmed to room temperature overnight. The pressure was then reduced to 15 mbar (50° C.), and dimethyl formamide was distilled off until 16 g of the reaction mixture remained. 16 g of ethyl acetate were added over 0.5 h. The temperature was then reduced to 20° C. The solid was isolated by filtration, washed with ethyl acetate (2×12.5 g) and water (2×12.5 g) and finally dried in vacuo at 100° C. to afford 3.53 g (>99% ee, >99%, 76% yield) of (3R)-3-(2-chlorothiazol-5-yl)-8-methyl-7-oxo-6-phenyl-2,3-dihydrothiazolo[3,2-a]pyrimidin-4-ium-5-olate as an off-white solid.

Example 6: Preparation of (3R)-3-(2-chlorothiazol-5-yl)-8-methyl-7-oxo-6-phenyl-2,3-dihydrothiazolo[3,2-a]pyrimidin-4-ium-5-olate 2-[2-(2-chlorothiazol-5-yl)-2-oxo-ethyl]sulfanyl-6-hydroxy-3-methyl-5-phenyl-pyrimidin-4-one (30 g, 75.48 mmol, 1 eq.) was added to a solution of dimethyl acetamide (120 g) and diisopropyl ethylamine (11.75 g, 90.58 mmol, 1.20 eq) at −5° C. and a nitrogen sparge was applied. Then formic acid (0.70 g, 15.07 mmol, 0.20 eq), followed by a solution of [(4S,5S)-2-chloro-1-methylsulfonyl-4,5-diphenyl-1,3-diaza-2Δ4-rhodacyclopent-2-yl]; 1,2,3,4,5-pentamethylcyclopentadienyl (formed in situ in said solution by mixing $[Rh(III)Cl_2Cp^*]_2$, 1S,2S-MsDPEN and Hunig's base used in a molar ratio of 1:3:7) (assuming 100% conversion: 0.084 g of catalyst, 0.151 mmol, 0.002 eq) in 10 g of dimethyl acetamide were sequentially added. Then formic acid (3.51 g, 75.59 mmol, 1.00 eq) was dosed in 30 min. The reaction mixture was stirred for 4 h and then diethyl chlorophosphite (15.7 g, 83.30 mmol, 1.1 eq) was added. The reaction mixture was warmed to 30° C. over 3 h, then to 80° C. over 2.5 h. The pressure was then reduced to 45 mbar, and 113 g of dimethyl acetamide was removed by distillation, then the vacuum was broken and the temperature was then reduced to 20° C. over 4 h. 80 g of ethanol were added over 2 h. The solid was isolated by filtration and washed with ethanol (1×75 g). The solid was re-suspended in 96 g ethanol/water (1:1) at 80° C. for 50 h, filtered, washed with water (2×50 g) and finally dried in vacuo at 100° C. to afford 22.8 g (>99% ee, >99%, 80% yield) of (3R)-3-(2-chlorothiazol-5-yl)-8-methyl-7-oxo-6-phenyl-2,3-dihydrothiazolo[3,2-a]pyrimidin-4-ium-5-olate as an off-white solid.

Following further reaction conditions for step b) were tested and yielded similar results:

| AA[10] | Solvent | Conditions |
|---|---|---|
| $PCl_3$ | $CH_3CN$ | 25° C., 16 h |
| $(EtO)_2PCl$ | $CH_3CN$ | 25° C., 16 h |
| $MeOPCl_2$ | $CH_3CN$ | 25° C., 16 h |
| $EtOPCl_2$ | $CH_3CN$ | 25° C., 16 h |
| $(EtO)_2P(O)Cl$ | $CH_3CN$ | 25° C., 16 h |
| $(MeO)_2P(O)Cl$ | $CH_3CN$ | 25° C., 16 h |
| $P(O)Cl_3$ | $CH_3CN$ | 25° C., 16 h |
| $PCl_3$ | $CH_2Cl_2$ | 25° C., 2 h |

-continued

| AA[10] | Solvent | Conditions |
|---|---|---|
| $(EtO)_2PCl$ | $CH_2Cl_2$ | 25° C., 2 h |
| $MeOPCl_2$ | $CH_2Cl_2$ | 25° C., 2 h |
| $EtOPCl_2$ | $CH_2Cl_2$ | 25° C., 2 h |
| PPA | $CH_2Cl_2$ | 25° C., 17 h |
| $P_{4010}$ | $CH_2Cl_2$ | 25° C., 17 h |
| $SO_3$*Pyr | $CH_2Cl_2$ | 25° C., 17 h |
| $SO_3$*$NEt_3$ | $CH_2Cl_2$ | 25° C., 17 h |
| $SO_3$*DMF | $CH_2Cl_2$ | 25° C., 17 h |
| $PPh_3$/NCS | $CH_2Cl_2$ | 25° C., 23 h |
| $PPh_3$/DEAD | $CH_2Cl_2$ | 25° C., 23 h |
| $PPh_3$/DIAD | $CH_2Cl_2$ | 25° C., 23 h |
| CMDMC + TEA | $CH_2Cl_2$ | 25° C., 24 h |
| CMDMC | $CH_2Cl_2$ | 25° C., 24 h |
| DMF-DMA/$BF_3$ | $CH_2Cl_2$ | 25° C., 24 h |
| $PCl_3$ | MTBE | 25° C., 16 h |
| $PCl_3$ | Toluene | 25° C., 16 h |
| $PCl_3$ | Dioxan | 25° C., 16 h |
| $PCl_3$ | Chlorobenzene | 25° C., 16 h |
| $PCl_3$ | THF | 25° C., 16 h |
| $PCl_3$ | THF/$H_2O$ (1 eq[11]) | 25° C., 2 h |
| $PCl_3$ | THF/$H_2O$ (1.5 eq[11]) | 25° C., 2 h |
| $PCl_3$ | THF/$H_2O$ (2 eq[11]) | 25° C., 2 h |
| $PCl_3$ | THF/$H_2O$ (2.5 eq[11]) | 25° C., 2 h |
| $PCl_3$ | Ethyl acetate | 25° C., 16 h |
| $PCl_3$ | $CH_2Cl_2$ | −15° C., 6 h |
| $PCl_3$ | $CH_2Cl_2$ | 25° C., 19 h |
| $PCl_3$ | $CH_2Cl_2$ | 0° C., 24 h |
| $(EtO)_2PCl$ | $CH_2Cl_2$ | 0° C., 24 h |
| $MeOPCl_2$ | $CH_2Cl_2$ | 0° C., 24 h |
| $EtOPCl_2$ | $CH_2Cl_2$ | 0° C., 24 h |
| $MeOPCl_2$ | $CH_3CN$ | 0° C., 24 h |
| $MeOPCl_2$ | THF | 0° C., 24 h |
| $SO_3$*DMF | $CH_2Cl_2$ | 25° C., 24 h |
| CDI | $CH_3CN$ | 0-45° C., 3 d |
| $POCl_3$ | $CH_3CN$ | 0° C., 15 h |
| $CH_3S(O)_2Cl$ | $CH_3CN$ | 0° C., 2 d |

Me = methyl;
Et = ethyl;
Ph = phenyl;
PPA = polyphosphoric acid;
Pyr = pyridine;
DMF = dimethylformamide;
DMA = dimethylamide;
NCS = N-chlorosuccinimide;
CMDMC = Vilsmeyer reagent;
(chloromethylene)-N,N-dimethyliminium chloride ($CHCl{=}N(CH_3)_2{}^+Cl^-$);
TEA = triethylamine;
MTBE = methyl tert-butyl ether;
THF = tetrahydrofuran
[10]AA = activating agent
[11]in this context, 1 eq is the weight equivalent to the starting compound.

Example 7: Preparation of (3R)-3-(2-chlorothiazol-5-yl)-8-methyl-7-oxo-6-phenyl-2,3-dihydrothiazolo[3,2-a]pyrimidin-4-ium-5-olate Similarly to example 6, 2-[2-(2-chlorothiazol-5-yl)-2-oxo-ethyl]sulfanyl-6-hydroxy-3-methyl-5-phenyl-pyrimidin-4-one was reacted with 10.93 mmol (1.1 eq.) of formic acid in the presence of 9.94 mmol (1 eq.) of diisopropylethylamine as base and 0.3 mmol (3 mol %) of the catalyst RuClmes-(1S,2S-TsDPEN) (obtained by reacting $[RuCl_2(mes^8)]_2$ with 1S,2S-TsDPEN) in 70 g of chloroform at 0° C.; and then with 1.8 eq. of diethyl chlorophosphite at 10° C. The title compound was obtained in 77% yield and >99% ee.

Example 8: Preparation of (3S)-3-(2-chlorothiazol-5-yl)-8-methyl-7-oxo-6-phenyl-2,3-dihydrothiazolo[3,2-a]pyrimidin-4-ium-5-olate Similarly to example 6, 2-[2-(2-chlorothiazol-5-yl)-2-oxo-ethyl]sulfanyl-6-hydroxy-3-methyl-5-phenyl-pyrimidin-4-one was reacted with 14.9 mmol (1.5 eq.) of formic acid in the presence of 14.9 mmol (1.5 eq.) of diisopropylethylamine as base and 0.4 mmol (4 mol %) of the catalyst RuClmes-(1R,2R-CsDPEN) (obtained by reacting $[RuCl_2(mes^8)]_2$ with 1R,2R-CsDPEN; to be more precise with N-[(1R,2R)-2-amino-1,2-diphenyl-ethyl]-1-[(1S,4R)-7,7-dimethyl-2-oxo-norbornan-1-yl]methanesulfonamide) in 46 g of DMAC at 20° C.; and then with 1.8 eq. of diethyl chlorophosphite (added in two portions of 1.5 and 0.3 eq.). The title compound was obtained in 80% yield and 83% ee.

Example 9: Preparation of (3S)-3-(2-chlorothiazol-5-yl)-8-methyl-7-oxo-6-phenyl-2,3-dihydrothiazolo [3,2-a]pyrimidin-4-ium-5-olate Similarly to example 6, 2-[2-(2-chlorothiazol-5-yl)-2-oxo-ethyl]sulfanyl-6-hydroxy-3-methyl-5-phenyl-pyrimidin-4-one was reacted with 10.93 mmol (1.1 eq.) of formic acid in the presence of 9.94 mmol (1 eq.) of diisopropylethylamine as base and 0.2 mmol (2 mol %) of the catalyst RuClmes-(1R,2R-CsDPEN) (obtained by reacting $[RuCl_2(mes^8)]_2$ with 1R,2R-CsDPEN; to be more precise with N-[(1R,2R)-2-amino-1,2-diphenyl-ethyl]-1-[(1S,4R)-7,7-dimethyl-2-oxo-norbornan-1-yl]methanesulfonamide) in 46 g of DMAC at 20° C.; and then with 1.8 eq. of diethyl chlorophosphite (added in two portions of 1.5 and 0.3 eq.). The title compound was obtained in 80% yield and 85% ee.

Example 10: Preparation of (3R)-3-(2-chlorothiazol-5-yl)-8-methyl-7-oxo-6-phenyl-2,3-dihydrothiazolo[3,2-a]pyrimidin-4-ium-5-olate (vacuum, addition to diethyl chlorophosphite)

2-[2-(2-Chlorothiazol-5-yl)-2-oxo-ethyl]sulfanyl-6-hydroxy-3-methyl-5-phenyl-pyrimidin-4-one (30.5 g, 76.64 mmol, 1 eq.) was added to a solution of dimethyl acetamide (165 g) and diisopropyl ethylamine (9.90 g, 76.64 mmol, 1.00 eq) and formic acid (3.88 g, 84.30 mmol, 1.10 eq) at −5° C. Then vacuum was applied (50 mbar), followed by addition of a solution of RhClCp*·(1S,2S-CsDPEN) (formed in situ in said solution by mixing $[Rh(III)Cl_2Cp^*]_2$, 1S,2S-CsDPEN (to be more precise N-[(1S,2S)-2-amino-1,2-diphenyl-ethyl]-1-[(1S,4R)-7,7-dimethyl-2-oxo-norbornan-1-yl]methanesulfonamide) and diisopropylethylamine used in a molar ratio of 1:3:7) (assuming 100% conversion: 0.107 g of catalyst, 0.153 mmol, 0.002 eq) in 10 g of dimethyl acetamide. The reaction mixture was stirred for 3 h, the vacuum was broken, and the mixture was then added to a solution of diethyl chlorophosphite (15.60 g, 99.63 mmol, 1.3 eq) in dimethyl acetamide (36 g) at 20° C. The reaction mixture was stirred for 5 h, then warmed to 80° C. over 3 h and kept for 3 h. The pressure was then reduced to 20 mbar, and 167 g of dimethyl acetamide was removed by distillation. Then the vacuum was broken, the mixture cooled down to 60° C. and 86 g methanol was added over 1 h. The temperature was then reduced to 0° C. over 4 h, during which time a suspension formed. The solid was isolated by filtration, washed with methanol (1×74 g) and water (1×69 g) and finally dried in vacuo at 100° C. to afford 24.0 g (>99% ee, 83% yield) of (3R)-3-(2-chlorothiazol-5-yl)-8-methyl-7-oxo-6-phenyl-2,3-dihydrothiazolo[3,2-a]pyrimidin-4-ium-5-olate as off-white solid.

Example 11: Preparation of (3R)-3-(2-chlorothiazol-5-yl)-8-methyl-7-oxo-6-phenyl-2,3-dihydrothiazolo[3,2-a]pyrimidin-4-ium-5-olate 2-[2-(2-Chlorothiazol-5-yl)-2-oxo-ethyl]sulfanyl-6-hydroxy-3-methyl-5-phenyl-pyrimidin-4-one (30.0 g, 75.18 mmol, 1 eq.) was added to a solution of dimethyl acetamide (120 g), cooled to −5° C. and a nitrogen sparge was applied. Then diisopropyl ethylamine (9.72 g, 75.18 mmol, 1.00 eq) and formic acid (3.85 g, 82.69 mmol, 1.10 eq) were successively added at −5° C., followed by addition of a solution of RhClCp*·(1S,2S-CsDPEN) (formed in situ in said solution by mixing $[Rh(III)Cl_2Cp^*]_2$, 1S,2S-CsDPEN (to be more precise N-[(1S,2S)-2-amino-1,2-diphenyl-ethyl]-1-[(1S,4R)-7,7-dimethyl-2-oxo-norbornan-1-yl]methanesulfonamide) and diisopropylethylamine used in a molar ratio of 1:3:7 in DMAC) (assuming 100% conversion: 0.105 g of catalyst, 0.15 mmol, 0.002 eq). The reaction mixture was stirred for 2 h. Diethyl chlorophosphite (16.78 g, 97.73 mmol, 1.3 eq) was added at −5° C. and the reaction mixture was warmed to 25° C. and stirred for 5 h, then warmed to 80° C. over 3 h and kept for 3 h. The pressure was then reduced to 35-45 mbar, and dimethyl acetamide was removed by distillation. Then the vacuum was broken, the mixture (71 g) cooled down to 60° C. and 85 g methanol was added over 1 h. The temperature was then reduced to 20° C. over 3 h. The solid was isolated by filtration, washed with methanol (1×71 g) and water (1×71 g) and finally dried in vacuo at 100° C. to afford 24.74 g (>99% ee, 85% yield) of (3R)-3-(2-chlorothiazol-5-yl)-8-methyl-7-oxo-6-phenyl-2,3-dihydrothiazolo[3,2-a]pyrimidin-4-ium-5-olate as off-white solid.

Example 12: Various Reaction Conditions for the Preparation of 2-R Required for the Preparation of (3S)-3-(2-chlorothiazol-5-yl)-8-methyl-7-oxo-6-phenyl-2,3-dihydrothiazolo[3,2-a]pyrimidin-4-ium-5-olate Further reaction conditions for step a) were tested. The reaction was carried out similarly to the first part of the above examples (i.e. proceeding before reacting with the activating agent), using however 1 g of starting compound, DMF (2 ml) as solvent, and the catalysts and conditions compiled in the following table. The catalysts were either used in preformed form by reaction of the indicated catalyst precursor and asymmetric ligand or were generated in situ by adding to the reaction mixture the indicated catalyst precursor and asymmetric ligand. The reaction was carried out at room temperature, except for examples 13 to 17, which were carried out at 0° C.

| No. | cat. prec.[1] | asym. lig.[2] | in situ/ preformed[3] | amount cat. [mol %][4] | HCOOH:amine[5]; HCOOH amount | Conversion [%] | (2-R) % ee |
|---|---|---|---|---|---|---|---|
| 1 | $[Ir(III)Cl_2Cp^*]_2$ | 1R,2R-TsDPEN | i.s. | 4 | $HC(O)O^-$ $Na^+/H_2O^6$; 5 eq. | 97 | 90 |
| 2 | $[Ir(III)Cl_2Cp^*]_2$ | 1R,2R-MsDPEN | i.s. | 4 | $HC(O)O^-$ $Na^+/H_2O^6$; 5 eq. | 95 | 92 |
| 3 | $[Ir(III)Cl_2Cp^*]_2$ | 1R,2R-MsDPEN | i.s. | 2 | 1.1:1; 1.2 eq. | 97 | 90 |

-continued

| No. | cat. prec.[1] | asym. lig.[2] | in situ/ preformed[3] | amount cat. [mol %][4] | HCOOH:amine[5]; HCOOH amount | Conversion [%] | (2-R) % ee |
|---|---|---|---|---|---|---|---|
| 4 | $[Ir(III)Cl_2Cp^*]_2$ | 1R,2R-MsDPEN | i.s. | 1 | 1.1:1; 1.2 eq. | 97 | 90 |
| 5 | $[Ir(III)Cl_2Cp^*]_2$ | 1R,2R-MsDPEN | pre. | 1 | 1.1:1; 1.2 eq. | 97 | 90 |
| 6 | $[Ir(III)Cl_2Cp^*]_2$ | 1R,2R-$CF_3$TsDPEN | pre. | 1 | 1.1:1; 1.2 eq. | 91 | 92 |
| 7 | $[Ir(III)Cl_2Cp^*]_2$ | 1R,2R-MeMsDPEN | i.s. | 1 | 1.1:1; 1.2 eq. | 98 | 96 |
| 8 | $[Ir(III)Cl_2Cp^*]_2$ | 1R,2R-MeMsDPEN | pre. | 0.3 | 1.1:1; 1.2 eq. | 99 | 96 |
| 9 | C-3-tethr-RuCl-1R,2R-TsDPEN[7] | | pre. | 4 | 4.5:1; 2.7 eq. | 99 | 90 |
| 10 | [RuCl$_2$(mes[8])]$_2$ | 1R,2R-TsDPEN | pre. | 4 | 1.1:1; 1.2 eq. | 92 | 82 |
| 11 | [RuCl$_2$(mes[8])]$_2$ | 1R,2R-TsDPEN | pre. | 2 | 1.1:1; 1.2 eq. | 92 | 80 |
| 12 | [RuCl$_2$(cym[9])]$_2$ | 1R,2R-MeMsDPEN | pre. | 1 | 1.1:1; 1.2 eq. | 98 | 78 |
| 13 | $[Ir(III)Cl_2Cp^*]_2$ | 1R,2R-MsDPEN | pre. | 1 | 4.1:1; 1.5 eq. | 100 | 96 |
| 14 | $[Ir(III)Cl_2Cp^*]_2$ | 1R,2R-MeMsDPEN | pre. | 1 | 4.1:1; 1.5 eq. | 100 | 95 |
| 15 | $[Ir(III)Cl_2Cp^*]_2$ | 1R,2R-MeTsDPEN | pre. | 1 | 4.1:1; 1.5 eq. | 95 | 95 |
| 16 | $[Rh(III)Cl_2Cp^*]_2$ | 1R,2R-TsDPEN | pre. | 1 | 4.1:1; 1.5 eq. | 100 | 95 |
| 17 | $[Rh(III)Cl_2Cp^*]_2$ | 1R,2R-MsDPEN | pre. | 1 | 4.1:1; 1.5 eq. | 100 | 95 |

[1]cat. prec. = catalyst precursor

[2]asym. lig. = asymmetric ligand

[3]i.s. = catalyst formed in situ (from the indicated catalyst precursor and asymmetric ligand); pre. = catalyst preformed (from the indicated catalyst precursor and asymmetric ligand)

[4]amount of catalyst (calculated as amount of the metal) in mol-%, relative to the amount (in mol) of 2-[2-(2-chlorothiazol-5-yl)-2-oxo-ethyl]sulfanyl-6-hydroxy-3-methyl-5-phenyl-pyrimidin-4-one

[5]molar ratio formic acid:amine. In case that a formate is used instead of formic acid, this is indicated and no molar ratio is given; see [6]. The amount of HCOOH used is given in molar equivalents, relative to the amount (in mol) of 2-[2-(2-chlorothiazol-5-yl)-2-oxo-ethyl]sulfanyl-6-hydroxy-3-methyl-5-phenyl-pyrimidin-4-one used.

[6]instead of formic acid/amne, sodium formate and water were used

[7]C-3-tethr-RuCl-1R,2R-TsDEPEN =

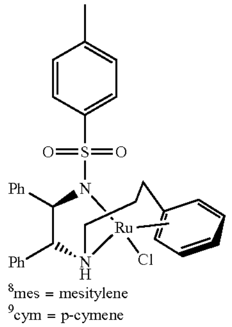

[8]mes = mesitylene

[9]cym = p-cymene

Example 13: Various Reaction Conditions for the Preparation of 2-S Required for the Preparation of (3R)-3-(2-chlorothiazol-5-yl)-8-methyl-7-oxo-6-phenyl-2,3-dihydrothiazolo[3,2-a]pyrimidin-4-ium-5-olate Further reaction conditions for step a) were tested. The reaction was carried out similarly to the first part of the above examples (i.e. proceeding before reacting with the activating agent), using however 400 mg of starting compound and 7 ml of solvent, the solvent, catalyst and conditions being as compiled in the following table. The catalysts were either used in preformed form by reaction of the indicated catalyst precursor and asymmetric ligand or were generated in situ by adding to the reaction mixture the indicated catalyst precursor and asymmetric ligand. The reaction was carried out at room temperature, except for examples 18 and 19 (−5° C.) as well as examples 20, 22, 37, 39, 42, 45 and 47 (0° C.).

| No. | cat.[12] | amount cat. [mol %][4] | Solvent | HCOOH:amine[5]; HCOOH amount | Conversion [%] | (2-S) % ee |
|---|---|---|---|---|---|---|
| 18 | 1 | 0.3% | DMAC | 1.75:1; 2.8 eq. | 100 | 97 |
| 19 | 1 | 0.3% | DMAC | 2.8:1; 2.8 eq. | 100 | 97 |
| 20 | 2 | 4% | DMAC | 1.75:1; 2.8 eq. | 100 | 85 |
| 21 | 2 | 2% | DMF | 1.75:1; 2.8 eq. | 100 | 79 |

-continued

| No. | cat.[12] | amount cat. [mol %][4] | Solvent | HCOOH:amine[5]; HCOOH amount | Conversion [%] | (2-S) % ee |
|---|---|---|---|---|---|---|
| 22 | 2 | 4% | DMF | 1.75:1; 2.8 eq. | 100 | 84 |
| 23 | 2 | 4 | benzotrifluoride | 1.75:1; 2.8 eq. | 100 | n.d. |
| 24 | 2* | 4% | DMAC | 1.75:1; 2.8 eq. | 100 | 80 |
| 25 | 2* | 4% | EtOAc | 1.75:1; 2.8 eq. | 100 | 87 |
| 26 | 2* | 4% | $CHCl_3$ | 1.75:1; 2.8 eq. | 100 | 94 |
| 27 | 2* | 2% | $CHCl_3$ | 1.75:1; 2.8 eq. | 100 | 94 |
| 28 | 2* | 4% | $CH_2Cl_2$ | 1.75:1; 2.8 eq. | 100 | 89 |
| 29 | 2* | 4% | $CH_2Cl_2$ | 1.75:1; 2.8 eq. | 100 | 87 |
| 30 | 2* | 4% | Me-THF | 1.75:1; 2.8 eq. | 98 | 88 |
| 31 | 2* | 4 | dichloroethane | 1.75:1; 2.8 eq. | 100 | 86 |
| 32 | 2* | 4 | fluorobenzene | 1.75:1; 2.8 eq. | 100 | 89 |
| 33 | 2* | 4 | benzotrifluoride | 1.75:1; 2.8 eq. | 100 | n.d. |
| 34 | 2* | 4 | anisol | 1.75:1; 2.8 eq. | 100 | 88 |
| 35 | 2* | 4 | chlorobenzene | 1.75:1; 2.8 eq. | 100 | 90 |
| 36 | 3 | 4% | $CH_2Cl_2$ | 1.75:1; 2.8 eq. | 100 | 84 |
| 37 | 3 | 4% | $CH_2Cl_2$ | 1.75:1; 2.8 eq. | 100 | 84 |
| 38 | 3 | 2% | $CH_2Cl_2$ | 1.75:1; 2.8 eq. | 100 | 81 |
| 39 | 3 | 4% | DMAC | 1.75:1; 2.8 eq. | 100 | 80 |
| 40 | 4 | 4 | $CHCl_3$ | 1.75:1; 2.8 eq. | 100 | 94 |
| 41 | 4 | 4 | EtOAc | 1.75:1; 2.8 eq. | 91 | 86 |
| 42 | 4 | 4 | $CH_2Cl_2$ | 1.75:1; 2.8 eq. | 100 | 88 |
| 43 | 5 | 4 | $CH_2Cl_2$ | 1.75:1; 2.8 eq. | 100 | 90 |
| 44 | 6 | 4 | $CH_2Cl_2$ | 1.75:1; 2.8 eq. | 100 | 86 |
| 45 | 7 | 4 | dichloroethane | 1.75:1; 2.8 eq. | 100 | 93 |
| 46 | 7 | 4 | $CH_2Cl_2$ | 1.75:1; 2.8 eq. | 100 | 95 |
| 47 | 7 | 4 | EtOAc | 1.75:1; 2.8 eq. | 100 | 93 |

[12]catalyst:

Cat. 1: catalyst Rh(III)ClCp* (1S,2S-MsDPEN) of the following formula obtained by reacting [Rh(III)Cl2Cp*]$_2$ with 1S,2S-MsDPEN:

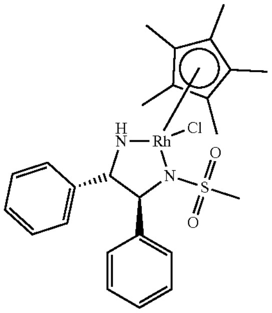

Cat. 2: catalyst RuClMes.(1S,2S-TsDPEN) of the following formula; preformed; obtained by reacting $[RuCl_2(mes^{8})]_2$ with 1S,2S-TsDPEN:

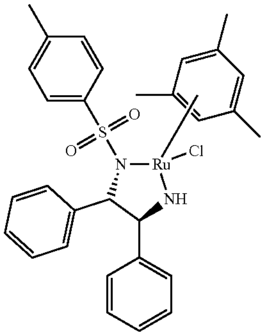

Cat. 2*: like 2, but formed in situ.

Cat. 3: catalyst RuClMes·(1S,2S-MsDPEN) of the following formula obtained by reacting $[RuCl_2(mes^{8})]_2$ with 1S,2S-MsDPEN:

-continued

| No. | cat.[12] | amount cat. [mol %][4] | Solvent | HCOOH:amine[5]; HCOOH amount | Conversion [%] | (2-S) % ee |
|---|---|---|---|---|---|---|

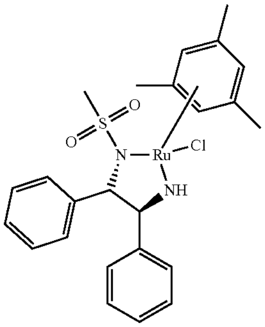

Cat. 4: catalyst RuClMes·(1S,2S-CsDPEN) obtained by reacting $[RuCl_2(mes^8)]_2$ with 1S,2S-CsDPEN (to be more precise with N-[(1S,2S)-2-amino-1,2-diphenyl-ethyl]-1-[(1S,4R)-7,7-dimethyl-2-oxo-norbornan-1-yl]methanesulfonamide Cat. 5: catalyst RuClMes·(1S,2S-TsDiOMeDPEN) of following formula, obtained by reacting $[RuCl_2(mes^8)]_2$ with N-[(1S,2S)-2-amino-1,2-bis(4-methoxyphenyl)ethyl]-4-methyl-benzenesulfonamide:

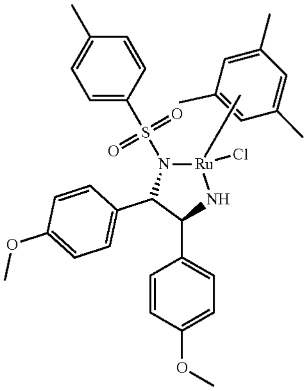

Cat. 6: catalyst RuClMes·(1S,2S-MesitylDPEN) of following formula obtained by reacting $[RuCl_2(mes^8)]_2$ with 1S,2S-MesitylDPEN

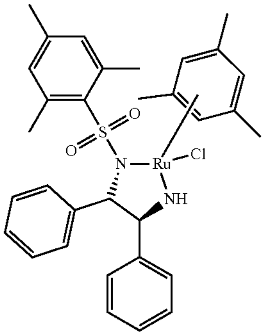

Cat. 7: catalyst RuClMes·(1S,2S-RsDPEN) of following formula obtained by reacting $[RuCl_2(mes^8)]_2$ with 1S,2S-RsDPEN

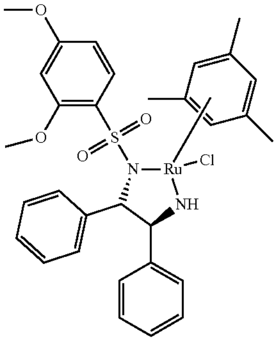

Example 14: Use of Various Stereoisomers of (1R,2R)-CsDPEN as Ligand in Hydrogenation Step (a)

To show that the configuration of the camphor moiety of the CsDPEN ligand has essentially no influence on the stereoselectivity in the hydrogenation of 2-[2-(2-chlorothiazol-5-yl)-2-oxo-ethyl]sulfanyl-6-hydroxy-3-methyl-5-phenyl-pyrimidin-4-one of the formula 1, and thus eventually of the end product (I), step (a) was carried out with two different (1R,2R)-CsDPEN stereoisomers, namely with N-[(1R,2R)-2-amino-1,2-diphenyl-ethyl]-1-[(1S,4R)-7,7-dimethyl-2-oxo-norbornan-1-yl]methanesulfonamide) and with N-[(1R,2R)-2-amino-1,2-diphenyl-ethyl]-1-[(1R,4S)-7,7-dimethyl-2-oxo-norbornan-1-yl]methanesulfonamide) The reaction was carried out similarly to the first part of the above examples (i.e. proceeding before reacting with the activating agent), using DMAC as solvent, 1.2 eq. of formic acid, 0.8 eq. of diisopropylethylamine as base and 0.2 mol % of the catalyst RhClCp*·(1R,2R-CsDPEN-1) (formed in situ by mixing $[Rh(III)Cl_2Cp^*]_2$, N-[(1R,2R)-2-amino-1,2-diphenyl-ethyl]-1-[(1S,4R)-7,7-dimethyl-2-oxo-norbornan-1-yl]methanesulfonamide and diisopropylethylamine used in a molar ratio of 1:3:7) or 0.2 mol % of the catalyst RhClCp*·(1R,2R-CsDPEN-2) (formed in situ by mixing $[Rh(III)Cl_2Cp^*]_2$, N-[(1R,2R)-2-amino-1,2-diphenyl-ethyl]-1-[(1R,4S)-7,7-dimethyl-2-oxo-norbornan-1-yl] methanesulfonamide and diisopropylethylamine used in a molar ratio of 1:3:7). The reaction was carried out at −5° C.

The reaction in which RhClCp*·(1R,2R-CsDPEN-1) was used as catalyst yielded 2-R in an enantiomeric purity of 97% ee (conversion: 95%); the reaction in which RhClCp*·(1R,2R-CsDPEN-2) was used as catalyst yielded 2-R in an enantiomeric purity of 98% ee (conversion: 98%).

The invention claimed is:

1. A method for preparing an enantiomerically enriched form of 3-(2-chlorothiazol-5-yl)-8-methyl-7-oxo-6-phenyl-2,3-dihydrothiazolo[3,2-a]pyrimidin-4-ium-5-olate of formula (I):

(I)

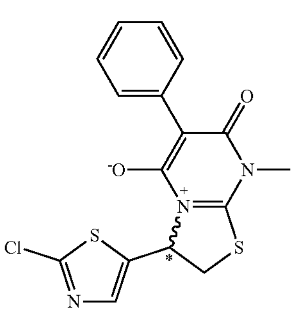

where the asterisk * shows the stereogenic center;

which method comprises (a) reducing 2-[2-(2-chlorothiazol-5-yl)-2-oxo-ethyl]sulfanyl-6-hydroxy-3-methyl-5-phenyl-pyrimidin-4-one of formula 1

1

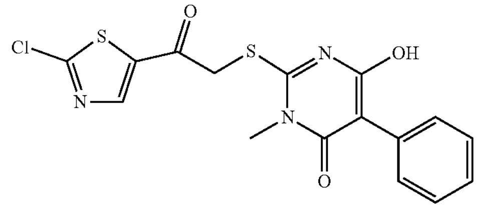

or a tautomer thereof or a mixture of different tautomers thereof with a reduction agent selected from the group consisting of formic acid HC(═O)OH, formates of formula HC (═O)$O^-M^+$, and mixtures of formic acid HC(═O)OH and one or more formates of formula HC (═O)$O^-M^+$, where $M^+$ is a cation equivalent; in the presence of a chiral transition metal catalyst and optionally a base, where in case that formic acid is used as the reduction agent, the reaction is carried out in the presence of a base;

to obtain a reaction mixture comprising an enantiomerically enriched form of 2-[2-(2-chlorothiazol-5-yl)-2-hydroxy-ethyl]sulfanyl-6-hydroxy-3-methyl-5-phenyl-pyrimidin-4-one of formula 2

2

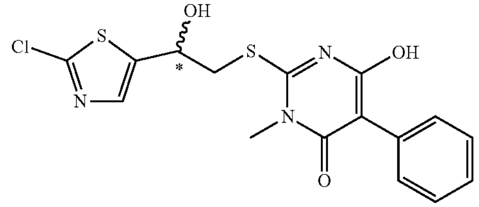

or of a tautomer thereof or a mixture of different tautomers thereof; and (b) reacting the reaction mixture obtained in step (a) with an activating agent which enhances electrophilicity of the carbon atom marked with the asterisk in the compound of formula 1 without promoting racemization at said carbon atom;

to obtain an enantiomerically enriched form of the compound of formula (I).

2. The method according to claim 1, where $M^+$ is selected from the group consisting of alkali metal cations, ammonium cations of the formula $[NHR^1R^2R^3]^+$, where $R^1$, $R^2$, and $R^3$, independently of each other, are selected from the group consisting of hydrogen, $C_1$-$C_6$-alkyl, $C_3$-$C_6$-cycloalkyl, $C_1$-$C_4$-alkoxy, and $C_1$-$C_4$-alkoxy-C1-C4-alkyl, protonated diamines of formula $NR^1R^2$-A-$NR^3R^4$, where $R^1$, $R^2$, $R^3$, and $R^4$, independently of each other, are selected from the group consisting of hydrogen, $C_1$-$C_6$-alkyl, $C_3$-$C_6$-cycloalkyl, $C_1$-$C_4$-alkoxy, and $C_1$-$C_4$-alkoxy-$C_1$-$C_4$-alkyl, and A is $(CH_2)_2$ or $(CH_2)_3$; and protonated 5- or 6-membered saturated heterocyclic rings containing one nitrogen atom as ring member and optionally one further heteroatom selected from N and O as ring member, where the ring optionally is substituted with 1 to 6 $C_1$-$C_4$-alkyl groups and/or 1 or 2 OH groups.

3. The method according to claim 1, where the base optionally used in step (a) is selected from the group consisting of alkali metal hydroxides, amines of the formula $NR^1R^2R^3$, where $R^1$, $R^2$, and $R^3$, independently of each other, are selected from the group consisting of hydrogen, $C_1$-$C_6$-alkyl, $C_3$-$C_6$-cycloalkyl, $C_1$-$C_4$-alkoxy, and $C_1$-$C_4$-alkoxy-$C_1$-$C_4$-alkyl, where at least one of $R^1$, $R^2$, and $R^3$ is not hydrogen; diamines of the formula $NR^1R^2$-A-$NR^3R^4$, where $R^1$, $R^2$, $R^3$, and $R^4$, independently of each other, are selected from the group consisting of hydrogen, $C_1$-$C_6$-alkyl, $C_3$-$C_6$-cycloalkyl, $C_1$-$C_4$-alkoxy, and $C_1$-$C_4$-alkoxy-$C_1$-$C_4$-alkyl, and A is $(CH_2)_2$ or $(CH_2)_3$; and a 5-or 6-membered saturated heterocyclic ring containing one nitrogen atom as ring member and optionally one further heteroatom selected from N and O as ring member, where the ring optionally is substituted with 1 to 6 $C_1$-$C_4$-alkyl groups and/or 1 or 2 OH groups, where the bases can be used in supported from.

4. The method according to claim 1, where in step (a) formic acid is used as reduction agent, where formic acid and the base are used in a molar ratio of from 100:1 to 1:10.

5. The method according to claim 1, where the chiral transition metal catalyst used in step (a) is selected from group VIII metal catalysts.

6. The method according to claim 5, where the chiral transition metal catalyst used in step (a) is selected from Ru, Rh, and Ir catalysts.

7. The method according to claim 1, where the chiral transition metal catalyst used in step (a), calculated on the basis of the transition metal content, is used in an amount of 0.01 to 10 mol % relative to 1 mol of the compound 1.

8. The method according to claim 1, where the chiral transition metal catalyst comprises one or more chiral ligands coordinated to a transition metal, where the chiral ligands are selected from the group consisting of bidentate amine-based chiral ligands; where the chiral ligands.

9. The method according to claim 8, where the chiral transition metal catalyst comprises one or more chiral ligands coordinated to a transition metal, where the chiral ligands are selected from the group consisting of the chiral forms of 1,2-diphenyl-ethylene-1,2-diamines of formula (II)

(II)

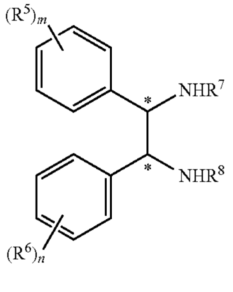

where an asterisk shows the stereogenic centers;

$R^5$ and $R^6$, independently of each other, are selected from the group consisting of OH, halogen, $C_1$-$C_4$-alkyl, and $C_1$-$C_4$-alkoxy;

$R^7$ and $R^8$, independently of each other, are selected from the group consisting of hydrogen, $C_1$-$C_4$-alkyl,-L-phenyl, where the phenyl ring are optionally substituted with 1, 2, 3, 4, or 5 substituents selected from the group consisting of $C_1$-$C_4$-alkyl, $C_1$-$C_4$-haloalkyl, and $C_1$-$C_4$-alkoxy; and $SO_2R^9$;

L is a linker selected from the group consisting of $C_2$-$C_6$-alkylene, $C_1$-$C_3$-alkylene-O—$(CH_2)_p$, where p is 0, 1 or 2; and $C_1$-$C_3$-alkylene-(1,2-phenylene)-(CH2) r, where r is 0, 1 or 2;

$R^9$ is selected from the group consisting of $C_1$-$C_4$-alkyl, C1-C4-haloalkyl, phenyl, phenyl-$C_1$-$C_3$-alkyl, where phenyl in the two aforementioned radicals are optionally substituted with 1, 2, 3, 4, or 5 substituents selected from the group consisting of halogen, $C_1$-$C_4$-alkyl, $C_1$-$C_4$-haloalkyl, and $C_1$-$C_4$-alkoxy; naphthyl, and $NR^{10}R^{11}$;

$R^{10}$ is hydrogen or $C_1$-$C_4$-alkyl;

$R^{11}$ is phenyl-$C_1$-$C_3$-alkyl, where the phenyl ring are optionally substituted with 1, 2, 3, 4, or 5 substituents selected from the group consisting of halogen, $C_1$-$C_4$-alkyl, $C_1$-$C_4$-haloalkyl, and $C_1$-$C_4$-alkoxy; and m and n, independently of each other, are 0, 1, 2, 3, 4, or 5.

10. The method according to claim 9, where the chiral ligands are selected from the group consisting of the (1R,2R) or (1S,2S) forms of DPEN, TsDPEN, $CF_3$TsDPEN, MSDPEN, MeMsDPEN, MeTsDPEN, FsDPEN, TripsMesitylDPEN, CsDPEN, MesitylDPEN, RsDPEN, TsDiOMeDPEN, or the compound of formula (II), wherein $R^7$ is $SO_2R^9$, where $R^9$ is $C_1$-$C_4$-alkyl or phenyl which are optionally substituted with 1, 2, or 3 substituents selected from the group consisting of $C_1$-$C_4$-alkyl and $C_1$-$C_4$-haloalkyl, $R^8$ is —$(CH_2)_3$-phenyl or —$(CH_2)_4$-phenyl, where phenyl in the two last-mentioned radicals are optionally substituted with 1, 2, or 3 substituents selected from the group consisting of $C_1$-$C_4$-alkyl, $C_1$-$C_4$-haloalkyl, and $C_1$-$C_4$-alkoxy; and m and n are 0; where the chiral transition metal catalyst is selected from catalysts containing Ru, Rh, or Ir as central metal.

11. The method according to claim 10, where the chiral transition metal catalyst is selected from catalysts containing Ru, Rh, or Ir as central metal and at least one chiral ligand selected from the group consisting of the (1R,2R) or (1S,2S) forms of DPEN, TsDPEN, $CF_3$TsDPEN, MsDPEN, MeMsDPEN, MeTsDPEN, FsDPEN, TripsMesitylDPEN, CsDPEN, MesitylDPEN, RsDPEN, and TsDiOMeDPEN; and from catalysts containing Ru as central metal and at least one ligand selected from the (1R,2R) or (1S,2S) forms of the compound of formula (II), wherein $R^7$ is $SO_2R^9$, where $R^9$ is $C_1$-$C_4$-alkyl or phenyl which are optionally substituted with 1, 2, or 3 substituents selected from the group consisting of $C_1$-$C_4$-alkyl and $C_1$-$C_4$-haloalkyl, $R^8$ is —$(CH_2)_3$-phenyl or —$(CH_2)_4$-phenyl, where phenyl in the two last-mentioned radicals are optionally substituted with 1, 2, or 3 substituents selected from the group consisting of $C_1$-$C_4$-alkyl, $C_1$-$C_4$-haloalkyl, and $C_1$-$C_4$-alkoxy; and m and n are 0.

12. The method according to claim 11, where the chiral transition metal catalyst is selected from catalysts containing Ru, Rh, or Ir as central metal and a chiral ligand selected from the group consisting of the (1R,2R) or (1S,2S) form of TsDPEN, MsDPEN, and CsDPEN.

13. The method according to claim 9, where in case that none of $R^7$ and $R^8$ is -L-phenyl or $SO_2R^9$ with $R^9$ being phenyl-$C_1$-$C_3$-alkyl or $NR^{10}R^{11}$, the catalyst contains additionally a ligand selected from Cp, Cp*, benzene, p-cymene, mesitylene, and hexamethylbenzene.

14. The method according to claim 9, where the chiral transition metal catalyst contains additionally a ligand selected from halogen and sulfonate ligands.

15. The method according to claim 9, where the chiral transition metal catalyst is selected from catalysts containing Ru, Rh, or Ir as central metal, a chiral ligand selected from the group consisting of the (1R,2R) or (1S,2S) form of TsDPEN, MsDPEN, and CsDPEN, a ligand selected from halogen ligands, and a further ligand selected from Cp*, p-cymene, and mesitylene.

16. The method according to claim 1, where in step (a) 2-[(2S)-2-(2-chlorothiazol-5-yl)-2-hydroxy-ethyl]sulfanyl-6-hydroxy-3-methyl-5-phenyl-pyrimidin-4-one of formula 2-S or a tautomer thereof or a mixture of different tautomers thereof

2-S

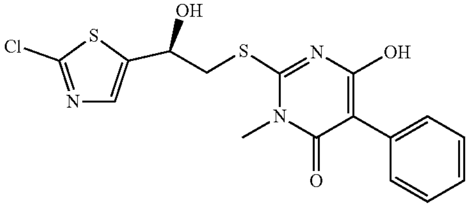

in an enantiomeric excess of at least 55% ee is prepared, where to this end in step (a) a chiral transition metal catalyst comprising the (1S,2S) form of a chiral ligand of formula (II) is used.

17. The method according to claim 1, where in step (a) 2-[(2R)-2-(2-chlorothiazol-5-yl)-2-hydroxy-ethyl]sulfanyl-6-hydroxy-3-methyl-5-phenyl-pyrimidin-4-one of formula 2-R or a tautomer thereof or a mixture of different tautomers thereof

2-R

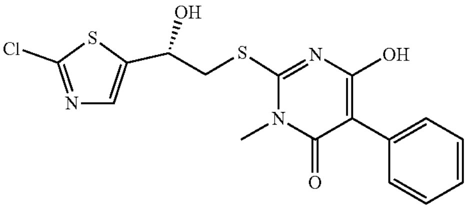

in an enantiomeric excess of at least 55% ee, is prepared, where to this end in step (a) a chiral transition metal catalyst comprising the (1R,2R) form of a chiral ligand of formula (II) is used.

18. The method according to claim 1, where the activating agent used in step (b) is selected from the group consisting of $P(OR^1)_2Cl$, $P(OR^1)Cl_2$, $P(=O)(OR^1)_2Cl$, $P(=O)(OR^1)Cl_2$, where each $R^1$ in the four aforementioned compounds is independently $C_1$-$C_4$-alkyl; $PCl_3$, $P(=O)Cl_3$, polyphosphoric acid, $P_4O_{10}$, Mitsunobu-type reagents, triphenylphosphine in combination with a halogenating agent, $SO_3$ complexes with Lewis bases selected from amines, carboxamides and heteroaromatic compounds containing 1, 2, or 3 basic nitrogen ring atoms; $S(O)Cl_2$, $CH_3S(O)_2Cl$, carbonyldiimidazole (CDI), Vilsmeier reagent, complexes of N,N-dimethylformamide and/or N,N-dimethylacetamide with a Lewis acid; and mixtures of two or more of the aforementioned activating agents.

19. The method according to claim 18, where the activating agent used in step (b) is selected from the group consisting of $P(OR^1)_2Cl$, $P(OR^1)Cl_2$, $P(=O)(OR^1)_2Cl$, where each $R^1$ in the three aforementioned compounds is independently $C_1$-$C_4$-alkyl; $PCl_3$, $P(O)Cl_3$, $SO_3$/dimethyl formamide complex, $SOCl_2$, $CH_3S(=O)_2Cl$, CDI, and Mitsunobu-type reagents.

20. The method according to claim 19, where the activating agent used in step (b) is selected from the group consisting of dimethyl chlorophosphite ($P(OCH_3)_2Cl$) and diethyl chlorophosphite ($P(OCH_2CH_3)_2Cl$).

21. The method according claim 1, where the activating agent is used in an amount such that a molar ratio of the compound of formula 1 and the activating agent is in a range of from 10:1 to 1:10.

22. The method according claim 1, for preparing (3R)-3-(2-chlorothiazol-5-yl)-8-methyl-7-oxo-6-phenyl-2,3-dihydrothiazolo[3,2-a]pyrimidin-4-ium-5-olate of formula (I-R)

(I-R)

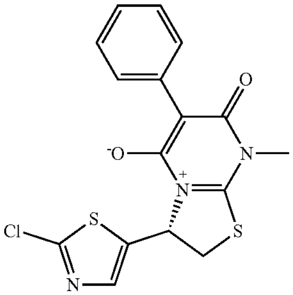

in an enantiomeric excess of at least 55% ee;

which method comprises (a.1) reducing the compound of formula 1 or a tautomer thereof or a mixture of different tautomers thereof so that a reaction mixture containing 2-[(2S)-2-(2-chlorothiazol-5-yl)-2-hydroxy-ethyl]sulfanyl-6-hydroxy-3-methyl-5-phenyl-pyrimidin-4-one of formula 2-S or a tautomer thereof or a mixture of different tautomers thereof

2-S

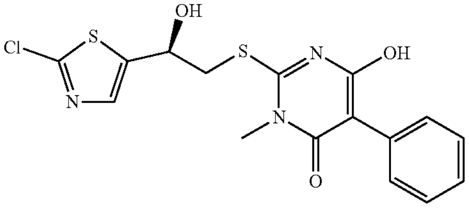

in an enantiomeric excess of at least 55% ee, or a tautomer thereof is formed; and (b.1) reacting the reaction mixture obtained in step (a.1) with an activating agent;

or for preparing (3S)-3-(2-chlorothiazol-5-yl)-8-methyl-7-oxo-6-phenyl-2,3-dihydrothiazolo[3,2-a]pyrimidin-4-ium-5-olate of formula (I-S)

(I-S)

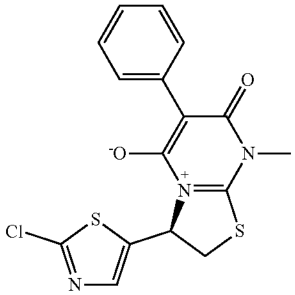

in an enantiomeric excess of at least 55% ee;

which method comprises (a.2) reducing the compound of formula 1 or a tautomer thereof or a mixture of different tautomers thereof so that a reaction mixture containing 2-[(2R)-2-(2-chloro-thiazol-5-yl)-2-hydroxy-ethyl]sulfanyl-6-hydroxy-3-methyl-5-phenyl-pyrimidin-4-one of formula 2-R or a tautomer thereof or a mixture of different tautomers ‘thereof

2-R

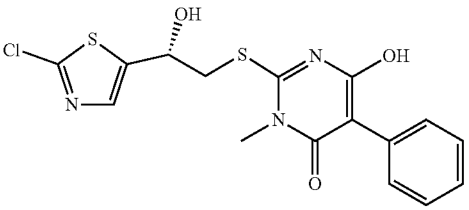

in an enantiomeric excess of at least 55% ee or a tautomer thereof or a mixture of different tautomers thereof is formed; and (b.2) reacting the reaction mixture obtained in step (a.1) with an activating agent.

23. The method according to claim 2 where $M^+$ is selected from the group consisting of $Li^+$, $Na^+$, $K^+$, $Cs^+$, $NH_4^+$, $[NH_2(C_2H_5)_2]^+$, $[NH(C_2H_5)_3]^+$, $[NH(CH_2CH_2CH_2CH_3)_3]^+$, $[NH(C_2H_5)(CH(CH_3)_2]^+$, $[NH(CH_3)_2(CH(CH_3)]^+$, $[NH_2(C_2H_5)(C(CH_3)_3]^+$, $[NH_2(CH(CH_3)_2)C(CH_3)_3]^+$, $[NH_2(C_2H_4OCH_3)(CH_3)]^+$, $[NH(cyclohexyl)_2(CH_3)]^+$, $[NH(cyclohexyl)(CH_3)_2]^+$, protonated N,N,N',N'-tetramethylethylenediamine, protonated N,N,N',N'-tetramethylpropylene-1,3-diamine, protonated piperdine, protonated N-methylpiperidine, protonated 2,2,6,6-tetramethylpiperidine, protonated N-methyl-2,6,6-tetramethylpiperidine, protonated N-methyl-4-hydroxy-2,2,6,6-tetramethylpiperidine, protonated morpholine, and protonated N-methylmorpholine.

24. The method according to claim 8 where the chiral ligands are selected from the group consisting of chiral 1,2-diphenyl-ethylene-1,2-diamines, 1,2-cyclohexanediamines, and 1,2-bis(methylamino)cyclohexanes.

25. The method according to claim 10 where at least one chiral ligand selected from the group consisting of the (1R,2R) or (1S,2S) form of DPEN, TsDPEN, $CF_3$TsDPEN, MsDPEN, MeMsDPEN, MeTsDPEN, FsDPEN, TripsMesitylDPEN, CsDPEN, MesitylDPEN, RsDPEN, TsDiOMeDPEN or the compound of formula (II), wherein $R^7$ is $SO_2R^9$, where $R^9$ is $C_1$-$C_4$-alkyl or phenyl which optionally are substituted with 1, 2, or 3 substituents selected from the group consisting of $C_1$-$C_4$-alkyl and $C_1$-$C_4$-haloalkyl; $R^8$ is $-(CH_2)_3$-phenyl or $-(CH_2)_4$-phenyl, where phenyl in the two last-mentioned radicals carry 1, 2, or 3 substituents selected from the group consisting of $C_1$-$C_4$-alkyl, $C_1$-$C_4$-haloalkyl, and $C_1$-$C_4$-alkoxy; and m and n are 0.

* * * * *